US012751894B2

(12) United States Patent
Kaufman et al.

(10) Patent No.: US 12,751,894 B2
(45) Date of Patent: Oct. 6, 2026

(54) SELECTIVE ACTIVATION OF CHEST COMPRESSIONS SYNCHRONIZED WITH MYOCARDIAL ACTIVITY

(71) Applicant: ZOLL Medical Corporation, Chelmsford, MA (US)

(72) Inventors: Christopher L. Kaufman, Somerville, MA (US); Joshua W. Lampe, Groton, MA (US); Gary A. Freeman, Waltham, MA (US); Naveed Zaidi, Shrewsbury, MA (US); Annemarie E. Silver, Bedford, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 1220 days.

(21) Appl. No.: 17/626,148

(22) PCT Filed: Jul. 10, 2020

(86) PCT No.: PCT/US2020/041612
§ 371 (c)(1),
(2) Date: Jan. 11, 2022

(87) PCT Pub. No.: WO2021/007518
PCT Pub. Date: Jan. 14, 2021

(65) Prior Publication Data

US 2023/0149258 A1 May 18, 2023

Related U.S. Application Data

(60) Provisional application No. 62/872,837, filed on Jul. 11, 2019.

(51) Int. Cl.
*A61H 31/00* (2006.01)
*A61N 1/39* (2006.01)

(52) U.S. Cl.
CPC ....... *A61H 31/005* (2013.01); *A61N 1/39044* (2017.08)

(58) Field of Classification Search
CPC .... A61H 31/00; A61H 31/004; A61H 31/005; A61H 31/006; A61N 1/39044
See application file for complete search history.

(56) References Cited

U.S. PATENT DOCUMENTS

| | | | | |
|---|---|---|---|---|
| 5,490,820 A * | 2/1996 | Schock | ................ | A61H 31/006 601/1 |
| 6,179,793 B1 * | 1/2001 | Rothman | ............. | A61H 31/006 600/521 |

(Continued)

FOREIGN PATENT DOCUMENTS

| | | |
|---|---|---|
| WO | 2008059394 | 5/2008 |
| WO | 2017072626 | 5/2017 |

OTHER PUBLICATIONS

International Search Report and Written Opinion for PCT Application No. PCT/US2020/041612 mailed on Oct. 13, 2020, 11 pages.

*Primary Examiner* — Timothy A Stanis
*Assistant Examiner* — Christopher E Miller
(74) *Attorney, Agent, or Firm* — ZOLL Medical Corporation

(57) ABSTRACT

Systems and methods for providing resuscitative chest compressions to a chest of a patient are described. One exemplary system may include a chest compressor for administering chest compressions to the patient, one or more sensors for measuring and generating electrocardiogram (ECG) signals of the patient's heart. The system may include at least one processor coupled to memory and configured to receive and analyze the signals corresponding to the ECG, determine an intrinsic heart rate, identify at least one ECG waveform within the ECG signals, select a chest compression protocol from at least three or at least four predeter- (Continued)

mined chest compression protocols for administration to the patient based at least in part on the intrinsic heart rate of the patient, and control the chest compressor based on the selected chest compression protocol.

39 Claims, 28 Drawing Sheets

(56) References Cited

U.S. PATENT DOCUMENTS

| | | | | |
|---|---|---|---|---|
| 9,084,545 | B2 | 7/2015 | Sullivan et al. | |
| 9,259,543 | B2 | 2/2016 | Paradis et al. | |
| 2005/0075531 | A1* | 4/2005 | Loeb | A61H 9/0078 600/17 |
| 2005/0131465 | A1* | 6/2005 | Freeman | A61N 1/3625 607/5 |
| 2006/0094991 | A1* | 5/2006 | Walker | A61H 31/006 601/41 |
| 2008/0171311 | A1* | 7/2008 | Centen | A61H 31/005 601/41 |
| 2012/0016179 | A1* | 1/2012 | Paradis | A61N 1/3987 601/41 |
| 2013/0296727 | A1* | 11/2013 | Sullivan | A61N 1/3993 600/513 |
| 2014/0336546 | A1* | 11/2014 | Chapman | A61H 31/007 601/41 |
| 2016/0136042 | A1* | 5/2016 | Nilsson | A61H 31/006 601/41 |
| 2017/0035650 | A1* | 2/2017 | Taylor | A61H 31/005 |
| 2017/0105898 | A1* | 4/2017 | Taylor | G06T 7/0012 |
| 2018/0185240 | A1* | 7/2018 | Von Schenck | A61H 31/006 |
| 2019/0117504 | A1* | 4/2019 | von Schenck | A61H 31/005 |
| 2019/0374428 | A1* | 12/2019 | Kaufman | A61N 1/39044 |
| 2021/0169736 | A1* | 6/2021 | Wijshoff | A61H 31/005 |

* cited by examiner

391

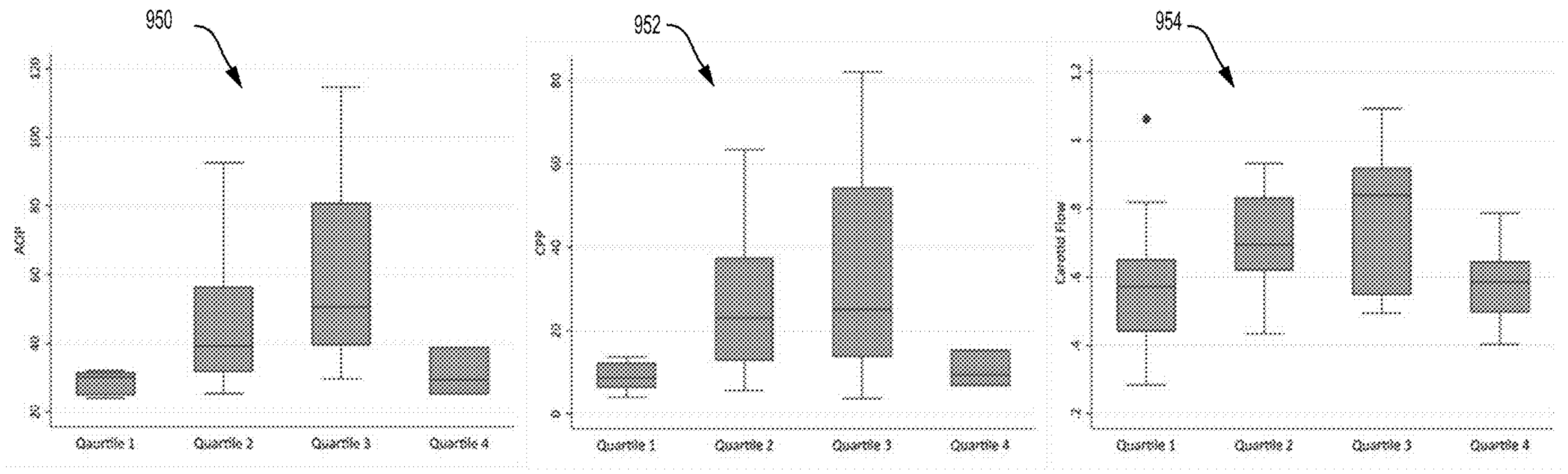

FIG. 9C

| | | | | | |
|---|---|---|---|---|---|
| Mean Arterial Pressure | mmHg | 33.4 ± 0.5 | 38.2 ± 0.5 | 40.1 ± 0.5 * | 34.7 ± 0.5 |
| Aortic Systolic Pressure | mmHg | 68.4 ± 0.6 | 73.3 ± 0.6 * | 75.5 ± 0.6* | 72.5 ± 0.6 |
| Aortic Diastolic Pressure | mmHg | 15.7 ± 0.5 | 20.4 ± 0.5 * | 20.3 ± 0.5 * | 14.6 ± 0.5 |
| Right Atrial Pressure | mmHg | 40.3 ± 0.3 | 39.9 ± 0.2 | 38.2 ± 0.3 | 35.1 ± 0.2* |
| Coronary Perfusion Pressure | mmHg | 13.0 ± 0.5 | 15.7 ± 0.4 * | 14.7 ± 0.4 * | 11.6 ± 0.4 |
| Intra-Cranial Pressure | mmHg | 29.0 ± 0.1 | 29.3 ± 0.1 | 28.7 ± 0.1 | 28.1 ± 0.1* |
| Cerebral Perfusion Pressure | mmHg | 33.2 ± 0.5 | 37.8 ± 0.5* | 38.6 ± 0.5* | 33.7 ± 0.5 |
| Carotid Blood Flow | mL/comp | 0.56 ± 0.01 | 0.65 ± 0.01 | 0.86 ± 0.01* | 0.72 ± 0.01 |
| Jugular Blood Flow | mL/comp | 0.25 ± 0.01 | 0.33 ± 0.01* | 0.35 ± 0.01* | 0.30 ± 0.01 |

* statistically different from other condition

FIG. 9D

SELECTIVE ACTIVATION OF CHEST COMPRESSIONS SYNCHRONIZED WITH MYOCARDIAL ACTIVITY

This application claims priority to U.S. Prov. App. No. 62/872,837, filed on Jul. 11, 2019 and PCT International Application No PCT/US2020/041612 filed on Jul. 10, 2020.

BACKGROUND

Cardiac arrest and other cardiac conditions are a major cause of death in the United States and around the world. Various resuscitation techniques, such as cardiopulmonary resuscitation (CPR), aim to maintain and/or restore a patient's circulatory and respiratory systems during cardiac arrest.

In general, during the administration of CPR, a patient's chest is repeatedly compressed so as to facilitate blood circulation throughout the patient's body. Additionally, periodic ventilations may also be provided to supply oxygen to the lungs and other organs within the body. Additionally, depending on the patient's medical condition, rescuers may administer shock therapies and/or medications to assist in the restoration of cardiopulmonary function to the patient.

SUMMARY

A category or categories of cardiac conditions may be referred to as pseudo-pulseless electrical activity (p-PEA) or pulseless electrical activity (PEA), which may also be recognized as electromechanical dissociation (EMD) of the heart. In some cases, when a patient is observed to exhibit symptoms including unconscious hypotension yet experiencing organized ECG (electrocardiogram) activity, with weak or no mechanical contraction of the heart muscle, the patient may be considered to be suffering from p-PEA, PEA, or EMD. For example, the patient may be experiencing unconscious hypotension with an organized ECG, with extremely weak hemodynamics. During unconscious hypotension with an organized ECG, while the heart may exhibit a relatively organized rhythm, these rhythms may not correlate with life-sustaining mechanical activity of the heart. That is, there may be detectable organized electrical activity of the myocardium, but weak or non-existent contractions of the heart muscle resulting in poor blood circulation that may not be life-sustaining. Such a state of unconscious hypotension with organized ECG activity can be life-threatening if left untreated. It is to be understood that embodiments of the present disclosure where one or more chest compression protocols are administered to a patient based on intrinsic electrical activity of the heart may apply to patients in states including PEA or true-PEA, p-PEA and EMD, among others.

The systems and methods detailed below relate to techniques and devices that may be used to increase cardiac output for patient(s) suffering from cardiac ailments. One example of a system for providing resuscitative chest compressions to a chest of the patient may include a chest compressor configured to be applied to the chest of the patient and to administer chest compressions to the patient, and may include one or more sensors communicatively coupled to a medical device and configured to sense electrocardiogram (ECG) signals of the patient and to transmit the ECG signals to the medical device. The medical device may include at least one processor coupled to memory of the medical device, the at least one processor and memory configured to receive the ECG signals, determine an intrinsic heart rate of the patient based on the ECG signals (even if the patient has no actual mechanical contraction of the heart muscle so as to generate life-sustaining blood flow), and identify at least one ECG waveform feature within the ECG signals. Additionally, the at least one processor may control the chest to select a chest compression protocol from one of at least three predetermined chest compression protocols for administration to the patient based on the intrinsic heart rate of the patient. Or, the at least one processor may select a chest compression protocol from at least three, four, or more predetermined chest compression protocols for administration to the patient based on the intrinsic heart rate of the patient, and control the chest compressor based on the selected chest compression protocol.

One example of a system for providing resuscitative chest compressions to a chest of the patient may include a chest compressor configured to be applied to the chest of the patient and to administer chest compressions to the patient, and includes one or more sensors communicatively coupled to a medical device and configured to measure and generate signals corresponding to an electrocardiogram (ECG) of a heart of the patient and to transmit the signals to the medical device. The medical device may include at least one processor coupled to memory of the medical device, the at least one processor and memory configured to, receive and analyze the signals corresponding to the ECG of the heart, determine an intrinsic heart rate of the patient based on the analyzed signals corresponding to the ECG, and identify at least one ECG waveform feature within the signals corresponding to the ECG. Additionally, the processor may control the chest compressor to administer a first chest compression protocol when the intrinsic heart rate of the patient falls within a first range, administer a second chest compression protocol when the intrinsic heart rate of the patient falls within a second range, and administer a third chest compression protocol when the intrinsic heart rate of the patient falls within a third range.

In some examples, selecting the chest compression protocol from at least three predetermined chest compression protocols may include selecting the chest compression protocol from at least four predetermined chest compression protocols. The at least four predetermined chest compression protocols may include a first chest compression protocol, a second chest compression protocol and a third chest compression protocol that each includes compressions synchronized with the at least one identified ECG waveform feature, and the at least four predetermined chest compression protocols may include a fourth chest compression protocol that includes unsynchronized chest compressions. The first chest compression protocol may be selected based on whether the intrinsic heart rate of the patient falls within a first range, the second chest compression protocol may be selected based on whether the intrinsic heart rate of the patient falls within a second range, the third chest compression protocol may be selected based on whether the intrinsic heart rate of the patient falls within a third range, and the fourth chest compression protocol may be selected based on whether the intrinsic heart rate of the patient falls within a fourth range. The first chest compression protocol, the second chest compression protocol and the third chest compression protocol may each include compressions synchronized with the at least one identified ECG waveform feature, and the fourth chest compression protocol may include unsynchronized chest compressions.

The first range may include an intrinsic heart rate of between approximately 60 and approximately 120 beats per minute. The second range may include a heart rate of between approximately 40 beats per minute and approximately 60 beats per minute. The second chest compression protocol may include compressions synchronized with the at least one identified ECG waveform feature with at least one additional compression interposed between the compressions synchronized with the at least one identified ECG waveform feature. The third range may include an intrinsic heart rate between approximately 20 and approximately 40 beats per minute. The third chest compression protocol may include compressions synchronized with the at least one identified ECG waveform feature with at least two additional compressions interposed between the compressions synchronized with the at least one identified ECG waveform feature. The fourth range may include an intrinsic heart rate between approximately 0 and approximately 20 beats per minute. The fourth protocol may include compressions administered according to a predetermined rate. The predetermined rate may include chest compressions delivered at a rate between approximately 80 and approximately 100 compressions per minute.

In some examples, the at least four predetermined chest compression protocols may include a fifth chest compression protocol for administration to the patient when the intrinsic heart rate of the patient falls within a fifth range. The fifth range may include a heart rate of between approximately 120 beats per minute and approximately 150 beats per minute. The fifth chest compression protocol may include compressions synchronized with the at least one identified ECG waveform feature and adjustment of at least one chest compression parameter.

In some examples, the at least four predetermined chest compression protocols includes a sixth chest compression protocol for administration to the patient when the intrinsic heart rate of the patient falls within a sixth range. The sixth range may include a heart rate of greater than approximately 150 beats per minute. The at least one processor may be configured to initiate a shock protocol or potentially initiate a shock protocol when the intrinsic heart rate of the patient falls within the sixth range.

Another example of a system for providing resuscitative chest compressions to the chest of a patient may comprise a chest compressor configured to be applied to the chest of the patient and administer chest compressions to the patient, and one or more sensors communicatively coupled to a medical device and configured to measure and generate signals corresponding to an electrocardiogram (ECG) of the heart of the patient and transmit the signals to the medical device. The medical system may include at least one processor coupled to memory of the medical device, the at least one processor and memory configured to receive and analyze the signals corresponding to the ECG of the heart, determine an intrinsic heart rate of the patient based on the analyzed signals corresponding to the ECG, and identify at least one ECG waveform feature within the signals corresponding to the ECG. Additionally, processor may control the chest compressor to: administer a chest compression protocol when the intrinsic heart rate of the patient falls within a fourth range, wherein the compressions are synchronized with the at least one identified ECG waveform feature when the intrinsic heart rate of the patient falls within the fourth range, and adjust at least one chest compression parameter when the intrinsic heart rate of the patient falls within the fourth range.

Another example of a system for providing resuscitative chest compressions to a chest of a patient may comprise a chest compressor configured to be applied to the chest of the patient and administer chest compressions to the patient, and may further comprise one or more sensors communicatively coupled to a medical device and configured to measure and generate signals corresponding an electrocardiogram (ECG) of the heart of the patient and transmit the signals to the medical device. The system may further include at least one processor coupled to memory of the medical device, the at least one processor and memory configured to receive and analyze the signals corresponding to the ECG of the heart, and determine an intrinsic heart rate of the patient based on the analyzed signals corresponding to the ECG, identify at least one ECG waveform feature within the signals corresponding to the ECG. The processor may also control the chest compressor to administer a first chest compression protocol when the intrinsic heart rate of the patient falls within a first range, administer a second first chest compression protocol when the intrinsic heart rate of the patient falls within a second range, administer a third chest compression protocol when the intrinsic heart rate of the patient falls within a third range, determine at least one threshold crossing of the intrinsic heart rate between the first range and the second range or the second range and third range, and adjust at least one of the first range and the second range in response to the at least one threshold crossing of the intrinsic heart rate.

Another example of a system for providing resuscitative chest compressions to a chest of a patient may comprise a chest compressor configured to be applied to the chest of the patient and administer chest compressions to the patient and one or more sensors communicatively coupled to a medical device and configured to measure and generate signals corresponding an electrocardiogram (ECG) of the heart of the patient and transmit the signals to the medical device. The system may further include at least one processor coupled to memory of the medical device, the at least one processor and memory configured to receive and analyzing the signals corresponding to the ECG of the heart, and determine an intrinsic heart rate of the patient based on the analyzed signals corresponding to the ECG, and identify at least one ECG waveform feature within the signals corresponding to the ECG of the heart. The processor may control the chest compressor to administer compressions synchronized with the at least one identified ECG waveform feature, and pause the chest compressor from administering one or more chest compressions to allow for a check for return of spontaneous circulation (ROSC).

Implementations of such systems may include one or more of the following features. For example, the at least three predetermined chest compression protocols may comprise a first chest compression protocol and a second chest compression protocol that each comprises compressions synchronized with the at least one identified ECG waveform feature, and the at least three predetermined chest compression protocols may comprise a third chest compression protocol that comprises unsynchronized chest compressions.

In some examples, the first chest compression protocol may be selected based on whether the intrinsic heart rate of the patient falls within a first range, and the second chest compression protocol may be selected based on whether the intrinsic heart rate of the patient falls within a second range, and the third chest compression protocol may be selected based on whether the intrinsic heart rate of the patient falls within a third range. In some examples, the at least three predetermined chest compression protocols may comprise a fourth chest compression protocol for administration to the patient when the intrinsic heart rate of the patient falls within a fourth range.

In some examples, the first range corresponding to the first chest compression protocol may comprise an intrinsic heart rate of between approximately 60 and approximately 120 beats per minute. In some examples, the second chest compression protocol may comprise compressions synchronized with the at least one identified ECG waveform feature with at least one additional compression interposed between the compressions synchronized with the at least one identified ECG waveform feature. The at least one additional compression may comprise multiple compressions interposed between the compressions synchronized with the at least one identified ECG waveform feature. In some examples, the second range corresponding to the second chest compression protocol may comprise a heart rate of between approximately 40 beats per minute and approximately 60 beats per minute.

In some examples, the third chest compression protocol may comprise compressions administered according to a predetermined rate. The predetermined rate may comprise chest compressions delivered at a rate between approximately 80 and approximately 100 compressions per minute. In some examples, the third range corresponding to the third chest compression protocol may comprise an intrinsic heart rate between 0 and 40 beats per minute.

In some examples, the fourth chest compression protocol may comprise compressions synchronized with the at least one identified ECG waveform feature and adjustment of at least one chest compression parameter. The at least one chest compression parameter may comprise at least one of: a compression depth, a compression hold time, a compression release velocity, a compression downstroke time, a compression upstroke time, and a compression force. In some examples, the adjustment of the at least one chest compression parameter may comprise a reduction in compression depth from an initial compression depth. In some examples, the adjustment of the at least one chest compression parameter may comprise a reduction in compression hold time from an initial compression hold time. In some examples, the at least one chest compression parameter may comprise an increase in compression release velocity from an initial compression release velocity. Or, the adjustment of the at least one chest compression parameter may comprise a reduction in compression downstroke time from an initial compression downstroke time, or a reduction in compression upstroke time from an initial compression upstroke time. In some examples, the fourth range corresponding to the fourth chest compression protocol comprises a heart rate of between approximately 120 beats per minute and approximately 150 beats per minute.

In certain examples, the at least one processor may be configured to initiate a shock protocol when the intrinsic heart rate of the patient falls within a fifth range. The shock protocol may involve analysis of the signals corresponding to the electrocardiogram (ECG) of the heart of the patient to identify shockable rhythms, and application of one or more therapeutic shocks in response to identifying the shockable rhythms. In some examples, the fifth range corresponding to the shock protocol may comprise a heart rate of greater than approximately 150 beats per minute.

In some examples, the at least one processor may be configured to adjust at least one of: the first range, the second range, and the third range, in response to a determination that the intrinsic heart rate of the patient has fallen within the first range, the second range, or the third range multiple times within a predetermined interval of time. The adjustment of at least one of the ranges may comprise an increase in the third range. Or, the adjustment of the third range may comprise adjustment of the third range to between 0 and approximately 45 beats per minute. Or, the adjustment of the second range may comprise adjustment of the second range to approximately between 45 beats per minute and approximately 60 beats per minute.

In various implementations, the at least one processor may comprise a first processor configured to process the ECG signals corresponding to the ECG of the heart, and the at least one processor may comprise a second processor configured to control the chest compressor to provide the chest compressions. Alternatively, the at least one processor may comprise a single processor configured to process the ECG signals corresponding to the ECG of the heart, and control the chest compressor to provide the chest compressions. In some examples, the at least one processor and memory may be disposed in a medical device comprising at least one of: a defibrillator-monitor, an automated external defibrillator, an automated chest compressor, a wearable defibrillator, and an active compression-decompression device. In certain examples, the chest compressor may comprise a compression belt and a belt tensioner configured to tighten the compression belt around a thorax of the patient in order to compress the thorax of the patient at a resuscitative rate. Or, the chest compressor may be a piston-based system that comprises: a piston, a piston driver, support structures for supporting the piston and piston driver, and a compression pad affixed to the piston.

In some examples of the present disclosure, the at least one ECG waveform feature may include at least one of: a QRS complex, a leading edge of an R-wave, a peak of an R-wave, and a Q-wave. For example, the identified at least one ECG waveform feature may comprise the peak of the R-wave. Alternatively, or in addition, the at least one processor coupled to memory may be configured to analyze the generated ECG signals to determine a time window relative to the peak of the R-wave within which to apply chest compressions. The time window within which to apply chest compressions may be from approximately 125 milliseconds before the peak of the R-wave to 150 milliseconds after the peak of the R-wave. In some examples, the compressions synchronized with the peak of the R-wave may comprise timing the chest compressions such that a target depth of the chest compressions occurs prior to the peak of the R-wave. Or, the compressions synchronized with the peak of the R-wave may comprise timing the chest compressions such that a target depth of the chest compressions occurs after the peak of the R-wave. In some examples, the timing of the chest compressions may comprise reaching the target depth of the chest compressions within 150 milliseconds after the peak of the R-wave.

In various implementations, the at least one processor may be configured to pause the chest compressor from administering one or more chest compressions during a check for return of spontaneous circulation (ROSC) or in response to a determination that the patient has achieved ROSC. In some examples, the at least one processor may be configured to determine whether the patient is deteriorating or improving and, in response, adjust at least one chest compression parameter. The determination of whether the patient is deteriorating or improving may be based on at least one measured parameter of the patient, the at least one measured parameter including at least one of: a blood pressure, an ECG waveform, a measure of CO2 of the patient, an ETCO2 value of the patient, and a measure of blood flow of the patient. The at least one chest compression parameter may comprise at least one of: a compression depth, a compression hold time, a compression release velocity, a compression downstroke time, a compression upstroke time, and a compression force.

Implementations of such systems may also include one or more of the following features. For example, the one of at least three predetermined chest compression protocols may comprise a first chest compression protocol for administration to the patient when the intrinsic heart rate of the patient falls within a first range. The one of at least three predetermined chest compression protocols may comprise a second chest compression protocol for administration to the patient when the intrinsic heart rate of the patient falls within a second range. The one of at least three predetermined chest compression protocols may comprise a third chest compression protocol for administration to the patient when the intrinsic heart rate of the patient falls within a third range. The first chest compression protocol may comprise compressions synchronized with the at least one identified ECG waveform feature. The first range may comprise a heart rate of between approximately 60 beats per minute and approximately 120 beats per minute. The second chest compression protocol may comprise compressions synchronized with the at least one identified ECG waveform feature with at least one additional compression interposed between the compressions synchronized with the at least one identified ECG waveform feature. The at least one additional compression may comprise multiple compressions interposed between the compressions synchronized with the at least one identified ECG waveform feature. The second range may comprise a heart rate of between approximately 40 beats per minute and approximately 60 beats per minute. The third chest compression protocol may comprise unsynchronized chest compressions. The third chest compression protocol may comprise compressions administered according to a predetermined rate. The predetermined rate may comprise chest compressions delivered at a rate between approximately 80 and approximately 100 compressions per minute. The third range may comprise an intrinsic heart rate between 0 and 40 beats per minute.

In some examples, the at least one processor may comprise a first processor configured to process the ECG signals corresponding to the ECG of the heart, the at least one processor may comprise a second processor configured to control the chest compressor to provide the chest compressions. Alternatively, the at least one processor may comprise a single processor configured to process the ECG signals corresponding to the ECG of the heart, and control the chest compressor to provide the chest compressions. The at least one processor and memory may be disposed in a medical device comprising at least one of: a defibrillator-monitor, an automated external defibrillator, an automated chest compressor, a wearable defibrillator, and an active compression-decompression device.

In certain examples, the one of at least three predetermined chest compression protocols may comprise a fourth chest compression protocol for administration to the patient when the intrinsic heart rate of the patient falls within a fourth range. The fourth chest compression protocol may comprise compressions synchronized with the at least one identified ECG waveform feature and adjustment of at least one chest compression parameter. The at least one chest compression parameter may comprise at least one of: a compression depth, a compression hold time, a compression release velocity, a compression downstroke time, a compression upstroke time, and a compression force. The adjustment of the at least one chest compression parameter may comprise a reduction in compression depth from an initial compression depth. The adjustment of the at least one chest compression parameter may comprise a reduction in compression hold time from an initial compression hold time. The adjustment of the at least one chest compression parameter may comprise an increase in compression release velocity from an initial compression release velocity. The adjustment of the at least one chest compression parameter may comprise a reduction in compression downstroke time from an initial compression downstroke time, or a reduction in compression upstroke time from an initial compression upstroke time. The fourth range may comprise a heart rate of between approximately 120 beats per minute and approximately 150 beats per minute. The at least one processor may be configured to initiate a shock protocol when the intrinsic heart rate of the patient is greater than approximately 150 beats per minute. The shock protocol may involve analysis of the signals corresponding to the electrocardiogram (ECG) of the heart of the patient to identify shockable rhythms, and application of one or more therapeutic shocks in response to identifying the shockable rhythms.

In some examples, the at least one processor may be configured to pause the chest compressor from administering one or more chest compressions during a check for return of spontaneous circulation (ROSC) or in response to a determination that the patient has achieved ROSC. The at least one processor may be configured to determine whether the patient is deteriorating or improving and, in response, adjust at least one chest compression parameter. The determination of whether the patient is deteriorating or improving may be based on at least one measured parameter of the patient, the at least one measured parameter including at least one of: a blood pressure, an ECG waveform, a measure of CO2 of the patient, an ETCO2 value of the patient, and a measure of blood flow of the patient. The at least one processor may be configured to adjust at least one of: the first range, the second range, and the third range, in response to a determination that the intrinsic heart rate of the patient has fallen within the first range, the second range, or the third range multiple times within a predetermined interval of time. The adjustment of at least one of the ranges may comprise an increase in the third range. The adjustment of the third range may comprise adjustment of the third range to between 0 and approximately 45 beats per minute. The adjustment of the second range may comprise adjustment of the second range to approximately between 45 beats per minute and approximately 60 beats per minute. The at least one ECG waveform feature may include at least one of: a QRS complex, a leading edge of an R-wave, a peak of an R-wave, and a Q-wave.

In certain examples, the chest compressor may comprise a compression belt and a belt tensioner configured to tighten the compression belt around a thorax of the patient in order to compress the thorax of the patient at a resuscitative rate. The chest compressor may comprise a piston-based system that comprises: a piston, a piston driver, support structures for supporting the piston and piston driver, and a compression pad affixed to the piston.

In some examples, the at least one processor coupled to memory may be configured to analyze the generated ECG signals to determine a time window relative to the identified at least one ECG waveform feature within which to apply chest compressions. The identified at least one ECG waveform feature may comprise the peak of an R-wave of the patient. The time window within which to apply chest compressions may be from approximately 125 milliseconds before the peak of the R-wave to 150 milliseconds after the peak of the R-wave. In some examples, at least one of the at least three chest compression protocols may comprise chest compressions synchronized with the peak of the R-wave. The synchronization of the chest compressions may comprise timing of the chest compressions such that a target depth of the chest compressions corresponds with the peak of the R-wave. The synchronization of the chest compressions may comprise timing of the chest compressions such the target depth of the chest compressions occurs prior to the peak of the R-wave. The synchronization of the chest compressions may comprise timing of the chest compressions such the target depth of the chest compressions occurs after the peak of the R-wave. The timing of the chest compressions may comprise reaching the target depth of the chest compressions within 150 milliseconds after the peak of the R-wave.

The system may implement a third range that comprises an intrinsic heart rate between 0 and 40 beats per minute. The system may implement a third chest compression protocol that comprises unsynchronized chest compression. The system may implement a third chest compression protocol that comprises compressions administered according to a predetermined rate and the predetermined rate comprises chest compressions delivered at a rate between 80 and 100 compressions per minute. The system may implement a second range that comprises a heart rate of between 41 beats per minute and 60 beats per minute. The system may implement a second chest compression protocol that comprises compressions synchronized with the at least one identified ECG waveform feature. The system may implement a second chest compression protocol that comprises at least one additional compression interposed between the compressions synchronized with the at least one identified ECG waveform feature. The system may implement a compression protocol that implements multiple compressions interposed between the compressions synchronized with the at least one identified ECG waveform feature. The system may implement a first range that comprises a heart rate of between 61 beats per minute and 120 beats per minute, and wherein the compressions are synchronized with the at least one identified ECG waveform feature.

The system may include at least one first processor configured to process the ECG signals corresponding to the ECG of the heart, and the at least one processor may comprise a second processor configured to control the chest compressor to provide the chest compressions. The system may include at least one processor that comprises a single processor configured to process the ECG signals corresponding to the ECG of the heart, and control the chest compressor to provide the chest compressions. The system may include at least one processor that comprises a first processor and a second processor configured to process the ECG signals corresponding to the ECG of the heart and control the chest compressor to provide the chest compressions. The system may include at least one processor that comprises a first processor configured to process the ECG signals corresponding to the ECG of the heart, and control the chest compressor to provide the chest compressions, and wherein the at least one processor comprises a second processor configured to control the chest compressor to provide the chest compressions. The system may include a defibrillator-monitor, automated external defibrillator, automated chest compressor, wearable defibrillator, or active compression-decompression device. The system may include at least one processor that is configured to administer a fourth chest compression protocol when the intrinsic heart rate of the patient falls within a fourth range, wherein the fourth range comprises an intrinsic heart rate of greater than 120 beats per minute. The system may implement a fourth chest compression protocol that includes the at least one processor configured to adjust the at least one chest compression parameter when the intrinsic heart rate of the patient falls within a fourth range.

The system may utilize at least one chest compression parameter that may include at least one of a compression depth, a compression hold time, a compression release velocity, a compression downstroke time, a compression upstroke time, and a compression force. The system may implement an adjustment of the at least one chest compression parameter comprises a decrease in the depth of chest compressions. The system may implement a fourth range that is further divided into a plurality of sub-ranges. The system may include at least one processor that is configured to adjust at least one chest compression parameter such that a compression cycle is shortened when the intrinsic heart rate of the patient is within a first sub-range, wherein the first sub-range is between 121 beats per minute and 130 beats per minute. The system may include at least one processor that is configured to further adjust at least one chest compression parameter such that a compression cycle is further shortened when the intrinsic heart rate of the patient is within a second sub-range, wherein the second sub-range is between 131 beats per minute and 140 beats per minute. The system may include at least one processor that is configured to further adjust at least one chest compression parameter such that a compression cycle is further shortened when the intrinsic heart rate of the patient is within a third sub-range, wherein the third sub-range is between 141 beats per minute and 150 beats per minute. The system may include at least one processor that is configured to initiate a shock protocol when the intrinsic heart rate of the patient is within a fourth sub-range, wherein the fourth sub-range is greater than 150 beats per minute. The system may implement a shock protocol that analyzes the signals corresponding to the electrocardiogram (ECG) of the heart of the patient to identify shockable rhythms and apply one or more therapeutic shocks in response to identifying shockable rhythms.

The system may utilize at least one chest compression parameter that comprises at least one of a compression depth, a compression hold time, a compression release velocity, a compression downstroke time, a compression upstroke time, and a compression force. The system may include a processor that is configured to pause the chest compressor from administering one or more chest compressions to allow for a check for return of spontaneous circulation (ROSC). The system may implement a check for ROSC (return of spontaneous circulation) that comprises the one or more sensors configured to measure electrical activity of the heart without capturing artifacts created by chest compressions from the chest compressor. The system may implement a check for ROSC (return of spontaneous circulation) that comprises the one or more sensors configured to measure mechanical activity of the heart without capturing artifacts created by chest compressions from the chest compressor. The system may include a processor that increases the set number of chest compressions between pauses in the chest compressor in response to a deterioration of at least one measured parameter of the patient. The system may include a processor that decreases the set number of chest compressions between pauses in the chest compressor in response to an improvement of the at least one measured parameter of the patient.

The system may implement at least one measured parameter of the patient that includes at least one of a blood pressure, an ECG waveform, a measure of CO2 of the patient, an ETCO2 value of the patient, a measure of blood flow of the patient. The system may include at least one processor that is configured to adjust at least one of the first range, the second range, and the second range in response to the intrinsic heart rate of the patient falling within multiple ranges within a predetermined interval of time. The system may implement an adjustment to at least one of the ranges in response to the intrinsic heart rate of the patient falling within multiple comprises increasing the third range. The system may implement an adjustment to the third range that includes altering the third range to comprise a heart rate of between 0 and 45 beats per minute. The system may implement an adjustment to a second range that includes altering the second range to comprise a heart rate of between 45 beats per minute and 60 beats per minute. The system may include a processor that is configured to pause chest compressions in response to a determination that the patient has achieved a return of spontaneous circulation (ROSC). The system may determine ROSC to have occurred in response to at least one of: an organized heart rhythm, a return of consciousness of the patient, determined ETCO2 values at life-sustaining levels, and measured blood pressures at life-sustaining levels.

The system may implement identifying at least one ECG waveform feature that includes at least one of a QRS complex, a leading edge of an R-wave, a peak of an R-wave, and a Q-wave. The system may include a chest compressor that comprises a compression belt and a belt tensioner configured to tighten the compression belt around a thorax of the patient in order to compress the thorax of the patient at a resuscitative rate. The system may include a chest compressor is a piston-based system that comprises a piston, a piston driver, support structures for supporting the piston and piston driver, and a compression pad affixed to the piston. The system may include at least one processor that is coupled to memory are configured to analyze the generated ECG signals to determine a time window relative to the identified at least one ECG waveform feature. The system may identify at least one ECG waveform feature, which includes a peak of an R-wave. The system may implement a time window that is from approximately 125 milliseconds before the peak of the R-wave to 150 milliseconds after the peak of the R-wave. The system may implement a second chest compression protocol that comprises chest compressions synchronized with the peak of the R-wave. The system may synchronize the chest compressions such that a maximum depth of the chest compression corresponds with the peak of the R-wave. The system may synchronize the chest compressions such that a maximum depth of the synchronized occurs prior to the peak of the R-wave. The system may synchronize the chest compressions such that a maximum depth of the chest compression occurs after the peak of the R-wave. The system may synchronize the chest compressions such that a target depth is reached prior to the end of the time window. The system may implement a third range that comprises an intrinsic heart rate between 0 and 45 beats per minute. The system may implement a third range that comprises an intrinsic heart rate between 0 and 50 beats per minute. The system may implement a third range that comprises an intrinsic heart rate between 0 and 35 beats per minute. The system may implement a third range that comprises an intrinsic heart rate between 0 and 30 beats per minute. The system may implement a fourth range that comprises the intrinsic heart rate being greater than 120 beats per minute. The system may adjust one of at least one chest compression parameter such that there may be a proportional relationship between compression depth and the intrinsic heart rate.

The system may adjust one of at least one chest compression parameter such that there may be a step-wise change of the at least one chest compression parameter in response in an increased intrinsic heart rate. The system may implement chest compression parameters that comprise at least one of compression depth, compression hold time, compression release velocity, compression downstroke time, compression upstroke time, compression force, decompression time, decompression force, and decompression velocity. The system may include a processor that is configured to determine the at least one threshold crossing based on the intrinsic heart rate of the patient falling within multiple ranges within a predetermined interval of time. The system may implement a third chest compression protocol that comprises compressions unsynchronized with the at least one identified ECG waveform feature.

The system may implement a check for ROSC that comprises the one or more sensors configured to measure the activity of the heart without capturing artifacts created by chest compressions from the chest compressor. The system may include a processor that increases the set number of chest compressions between pauses in the chest compressor in response to a deterioration of at least one measured parameter of the patient. The system may include a processor that decreases the set number of chest compressions between pauses in the chest compressor in response to an improvement of the at least one measured parameter of the patient. The system may include a processor that pauses the chest compressor during the administration of a plurality of chest compressions to allow for a check for return of spontaneous circulation (ROSC). The system may implement a check for ROSC that comprises the one or more sensors configured to measure the activity of the heart without capturing artifacts created by chest compressions from the chest compressor. The system may implement an embodiment wherein the ROSC is determined based on user input. In some embodiments, ROSC may be determined to have occurred in response to at least one of an organized heart rhythm, a return of consciousness of the patient, determined ETCO2 values at life-sustaining levels, and measured blood pressures at life-sustaining levels. The system may include a chest compressor that pauses after a specified number of chest compressions. In some embodiments, the specified number of chest compressions is user specified.

One example of a system for providing resuscitative chest compressions to a chest of a patient includes: a chest compressor configured to be applied to the chest of the patient and to administer chest compressions to the patient; one or more sensors communicatively coupled to a medical device and configured to sense electrocardiogram (ECG) signals of the patient and to transmit the ECG signals to the medical device; and at least one processor coupled to memory of the medical device. The at least one processor and memory is configured to: receive the ECG signals, determine an intrinsic heart rate of the patient based on the ECG signals, identify at least one ECG waveform feature within the ECG signals, select a chest compression protocol from at least three predetermined chest compression protocols for administration to the patient based on the intrinsic heart rate of the patient, and control the chest compressor based on the selected chest compression protocol. The first chest compression protocol is associated with a first intrinsic heart beat range, the second chest compression protocol is associated with a second intrinsic heart beat range, the third chest compression protocol is associated with a third intrinsic heart beat range, and the fourth chest compression protocol is associated with a fourth intrinsic heart beat range. At least some of the first intrinsic heart beat range, the second intrinsic heart beat range, the third intrinsic heart beat range and the fourth intrinsic heart beat range overlap. Transitioning from one of the at least four predetermined chest compression protocols that is currently being administered to another of the at least four predetermined chest compression protocols occurs when the patient's intrinsic heart beat range changes so as to fall outside of the range associated with the one of the at least four predetermined chest compression protocols that is currently being administered. The protocol that is transitioned to has an associated range that includes the patient's current intrinsic heart beat rate.

In the foregoing example, in one implementation, the intrinsic heart beat range associated with the first chest compression protocol is between approximately 60 and approximately 120 beats per minute. The intrinsic heart beat range associated with the second chest compression protocol is between approximately 40 and approximately 70 beats per minute. The second chest compression protocol includes compressions synchronized with the at least one identified ECG waveform feature with at least one additional compression interposed between the compressions synchronized with the at least one identified ECG waveform feature. The intrinsic heart beat range associated with the third chest compression protocol is between approximately 20 and approximately 50 beats per minute. Third chest compression protocol includes compressions synchronized with the at least one identified ECG waveform feature with at least two additional compressions interposed between the compressions synchronized with the at least one identified ECG waveform feature. The intrinsic heart beat range associated with the fourth chest compression protocol is between approximately 0 and approximately 30 beats per minute. The fourth protocol includes compressions administered according to a predetermined rate. The predetermined rate includes chest compressions delivered at a rate of between approximately 80 and approximately 100 compressions per minute. The at least four predetermined chest compression protocols includes a fifth chest compression protocol. An intrinsic heart beat range associated with the fifth chest compression protocol is between approximately 110 and approximately 150 beats per minute. The fifth chest compression protocol includes compressions synchronized with the at least one identified ECG waveform feature administered at a rate of two for every three intrinsic heart beats. The at least one processor is configured to initiate a shock protocol when the intrinsic heart rate of the patient falls above approximately 150 beats per minute.

BRIEF DESCRIPTION OF THE DRAWINGS

Various aspects of the disclosure are discussed below with reference to the accompanying figures, which are not intended to be drawn to scale. The figures are included to provide an illustration and a further understanding of various examples, and are incorporated in and constitute a part of this specification, but are not intended to limit the scope of the disclosure. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure. A quantity of each component in a particular figure is an example only and other quantities of each, or any, component could be used.

FIGS. 9C and 9D illustrate data from a scientific study showing the effects of chest compressions synchronized at various intervals relative to an R-wave.

DETAILED DESCRIPTION

Figure 1A:
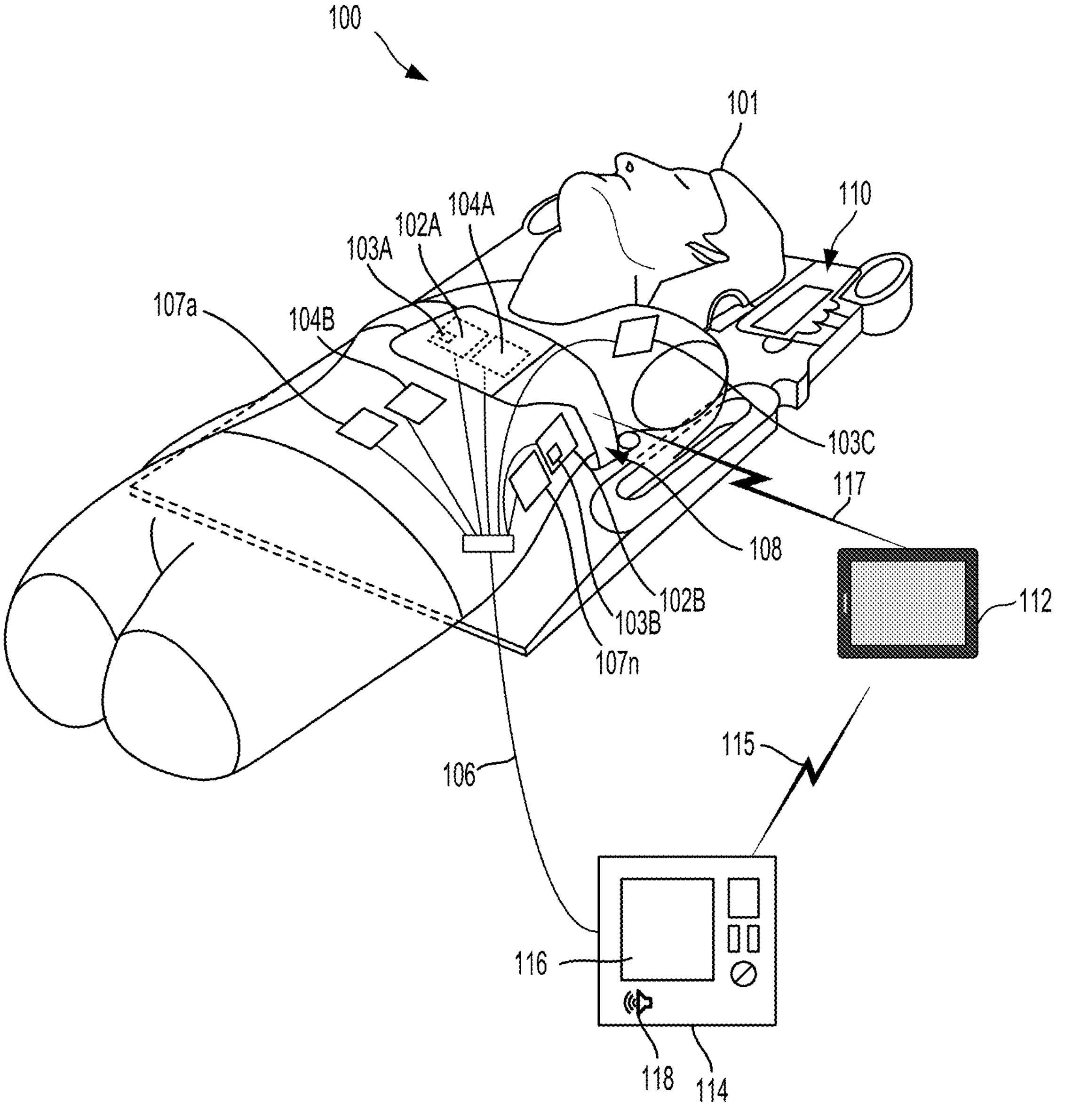
FIG. 1A is a schematic diagram of an illustrative embodiment of a medical system including a patient monitor and an automated chest compression device.

The presently disclosed systems and methods relate to techniques and devices that may be used to increase cardiac output for patient(s) suffering from cardiac ailments, where the patient appears to be lifeless, yet has some electrical heart activity and may further include some residual mechanical heart activity. This condition may be described as unconscious hypotension with organized electrocardiogram (ECG) activity, which may include conditions commonly referred to as pulseless electrical activity (PEA) or pseudo-PEA. A patient suffering from unconscious hypotension with organized ECG activity may have some electrical activity of the heart, but weak or no corresponding mechanical activity. In the case of PEA, the patient's ECG activity may be insufficient to generate heart contractions that give rise to blood flow to peripheral tissues. It is noted that embodiments described herein may include application to patients with weak mechanical heart activity resulting in a small degree of circulation, such as may the case with pseudo-PEA, as well as patients with no appreciable mechanical heart activity resulting in little to no circulation, such as may be the case with PEA. The systems and methods of the present disclosure may increase or create cardiac output in such patients by sensing electrical signals that are indicative of a beating heart and synchronize resuscitative therapies with myocardial heart wall motion.

The systems and methods of the present disclosure provide resuscitative chest compressions to a patient according to an algorithm for selective activation of synchronized chest compressions based on the patient's intrinsic heart rate. In various embodiments, selective activation may occur amongst a plurality of protocols depending on the patient's intrinsic heart rate. As an example of how an algorithm according to certain embodiments of the present disclosure may function, the processor(s) of the chest compression system may determine that the heart rate of the patient falls within a first range (e.g., between approximately 60 and approximately 120 beats per minute), which may trigger the chest compressor to apply chest compressions that are synchronized to the patient's intrinsic heartbeat. If, however, the patient's intrinsic heart rate falls within a second range (e.g., between approximately 40 and approximately 60 beats per minute), then the algorithm may direct the chest compressor to apply chest compression synchronized to the patient's intrinsic heartbeats, but additionally apply additional chest compressions interposed between intrinsic heart beats. If the patient's intrinsic heart rate falls within a lower range subset (e.g., between approximately 20 and approximately 40 beats per minute), then the algorithm or algorithms may direct the chest compressor to apply chest compressions synchronized to the patient's intrinsic heartbeats, with multiple (e.g., two) additional chest compressions interposed between intrinsic heart beats. Furthermore, if the patient's intrinsic heart rate falls within a minimal range (e.g., below approximately 20 beats per minute), then the algorithm may direct the chest compressor to apply conventional chest compressions that are not synchronized to the patient's intrinsic heartbeats, such as in accordance with prescribed guidelines. One benefit of providing the synchronized chest compressions is that the patient receives the benefit of improved blood flow due to the coordination of the chest compressions and patient's intrinsic heartbeat. Adding one or more interposed chest compressions between intrinsic heart beats may provide further benefit in applying additional chest compressions to the patient, for helping to increase blood flow. Where the patient's heart rate is too low or not regular, providing chest compressions will still be beneficial without attempting to synchronize to the heart rate.

In one implementation, a chest compressor is applied to the chest of the patient such that a driving mechanism, (e.g., a motor-driven belt or piston) will administer chest compressions to the patient. Additionally, one or more sensors may be affixed to the patient to measure signals corresponding to the heartbeats of the patient. A medical device, which typically includes a processor, will determine an intrinsic heart rate of the patient. Based on the patient's intrinsic heart rate, the medical device applies a corresponding chest compression protocol optimized for the intrinsic heart rate.

In certain chest compression protocols, the chest compressions may be synchronized to the intrinsic heartbeat of the patient, for inducing clinically beneficial circulation. In other chest compression protocols, one or more additional chest compressions may be interposed in between compressions that are synchronized to the patient's heartbeat (for example, for example in patients that have low heart rates with a periodicity that allows for synchronized chest compressions). In certain other cases, for example where the intrinsic heart rate of the patient 101 may be atypically low (e.g. nearing asystole), then it may be preferable to provide the patient with chest compressions unsynchronized to the heartbeat.

For example, the medical device may administer a first chest compression protocol comprising synchronized chest compressions (e.g., chest compressions that are synchronized with the patient's intrinsic or natural heartbeats when the intrinsic heart rate of the patient falls within a first range (e.g., 61-120 beats per minute). The medical device may administer a second chest compression protocol (comprising synchronized chest compression with an additional interposed compression between intrinsic heartbeats) when the intrinsic heart rate of the patient falls within a second range (e.g., 41-60 beats per minute). The medical device may administer a third chest compression protocol (comprising unsynchronized chest compressions) when the intrinsic heart rate of the patient falls within a third range (e.g., below 40 beats per minute, below 20 beats per minute). Alternatively, the medical device may administer a chest compression protocol involving synchronized chest compressions with multiple interposed (e.g., two) compressions between intrinsic heartbeats when the intrinsic heart rate of the patient falls within a particular range (e.g., between 20-40 beats per minute). The medical device may administer a fourth or different chest compression protocol (e.g., comprising synchronized chest compressions with modified parameters) when the intrinsic heart rate of the patient falls within a fourth range (e.g., above 120 beats per minute). Modified parameters may include one or more of: the compression depth, compression hold time, compression release velocity, compression downstroke time, compression upstroke time, and compression force.

As noted herein, in some embodiments, when the intrinsic heart rate is within a particular range, such as less than 20 beats per minute, a chest compression protocol is administered that includes chest compressions that are not synchronized with intrinsic heart beat motion (e.g., traditional chest compressions applied such as may be applied to a patient in asystole), and when the intrinsic heart rate is within another particular range, such as 21-40 beats per minute, a chest compression protocol is administered that includes synchronized chest compressions as well as two chest compressions interposed between the chest compressions synchronized to the patient's intrinsic heart rate.

In various embodiments described herein, once unconscious hypotension with an organized ECG condition is detected (e.g., in the case of PEA or p-PEA), one or more chest compression protocols may be applied to the patient (e.g., via an automated mechanical chest compressor, via an active compression-decompression device, or via manual chest compressions) according to a timing that results in enhanced forward blood flow from the heart toward peripheral tissues. The timing of such chest compressions may be such that the chest compressions are effectively applied upon detection of the R-wave in a QRS complex. For example, the chest compressions may be initiated after the detection of a QRS complex (e.g., detection on the leading edge of the Q-wave or R-wave) or after determination of a QRS fiducial point. Typically, the chest compression will be initiated during the R-wave and completed or the maximum depth of the compression will be reached within 150 milliseconds or less after the peak of the R-wave.

In some cases, as further described below, the chest compressions may be initiated on or before the peak of the R-wave of the detected QRS complex. As an example, the R-wave may be detected on its initial rising edge (or falling edge, depending on whether the R-wave is above or below the baseline) prior to the actual occurrence of the R-wave peak. A QRS fiducial point is set, from which a delay may be implemented before a chest compression is applied. If such a delay is smaller than the time duration, then the chest compression may be initiated before the R-wave reaches its peak.

On the other hand, a relatively long delay after the peak of the R-wave (e.g., after 150 milliseconds from the peak of the R-wave) may result in a comparatively weak hemodynamic output as compared to chest compressions applied earlier in time. Additionally, synchronized chest compressions may be implemented to avoid the occurrence of chest compressions during periods of diastole, which is the phase of the cardiac cycle during which the heart refills with blood after the emptying done during systole (i.e., when the heart muscle contracts). Applying chest compressions during diastole may result in ineffective perfusion or possibly damage the patient's heart (as detailed in FIG. 10B). Accordingly, applying chest compressions according to synchronized timings discussed herein may result in enhanced hemodynamic output and help avoid potential damage to the patient's heart.

In more detail, at one end of such a hemodynamic spectrum is normal spontaneous circulation. This is where the cardiac activity is normal and left ventricular mechanical and pumping function are normal. Below that level is hypotension, and then compensated shock. In such cases, the blood pressure and the patient's pulse are still palpable and there may be good cardiac output. However, for various reasons, the cardiac output is unable to meet the metabolic demands of the body and homeostasis is at risk. This is evident by parameters such as decreasing urine output and increasing serum lactate, which are markers of inadequate organ function.

The state of uncompensated shock occurs after compensated shock and is a more severe condition. This is a state in which the myocardium and the cardiovascular system are no longer able to provide adequate amounts of blood flow, oxygen, and nutrients to meet the needs of vital organs, and the function of those organs is affected to the extent that they are beginning to become damaged. Blood pressures in this state might be, for example, 70/30 mmHg. systolic over diastolic. Also, urine output may cease, and the patient may become confused because of inadequate cerebral function. Importantly, as shock progresses, the pathways to multi-organ system failure are initiated.

Following classical uncompensated shock is what might be called "extreme shock" which borders on cardiac arrest. In this case, the patient exhibits some residual myocardial function including some left ventricular ejection, but cardiac output is wholly inadequate to meet the needs of vital organs. For example, cardiac output might be less than 1 liter per minute, blood pressure might be 50/20 mmHg, urine output may be minimal or absent, and the patient may be stuporous or comatose. Further, the patient may appear to be near death with significantly impaired cerebral function and stupor bordering on coma. If untreated, extreme shock will result in true cardiac arrest in a timeframe of minutes. Generally, it is not possible to palpate arterial pulses manually in this range, and such patients may be classified as PEA or p-PEA by clinical personnel even though their heart continues to beat, albeit weakly.

Following the state of extreme shock is pulseless electrical activity (PEA) cardiac arrest, which importantly also has a spectrum of conditions and a range of hemodynamics. For example, at its upper end, PEA has both left ventricular mechanical function and cardiac output, but the output is not sufficient enough to be detected at a peripheral radial or femoral pulse. This upper end is often referred to as pseudo-PEA. However, a more appropriate description may be unconscious hypotension with an organized ECG, which describes an unconscious patient, suffering from hypotension, but has an organized ECG.

If an intra-arterial catheter were placed into the patient, the blood pressure might be only 45/25 mmHg, with blood pressure measurable only in major arteries of the chest, neck or groin. A Doppler probe placed over the neck or groin may detect forward blood flow. Blood flow is so profoundly inadequate that the patient will generally appear lifeless and their pupils may dilate and become fixed. Further, they appear to be in cardiac arrest despite the presence of residual pump function and minimal forward blood flow. The high end of PEA dynamics overlaps the low end of "extreme shock." In such cases, the clinical personnel (e.g., rescuers) may not be able to distinguish the difference.

Following the "high end" stage of PEA is electromechanical dissociation (or EMD) with almost absent left ventricular mechanical function. The blood pressure measured by intravascular catheters just above the aortic valve will show aortic pulsations, but the blood pressures measured are on the order of 25/15 mmHG, and there will be almost no associated forward blood flow. Without the application of CPR, oxygen delivered will be essentially absent and irreparable injury to organs such as the brain occurs within minutes.

The final stage of PEA involves an organized electrical rhythm but no left ventricular mechanical function. This is true cardiac arrest. A catheter measuring pressures above the aortic valve will detect no pressure pulse and echocardiography will show no cardiac movement. Further, the cardiac output is non-existent and the patient is in complete global ischemia and cardiac arrest. Without the application of CPR, no blood or oxygen is circulated and irreparable injury to vital organs (e.g., the brain) can occur within minutes.

It is noted that embodiments of the present disclosure can apply to patients in any of various states or conditions, including shock, p-PEA and PEA, for example.

In a typical implementation, the present system is used to detect electrical and mechanical activity (if present) and to synchronize intrinsic cardiac activity with resuscitation techniques, such as those used in CPR (including chest compressions/decompressions and/or ventilation). Hence, the present system may be utilized in any pathophysiologic state including, cardiac arrest, PEA, pseudo-PEA, unconscious hypotension with an organized ECG, through the various stages of shock, and/or in any state in which residual myocardial function with and without mechanical cardiac output exists. By synchronizing chest compressions with the intrinsic heartbeats of the patent, intrinsic cardiac output is augmented, and overall cardiac output and organ profusion may be increased, thereby improving the blood flow of patients with impaired hemodynamics.

Further illustrated by way of example, one situation that often occurs and is particularly challenging for physicians, is when patients are progressing from shock to PEA. In the earlier stages of this process, physicians tend to treat such patients with intravenous medications and possibly controlled ventilation. While drugs such as antibiotics may be administered to patients in states such as septic shock, pressor drugs such as dopamine continue to be a mainstay of treatment. Pressors, however, have generally not been shown to improve the outcome of such patients despite raising the blood pressure. This may be because they improve blood pressure but also raise vital organ oxygen utilization, such that the overall balance between oxygen supply and demand is not improved. Pressor drugs also have significant direct vital organ toxicity.

If, however, these parenteral therapies do not stabilize the patient, then the patient may progress towards more and more extreme states (e.g., cardiac arrest). Many medical practitioners in emergency medicine and critical care continue to be unsure—and the medical literature remains unclear—as to what point a patient whose blood pressure is dropping should begin to receive chest compressions. Indeed, physicians generally do not apply techniques such as external chest compress before subjective loss of vital signs. This is because CPR, and in particular chest compressions, can interfere with intrinsic cardiac function and in particular cardiac filling if applied in an unsynchronized manner. For instance, a patient whose blood pressure is 60/40 who begins to receive chest compressions out of synchronization with heart function could rapidly progress into full cardiac arrest. More specifically, in performing CPR without synchronization, application of the compression phase when the left ventricle is in a state in which it would normally fill may significantly decrease cardiac output on the next ejection secondary to the Frank Starling Law of the heart. Hence, by detecting myocardial mechanical function and/or electrical activity, chest compressions can be synchronized with the ejection phase so that patients in shock may be treated without exacerbating their condition and causing the patient to progress further toward cardiac arrest.

Hence, the issue as to when chest compressions should begin when a patient is progressing through the stages of shock may be addressed by synchronizing chest compressions, and possibly other mechanical adjuncts, with the ejection and relaxation phases, so that the clinician may be more confident that chest compressions are assisting and not interfering with residual circulatory function. In this way, the clinician does not need to be as concerned with the question as to when to begin chest compressions. In this manner, the present system may allow the use of external mechanical adjuncts in the treatment of any form of shock in a manner similar to the methods by which intra-aortic balloon counterpulsation has been applied in cardiogenic shock. The present system may thus allow the application of such adjuncts in the pre-hospital, and Emergency Department environments.

Another advantage of using synchronization is that it may be performed as an adjunct to therapies directed at the cause of the shock, such as antibiotics or thrombolysis, enhancing vital organ perfusion while these therapies are being administered. Indeed, improved hemodynamics may not only stave off organ injury, but it may also improve the efficacy of parenteral therapies. Further, synchronized chest compressions are unlikely to have significant organ toxicity, unlike pressor drugs.

As described above, one particular application of the present system is in connection with those suffering from pulseless electrical activity (PEA). PEA is one of the three broad-types of cardiac arrest, the other two being ventricular fibrillation and asystole. PEA is also referred to as electro-mechanical disassociation (EMD). PEA has been described as "the presence of organized electrical activity on the electrocardiogram but without palpable pulses." Rosen P, Baker F J, Barkin R M, Braen G R, Dailey R H, Levy R C. Emergency Medicine Concepts and Clinical Practice. 2nd ed. St Louis: C V Mosby, 1988. Unlike ventricular fibrillation, which can be specifically reversed with electrical countershock, PEA does not have a specific countermeasure. This may explain the traditionally worse outcome of patients in PEA compared to ventricular fibrillation. Unfortunately, the incidence of PEA is increasing, possibly because early risk modification is changing the natural history of cardiovascular disease. It is now reported by some authorities that the majority of patients in cardiac arrest are in PEA at the time of EMS arrival. Additionally, a significant fraction of patients that are shocked out of ventricular fibrillation, or resuscitated from asystole, will experience PEA at some point during their resuscitation. The combination of these circumstances means that a large majority of patients receiving advanced life support for the treatment of cardiac arrest will have PEA at some time during resuscitation. Hence, now or in the near future, PEA may supersede classical ventricular fibrillation in importance.

Many patients suffering from unconscious hypotension with an organized ECG may have some residual cardiac mechanical activity, and many have detectable blood pressures. This condition may be also referred to as pseudo-EMD, or pseudo-PEA. In such cases, the patient may appear lifeless and without a pulse. However, there often yet remains some degree of residual left ventricular function. Hence, one important feature of the present system is to sense when the patient still has some myocardial function and then to synchronize phasic resuscitation therapies, especially compression of the chest, with the heart's residual mechanical function. In this way, the compression phase of CPR may occur during the ejection phase, and the relaxation phase can allow elastic recoil of the chest—with associated decreases in intrathoracic pressure when the left ventricle is trying to fill. In this way, synchronizing phasic resuscitative therapies with residual ventricular ejection and filling may improve hemodynamics, the rate of a return to spontaneous circulation (ROSC), and long term survival.

The present system may incorporate various non-invasive sensing technologies to acquire real-time data describing the pattern of myocardial wall and or valve motion so as to allow synchronization of chest compressions and other therapies. If, however, invasive indicators of hemodynamics, such as intra-arterial pressure or flow monitors, are present, then the present system may act as an interface between those inputs and phasic resuscitative therapies as exemplifies by external chest compression. To apply proper synchronization between the forces of external devices, on or around the chest or body, and the ejection and filling phases of residual left ventricular function, a variety of devices may be used. The decision that residual myocardial activity exists may be made from a logic circuit with inputs from multiple sensing modalities. The present system may utilize sensing technology to collect the data on myocardial wall function, myocardial valve motion, blood flow in vascular structures, vital organ oxygen or energy status, or exhaled pulmonary gas, and this data may be passed through logic circuits and a controlling output signal passed to the devices that deliver therapies. Because the pattern of mechanical residual wall function may be variable over time, the present system may be designed to promptly identify the residual function and to vary therapeutics based on feedback to a logic circuit. Also, the synchronizing of external chest compressions may be used with other techniques, such as with abdominal counter pulsations, phasic limb compression, ventilation, and electrical stimulation, among others, to augment cardiac ejection and filling. In this way, the patient may be stabilized to allow sufficient time for primary therapies, such as thrombolysis, to be effective.

A wide variety of equipment and devices may be used to provide chest compressions. For example, various types of automated compression systems may be used to compress the chest. These include systems, such as the AutoPulse Resuscitation System, by ZOLL Medical Corporation, the Thumper manufactured by Michigan Instruments, or the LUCAS device, to list a few examples. Further, the present system is not limited to automated compression systems, but may be used with manual techniques as well. For example, the present system may be used to provide an audio and/or visual signals to indicate to a rescuer as to when to manually apply chest compressions to the patient.

In addition to synchronizing chest compressions with residual heart function, the present system may also be used to synchronize ventilations with residual heart function. For example, inspiration and expiration may be synchronized with residual myocardial function so as to increase cardiac output. For instance, inspiration may be synchronized to systole and expiration with diastole. To apply ventilations, the present system may use a traditional ventilator or ventilations may be provided manually, such as by using a ventilator bag. In the latter case, an audio and/or visual signal may be provided to the rescuer as to when to apply proper ventilations.

With both chest compressions and ventilations, the timing, frequency and/or duration may be varied depending on the particular treatment. For example, chest compressions may occur during the entire systole phase, or only during a portion of it. Further, chest compressions may occur every systole phase or during only certain systole phases. A similar scenario may occur with ventilations. The controller may use one or more sensory inputs, and a logic circuit utilizing an indicator or indicators of efficacy, to optimize the effect of synchronization on hemodynamics.

The system disclosed herein may be utilized with any therapy that may benefit from synchronization with residual myocardial mechanical function in apparently lifeless patients. Chest compression and decompression, abdominal counter-pulsation, ventilation, phasic limb-compression, myocardial electrical stimulation, intravascular fluid shifting, intravascular or intra-pericardial balloon inflation-deflation, application of transthoracic electromagnetic irradiation, among others. The controller logic circuit may vary the pattern (or protocol) of synchronization among multiple therapies so as to determine the optimal pattern with respect to increasing hemodynamics.

Myocardial electrical stimulation is, for example, external electrical shocks delivered through metal paddles or electrodes applied to the chest, or electrical signals applied directly to the heart from an internal pacemaker modified to synchronize myocardial electrical stimulations to, for example, myocardial wall function or detected pulsatile blood flow. Embodiments described herein may be used in accordance with the disclosure provided in U.S. Pat. No. 9,833,378, entitled "NON-INVASIVE DEVICE FOR SYNCHRONIZING CHEST COMPRESSION AND VENTILATION PARAMETERS TO RESIDUAL MYOCARDIAL ACTIVITY DURING CARDIOPULMONARY RESUSCITATION," which is hereby incorporated by reference herein in its entirety.

FIG. 1A is a schematic diagram of an exemplary embodiment of a medical system 100 including a medical device 114 (e.g., a patient monitor, defibrillator-monitor, or defibrillator) and an automated chest compressor (chest compressor) 108. In this embodiment, the medical device 114 receives and processes signals obtained from electrocardiogram sensors/electrodes 103A, 103B (ECG sensors), which are attached to a patient 101. Optionally, additional ECG sensors 103C to 103*n* may also be attached to other body parts of the patient 101 such as the patient's arms, back, and legs. By placing electrodes away from the chest of the patient, artifacts from chest compressions may be minimized. Hemodynamic sensors 104A to 104*n* (hereinafter, collectively referred to as hemodynamic sensor(s) 104) obtain information related to blood circulation within the patient 101. Similarly, one or more hemodynamic sensors may be placed on various parts of the patient's body. The hemodynamic sensors may measure one or more of a blood pressure, CO2 of the patient, SPO2 of the patient, an ETCO2 value, or other measure of blood flow of the patient.

The additional ECG sensors 103C to 103*n* are typically not tethered or connected to the band/belt of the automated chest compressor 108 so as to avoid creating artifacts in the measured ECG signals that might hinder detections of QRS complexes or the determination of the QRS fiducial point (discussed in detail below). In general, the ECG sensors 103A to 103*n* measure the electrical activity of the heart by measuring electrical charges associated with the depolarizing and repolarizing during each heartbeat of the patient 101. The hemodynamic sensors 104 are attached to the patient 101 in order to measure hemodynamic activity (e.g., blood flow at regions to which the hemodynamic sensors are attached). Taking inputs together from the ECG sensors 103 *a* to 103*n* and the hemodynamic sensor 104, at least one processor (e.g., reference numeral 123 in FIG. 2) may be configured to determine whether the patient 101 is suffering from a cardiac condition (e.g., asystole, unconscious hypotension with an organized ECG, p-PEA, PEA, ventricular fibrillation, and ventricular tachycardia).

The medical device 114 may be, for example, but not limited to, one or more of, a patient monitor, a defibrillator, a mechanical chest compression device (e.g., an automated chest compression device, a belt-based chest compression device, a piston-based chest compression device, a hand-held chest compression device for mechanically assisted chest compressions, an active compression-decompression device, or combinations thereof), a ventilator, an intravenous cooling device, and/or combinations thereof. The medical device 114 may be a wearable device. The medical device 114 may include or be coupled to a patient monitor. The ventilator may be a mechanical ventilator. The mechanical ventilator may be a portable, battery-powered ventilator. The intravenous cooling device may deliver cooling therapy and/or may sense a patient's temperature. The medical device 114 may provide, for example, but not limited to, one or more of electrical therapy (e.g., defibrillation, cardiac pacing, synchronized cardioversion, diaphragmatic stimulation, phrenic nerve stimulation, etc.), ventilation therapy, therapeutic cooling, temperature management therapy, invasive hemodynamic support therapy (e.g., extracorporeal membrane oxygenation (ECMO)), and/or combinations thereof.

As illustrated, the medical device 114 incorporates and/or couples (e.g., mechanically, electrically, and/or communicatively) to one or more sensors. The sensors obtain patient parameters. The sensors may include, for example, but not limited to, cardiac sensing electrodes, chest compression sensor(s), ventilation sensor(s), and/or one or more sensors capable of providing signals indicative of one or more of vital sign(s), electrocardiogram (ECG), blood pressure (e.g., invasive blood pressure (IBP), non-invasive blood pressure (NIBP)), heart rate, pulse oxygen level, respiration rate, heart sounds, lung sounds, respiration sounds, end tidal CO2, saturation of muscle oxygen (SMO2), arterial oxygen saturation (SpO2), cerebral blood flow, electroencephalogram (EEG) signals, brain oxygen level, tissue pH, tissue oxygenation, tissue fluid levels, and/or one or more sensors capable of providing signals indicative of one or more parameters determined via ultrasound, near-infrared reflectance spectroscopy, pneumography, cardiography, ocular impedance, spirometry, tonometry, plethysmography, eye tracking, chest compression parameters (e.g., compression depth, compression rate, compression release, release velocity, distance of active release for active compression-decompression, etc.), ventilation parameters, respiratory parameters, drug delivery parameters, fluid delivery parameters, transthoracic impedance, blood sampling, venous pressure monitoring (e.g., CVP), temperature, pulse oximetry, non-invasive hemoglobin parameters, and/or combinations thereof. In various implementations, the one or more sensors may also provide therapy.

In a typical implementation, one or more rescuers (e.g., reference numeral 105 in FIG. 2) provide treatment and/or care to the patient 101. The treatment may include, for example, assessing the patient's condition, treatment of wounds, administration of medications, performance of intubation for ventilation purposes, or performance of CPR, to list a few examples. In the illustrated example, the patient 101 is positioned on the support and housing 110 of the automated chest compressor 108, such as the AutoPulse Resuscitation System provided by ZOLL Medical Corporation of Chelmsford, Mass. The AutoPulse Resuscitation System is a battery powered, belt-based, automated chest compressor capable of providing high-quality automated CPR to victims of cardiac arrest. In operation, the belt is positioned around the thorax of the patient, and through automated constriction of the belt, the AutoPulse Resuscitation System provides chest compressions to the patient 101 by constriction of the belt around the patient thorax in a manner that improves blood flow to the heart, brain, and other body extremities.

In one example, the medical device 114 is a defibrillator or monitor-defibrillator capable of providing ECG shock analysis and defibrillation to the patient. Examples of such monitor-defibrillators include R-SERIES or X-SERIES manufactured by ZOLL Medical Corporation of Chelmsford, Mass. Likewise, other examples of medical device 114 could include the M-SERIES, E-SERIES, or Propaq MD, also manufactured by ZOLL Medical Corporation of Chelmsford, Mass. In yet another alternative embodiment, the medical device 114 may also be an automated external defibrillator (AED) such as the AED PLUS or AED PRO, both of which are manufactured by ZOLL Medical Corporation.

Electrode pads 102A, 102B, which include the electrocardiogram (ECG) sensors 103A, 103B, respectively are attached to the patient 101. Proper placement of the electrode pads 102A, 102B on the patient 101 is important to ensure the effectiveness of the therapy. In adults, one electrode pad is typically placed on the patient's right chest above their right nipple and the second electrode pad is typically placed on the left lateral side of the patient opposite placement of the first electrode pad. In pediatric patients, who are comparatively lighter in weight than adults, one electrode pad is typically placed on the front right chest wall and the second electrode pad is typically placed on the back of the thorax.

In a typical implementation, the medical device 114 further includes an input/output interface such as a touch-screen visual display 116 that provides a visual display of the patient parameters, feedback related to resuscitation, and/or enables user input by the rescuer(s). Additionally, the medical device 114 may include one or more speakers 118 to provide audible feedback (e.g. alarms, prompts, alerts). The medical device 114 may include other methods of inputs such as programmable soft keys, buttons, or dials, for example. In yet another alternative embodiment, the medical device 114 may include a microphone to receive voice commands from the rescuer.

In various implementations, the one or more hemodynamic sensors 104 are communicatively coupled to the medical device 114 and placed on the patient. The hemodynamic sensor(s) may provide a measure of the flow of blood within tissues of the patient's body. In an example in which the medical device is the R-SERIES or X-SERIES manufactured by ZOLL Medical Corporation, the hemodynamic sensor 104 may be an invasive blood pressure (IBP) monitor, which may be inserted into one or more of the patient's arteries (e.g., the Aorta, Brachial Artery, Femoral Artery, Pulmonary Artery, or Radial Artery) to provide a direct measurement of arterial pressure of the patient. Such invasive sensors allow direct and continuous monitoring of the patient's blood pressure beat-by-beat, and this method enables precise measurements of blood pressure, even at relatively low blood pressures.

A dynamic pressure sensor may be used to detect pulsatile flow by sensing the oxygen content in a peripheral vein. Similarly, a pulse oximetry sensor may also be used to detect the oxygen content in a blood vessel in, for example, the toes, fingers or ear lobes. The oxygen content is directly related to the flow of blood and may be used to determine when to initiate and terminate CPR and mechanical or electrical cardiac stimulation. For example, if the pulse oximetry sensor detects pulsatile flow and an oxygen content above a threshold, the system may reduce the force of chest compressions applied by the automated chest compression or terminate chest compressions. Similarly, if the pulse oximetry sensor detects no pulsatile flow or an oxygen level falling below a threshold, the system may initiate manual chest compressor or electrical cardiac stimulation. The system may adjust various parameters of phasic therapies based on trends in the sensed oxygen status. While the pulse oximeter's primary purpose is to measure oxygen saturation of the patient, pulse oximeters are often also able to determine heart rate and provide an indication of perfusion through the body via such measurements.

To sense myocardial wall function, a variety of noninvasive devices and technologies may be used. For example, Doppler ultrasonography may be implemented. Doppler ultrasound uses the Doppler shift of ultrasonic waves produced from a transducer and reflected from body tissues to quantify the blood flow in peripheral vessels. This may be applied with the transducer positioned on the neck for providing a measure of carotid flow, the groin for measuring femoral flow, or a transthoracic or intraesophageal transducer for measuring aortic flow. A Doppler probe may also be placed at the cardiac point of a maximum impulse to detect movement of blood within the myocardium. An array of Doppler probes may be used to determine the vector of residual myocardial mechanical function and align chest compression and relation with that vector.

The data regarding pulses in peripheral blood vessels may be utilized to estimate residual myocardial mechanical function, such as the cardiac ejection phase, based on stored information regarding the delay between the myocardial mechanical function and pulse pressure or pulsatile flow in the peripheral blood vessel.

A further sensing technique that may be used is plethysmography. Plethysmography may be applied by measuring changes in the transthoracic AC electrical impedance with heart motion. A further technique that may be used is phonocardiography, which records the acoustical energy detected by a stethoscope over the heart. Still, a further technique that may be used is echocardiography. With echocardiography, ultrasound imaging of the heart, left ventricular ejection can be quantified. In some cases, echocardiograph detection of heart function may be combined with ECG. Also, sensitivity may be improved through the use of intravenously injected microbubbles or other ultrasound enhancing technologies.

It may be optimal to combine a number of these detection systems so as to increase the sensitivity and specificity of detecting residual myocardial mechanical function. Additionally, it may be optimal to incorporate a logic circuit which compares combinations of sensing technologies to an indicator of actual cardiac output, such as end-tidal carbon dioxide or aortic flow. In this manner, the present system could determine which combination of sensing technologies are most predictive of improvements derived from synchronization.

Additionally, the logic circuit of the present system might be capable of varying the synchronized therapeutics against indicators of actual cardiac output so as to determine which pattern of synchronized therapy is most effective. It may vary synchronization within one therapeutic device or multiple therapeutic devices so as to identify the optimal pattern.

In some embodiment, it may be optimal to combine a number of these detection systems so as to increase the sensitivity and specificity of detecting residual myocardial mechanical function. Additionally, it may be optimal for the processor (123 in FIG. 2) to implement software and/or the logic circuit to compare combinations of sensing technologies to determine which combination is most sensitive, accurate, or predictive of improvements derived from synchronization of chest compressions.

In yet another embodiment, a radio frequency (RF) sensor may be used to measure the patient's blood pressure. In operation, a radio frequency wave is directed toward a patient's artery and part of the reflected radio waves are received by a detector. The detected energy is then processed using one or more signal processing algorithms to extract information directed to the type, location, size, and relative movement of the tissues and organs and consequently blood flow. One example is of an RF sensor is the μCor non-invasive fluid status monitor by Kyma Medical Technologies of Tel Aviv, Israel or the LifeWave Cardio Connect sensor by Lifewave Biomedical, Inc. of Los Altos, CA.

In still another alternative example, evidence of hemodynamic flow (e.g., patient's pulse) may be determined and inputted by the rescuer. For example, the rescuer may check the carotid artery in the patient's neck or the radial artery in the patient wrist or may use a stethoscope to listen for sounds of the heart and/or blood vessels that are indicative of hemodynamic flow. In this embodiment, the rescuer would manually input the hemodynamic status of the patient into the medical device 114 via an input, such as a touchscreen interface displayed on the display 116 of the medical device 114.

In the illustrated embodiment, the ECG and hemodynamic sensor(s) are connected to the medical device 114 via a wired connection 106. In an alternative embodiment, however, the connection may be wireless (e.g., wireless communication 115 or 117). Likewise, in some embodiments, the automated chest compressor 108 and/or the ECG sensors 103A to 103*n* and hemodynamic sensors 104 may be able to communicate wirelessly with an external computing device 112. Such wireless communication may be accomplished via Bluetooth, BLE (i.e., Bluetooth Low Energy), near field communication (NFC), 3G/4G/5G wireless networks, or Wi-Fi networks, to list a few examples.

The external computing device 112 may be a tablet or other mobile computing devices such as smartphones, wearable devices (e.g., smart watches or smart glasses), laptop computers, personal digital assistants. Additionally, the external computing device 112 may include a touchscreen interface, as illustrated, or include alternative means of input such as a keyboard and mouse. In yet another embodiment, the external computing device may utilize voice commands as input. While the illustrated example shows the external computing device 112 as being at the scene with the patient 101, the external computing device may be a personal computer and located remotely and operated by a remote user (e.g., a doctor at a hospital).

Figure 1B:
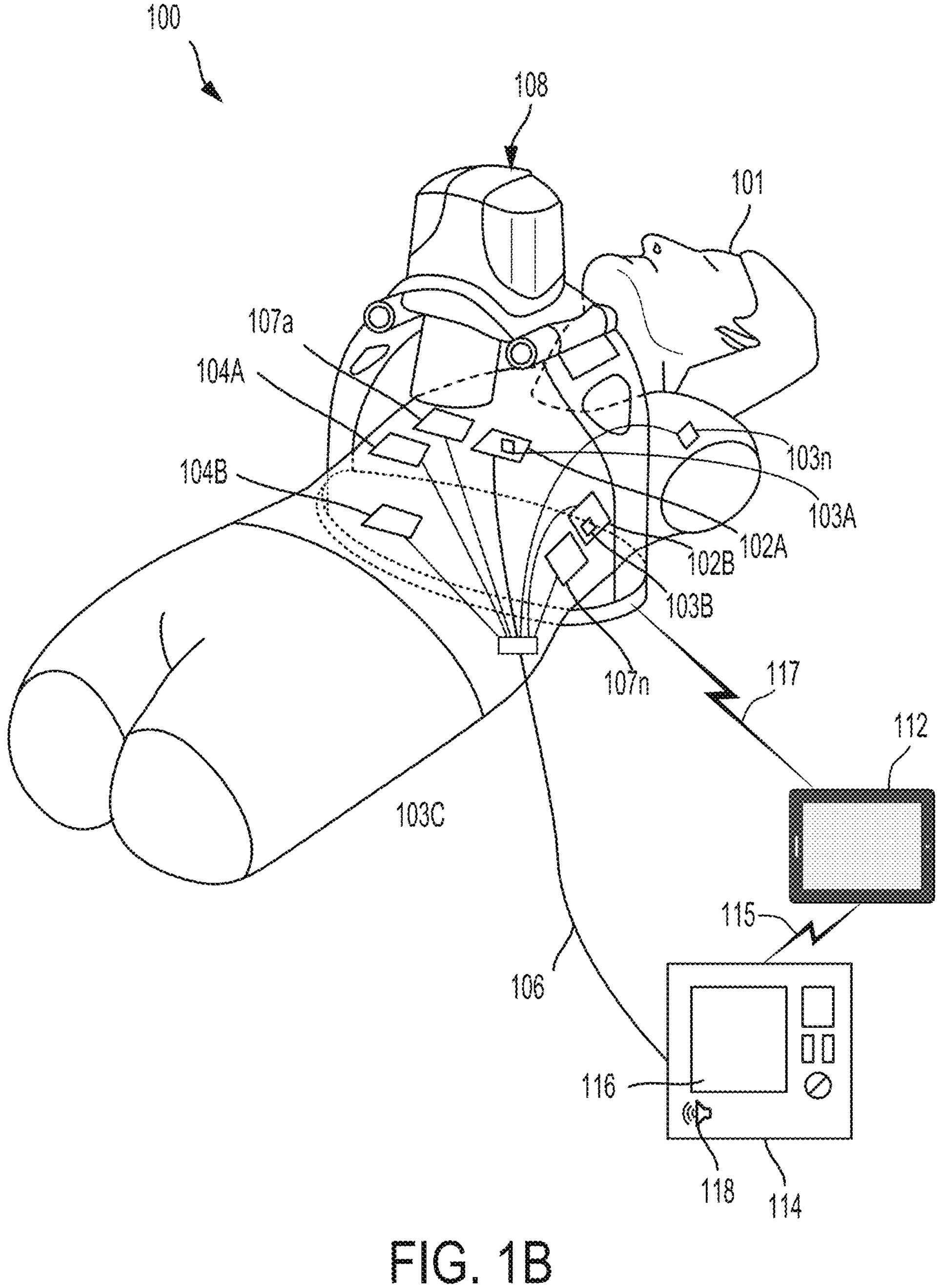
FIG. 1B is a schematic diagram of an illustrative embodiment of a medical system including a medical device and an alternative automated chest compression device.

FIG. 1B is a schematic diagram of a medical system 100 including a medical device 114 and a piston-based automated chest compressor 108. In general, the system of FIG. 1B is similar to the embodiment described with respect to FIG. 1A. In this embodiment, however, the automated chest compressor 108 is a piston-based chest compressor such as the Lucas chest compression device stem by Physio-Control Corporation of Redmond, WA With the LUCAS system, the piston is rigidly locked in place relative to the back plate via rigid legs. A piston and piston driving mechanism are attached to support arms. In operation, the piston is installed such that the piston contacts the chest of the patient and compressions are generated via the vertical motion of the piston which forces compression of the patient's chest.

Figure 2:
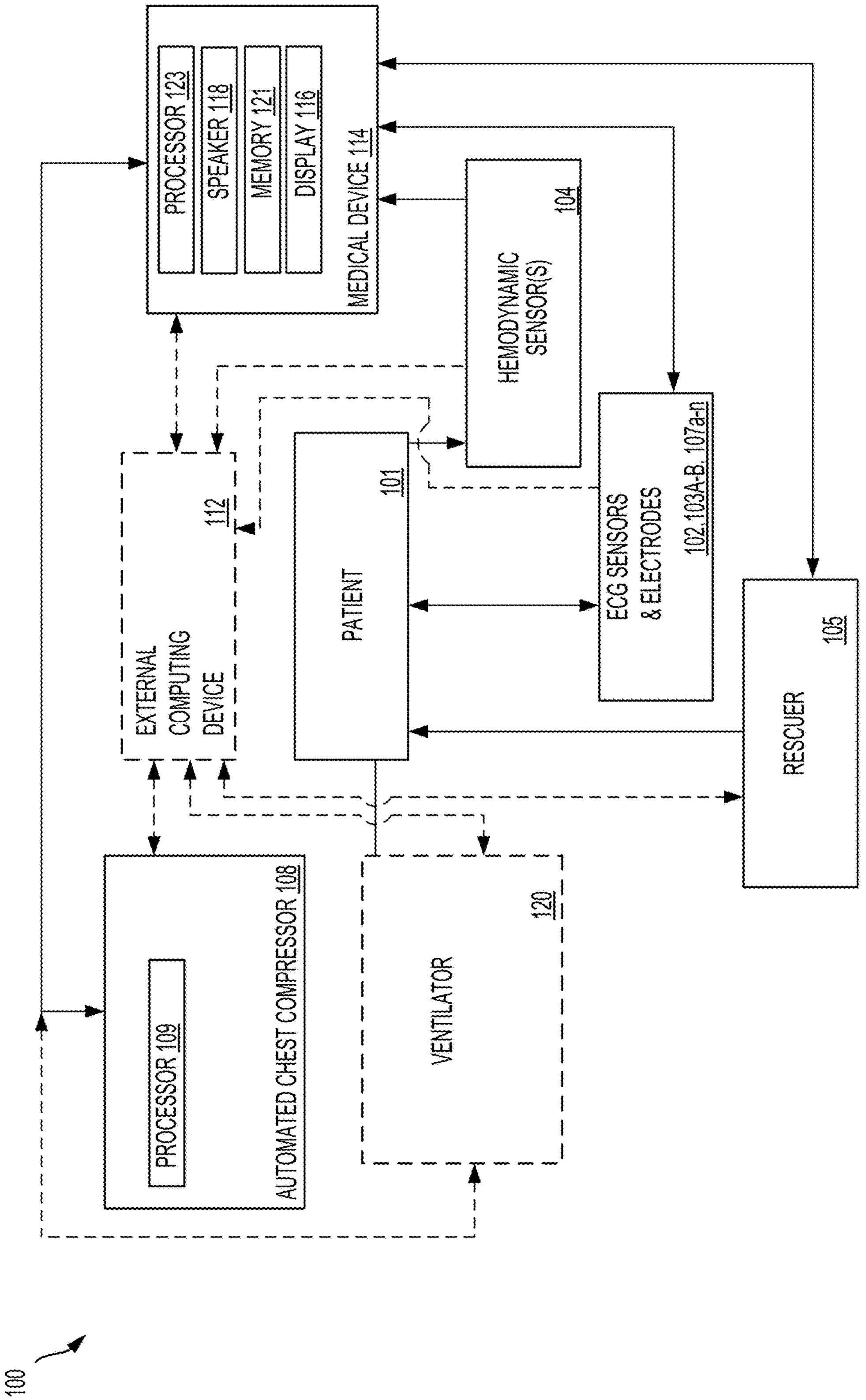
FIG. 2 is a block diagram illustrating the relationship between the components of the systems described in FIGS. 1A and 1B, according to one embodiment.

FIG. 2 is a block diagram illustrating the relationship between the components of the medical systems 100 described in FIGS. 1A and 1B, according to one embodiment. This figure also illustrates a rescuer 105, an optional ventilator 120, and the components of the medical device 114. These components include one or more processors 123 and memory 121, a speaker 118, and a display 116. In one embodiment, the at least one processor 123 comprises a first processor configured to process the ECG signals corresponding to the ECG of the heart and a second processor configured to control the chest compressor to provide the chest compressions to the patient 101. In another embodiment, the at least one processor 123 comprises a single processor configured to process the ECG signals corresponding to the ECG of the heart and control the chest compressor to provide the chest compressions to the patient. In yet another embodiment, the at least one processor 123 comprises a first processor and a second processor configured to process the ECG signals corresponding to the ECG of the heart and control the chest compressor to provide the chest compressions to the patient 101. In still another embodiment, the at least one processor 123 comprises a first processor configured to process the ECG signals corresponding to the ECG of the heart and control the chest compressor to provide the chest compressions. Additionally, the at least one processor 123 comprises a second processor configured to control the chest compressor to provide the chest compressions to the patient.

In one example the optional ventilator 120 may be a portable mechanical ventilator that provides mechanical ventilation to a patient. An example may include the EMV+, AEV, Eagle II, and/or Eagle II MRI, all of which are manufactured by ZOLL Medical Corporation. Alternatively, the ventilator could be a BVM (bag-valve-mask) device that requires manual operation of the bag to provide ventilations to the patient 101.

Exemplary components of the medical device 114 include one or more processors 123, memory 121, which may include hard disk drive (either solid state magnetic based), RAM, or flash memory for example. The display 116 may be a touch screen interface that enables user input to be entered on the display 116. Alternative embodiments may use other display technology, such as light emitting diodes (LED), liquid crystal display (LCD) or organic light emitting diodes (flexible OLED), to list a few examples.

Additionally, the medical device 114 may further include one or more speakers 118 capable of providing audible feedback. For example, the speaker 118 may provide an alarm in response to a deteriorating heartbeat, deteriorating ventilations, or deteriorating end tidal CO2. The speaker may also provide verbal instructions for the rescuer 105 to carry out one or more shock therapy protocols.

Figure 3A:
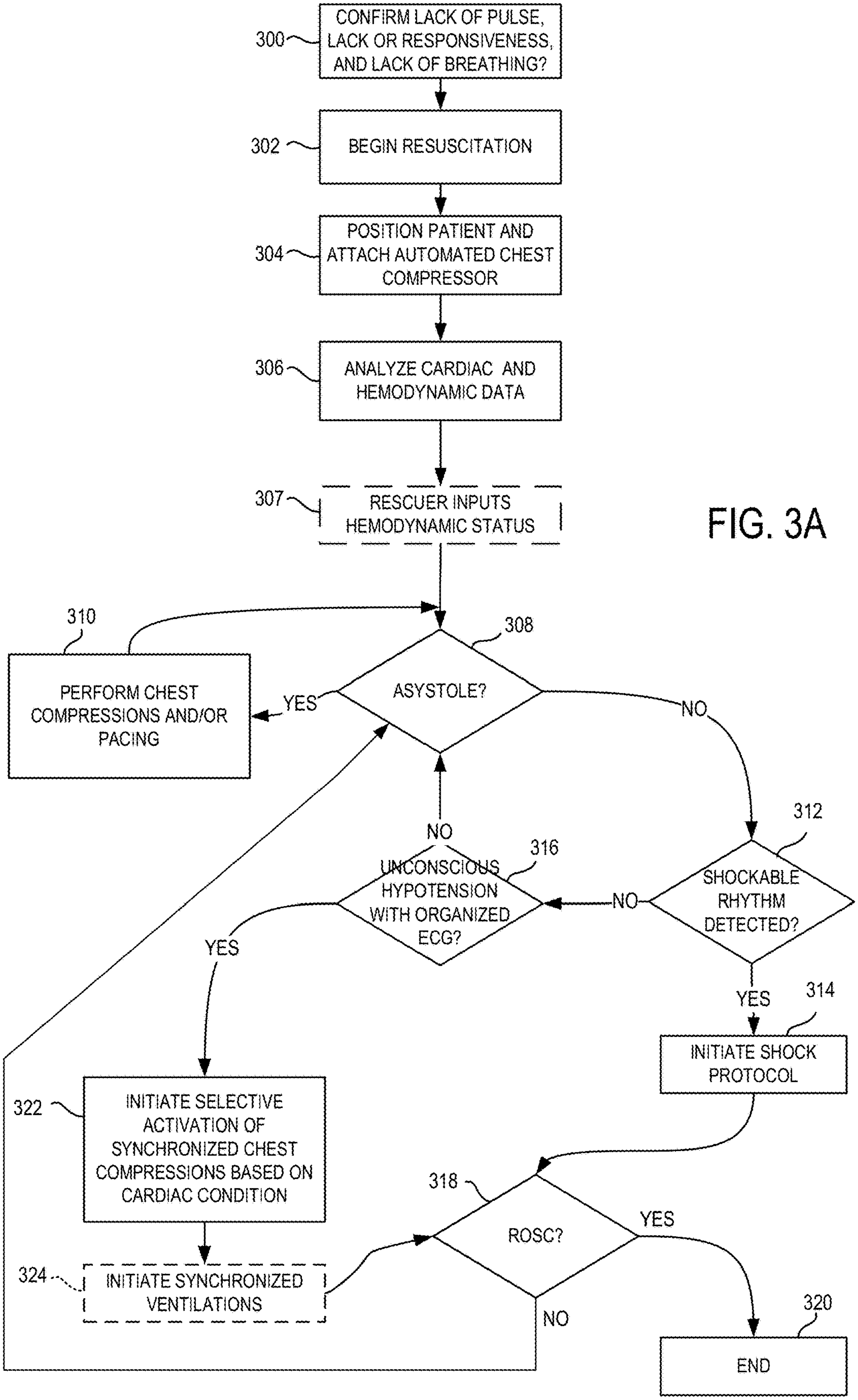
FIG. 3A is a flow chart illustrating steps for implementing the medical system of the present disclosure, according to one embodiment.

FIG. 3A is a flow chart illustrating steps for implementing an exemplary method of treating a patient by the medical system 100 comprising administering chest compressions that are synchronized with the intrinsic cardiac electrical activity (heartbeat) of the patient. Part or all of such a treatment method may be implemented in one or more algorithms to aid a rescuer in providing selective activation of synchronized chest compressions.

In the first step 300, the rescuer 105 checks the patient and confirms a lack of pulse, responsiveness, and breathing. This step may include the rescuer's initial assessment of the patient's condition as well as the process of manually examining the patient to identify any injuries or other symptoms. In the next step 302, the rescuer 105 begins an exemplary resuscitation protocol, an example of which is illustratively provided below in the following steps.

Next, in step 304, the rescuer 105 positions the patient 101 so that an automated chest compressor 108 may be properly coupled to the patient 101. This step typically involves placing the patient 101 on a platform or support structure of the automated chest compressor. In the case of a belt-based chest compression device, the rescuer places the straps (or belts) of the automated chest compressor 108 around the chest of the patient 101. In examples of the treatment method that utilize a piston-based automated chest compressor, the patient is placed on a backboard and the piston and piston driving mechanism are positioned so as to apply compressions to the patient's sternum.

Additionally, the rescuer 105 also attaches electrode pads 102A, 102B, which include ECG sensors 103A, 103B, and one or more hemodynamic sensors 104 to the patient. These ECG sensors 103A, 103B enable the medical device 114 to acquire and analyze cardiac data in the form of electrical activity (e.g., ECG waveforms/ECG data) and the hemodynamic sensors 104 provide an indication of blood flow throughout the patient's body. In a typical implementation, the medical device 114 may perform a sensor validation procedure to ensure that the ECG 103A to 103*n* and hemodynamic sensors 104 are operating properly and that the received cardiac and hemodynamic data is accurate.

The processor 123 of the medical device 114 then analyzes the cardiac and hemodynamic data generated by the ECG sensors 103A, 103B and hemodynamic sensor 104, respectively, in step 306. This analysis typically includes a calculation of the patient's intrinsic electrical and mechanical activity (e.g., the patient's blood pressure and/or intrinsic heart rate, if present). A typical heart rate for a healthy adult is usually in the range of 60-80 beats per minute.

In certain examples, in step 307 the rescuer 105 may input the hemodynamic status of the patient. The option to allow the rescuer to input patient hemodynamic status at this step may be desirable when the system cannot obtain hemodynamic data, for example, when a hemodynamic sensor is not available or not working properly (e.g., failed validation). In such exemplary methods and systems, the rescuer 105 may manually check for a pulse and then enter the information into the medical device 114. In one example, the display 116 of the medical device 114 is a touchscreen that displays the information and is configured to allow the rescuer to interactive with the touchscreen of the display to manipulate and/or analyze the displayed information. Additionally, the medical device 114 may implement one or more soft keys that enable user input. For example, a plurality of soft keys or buttons are positioned adjacent to the display 116 of the medical device 114 and the first key or button is pressed if the rescuer has detected a heartbeat of the patient and the second button is pressed if the rescuer has not detected a heartbeat of the patient 101.

In some embodiments, the user input of the hemodynamic status may act as an override of any determination made by the medical device 114. In embodiments, the rescuer 105 may want to provide the input of hemodynamic flow directly to the medical device 114. For example, the hemodynamic sensor(s) may be malfunctioning or may be taking a longer than desirable time to provide conclusive hemodynamic information to the medical device 114. In such cases, the rescuer can provide a direct manual input of the state of the hemodynamics of the patient 101. In another embodiment, the rescuer 105 may not utilize a medical system 100 with hemodynamic sensors. In such a scenario, the rescuer 105 inputs the hemodynamic status after determining the patient's hemodynamic status (e.g., check for a pulse at one or more arteries).

Next, in step 308, the processor 123 determines whether the patient is in asystole (i.e., the absence of any cardiac activity). If the patient is in asystole, then the medical device 114 transmits a signal to the automated chest compressor 108 to immediately begin delivering chest compressions and the medical device 114 may also initiate pacing in step 310. While the embodiment is described with respect to an automated chest compressor 108, the chest compressions could be provided manually by the rescuer. In such a case, the medical device 114 displays one or more prompts that provide an indication of when to provide the chest compressions. Likewise, the medical device 114 may further provide visual and/or audible feedback to the rescuer to provide step-by-step instructions on how to adjust the chest compressions (e.g., faster, slower, deeper, shallower) to improve the quality of the chest compressions.

As will be detailed below, the chest compressor 108 utilizes an algorithm for the selective activation of synchronized chest compressions to selectively provide one or more chest compression protocols based on the patient's intrinsic heart rate. According to the treatment method disclosed herein, when the patient is in asystole, such as when no electrical or mechanical activity is present, the rescuer delivers chest compressions according to a standard chest compression protocol, such as a protocol according to the American Heart Association's current CPR guidelines.

Returning to step 308, if the patient 101 is not in asystole, then the processor 123 of the medical device 114 analyzes the received ECG waveform to determine if the waveform is indicative of a shockable cardiac rhythm (e.g., ventricular fibrillation or ventricular tachycardia) in step 312. If a shockable rhythm is detected in step 312, then the medical device 114 initiates a shock protocol in step 314 (e.g., applying one or more therapeutic shocks). Additionally, the medical device 114 will also check for ROSC (Return of Spontaneous Circulation) in subsequent step 318. In general, ROSC may be determined based on one or more of: a regular, organized heartbeat, consciousness of the patient, a palpable pulse of the patient, a measurable blood pressure, and unassisted breathing, for example. If the patient has achieved ROSC, then the treatment is discontinued in step 320. Additionally, in some embodiments, a patient may need supportive synchronized chest compressions post-ROSC. For example, in some cases, the PEA condition is found in cardiac arrest victims who have been defibrillated often following extended periods of fibrillation or asystole. The extended periods of fibrillation or asystole result in the myocardium being depleted of its energy stores, which results in its contractility being degraded causing a PEA condition. This is particularly the case when ROSC occurs as a direct result of electrical defibrillation.

If a shockable rhythm is not detected in step 312, then the processor 123 determines if the patient 101 is suffering from unconscious hypotension with an organized ECG (e.g., PEA) in step 316. Two conditions are determined at this step: 1) organized ECG, and 2) unconscious hypotension.

Determination of whether or not the ECG is organized may be determined via well-known methods, for instance, such as: first detecting the R-waves (e.g. Pan J, Tompkins W. A real-time QRS detection algorithm. IEEE Trans Eng Biomed Eng. 1985; 32(3):230-236); then measuring ECG heart rate, morphologic and amplitude characteristics for at least three R-R intervals of the ECG; then performing statistical analysis and/or decision rule determination to determine variability of at least one of the above characteristics. If the variability for at least one of the characteristics is below a threshold, then the ECG is considered "organized". Some examples of ECG heart rate characteristics include R-R interval, average heart rate over a predefined interval, and heart rate variability. Morphologic characteristics include QRS width, R-wave sharpness or other frequency domain analysis of the R-wave, Q-wave presence, P-wave presence. Amplitude characteristics include R-wave, P-wave, Q-wave, T-wave amplitudes. In one example, when the variability is less than 10%, then the ECG is considered organized.

The patient condition of unconscious hypotension may be determined, for example, via a blood pressure sensor or SpO2 sensor. The blood pressure sensor may be an invasive blood pressure sensor or a non-invasive cuff-based oscillometric blood pressure sensor. In some examples, when mean arterial pressure (MAP) falls below 40 mmHg or SpO2 falls below 85%, the patient condition of unconscious hypotension is satisfied. In general, a patient suffering from unconscious hypotension with an organized ECG or PEA will have a low blood pressure of 45/25 mmHg or lower (e.g., as low as 25/15 mmHG). In some embodiments, a diastolic pressure of 50 mmHG or less was considered low blood pressure. Blood flow may be measured via Doppler ultrasonography in certain embodiments. Doppler ultrasound uses the Doppler shift of ultrasonic waves produced from a transducer and reflected from body tissues to quantify the blood flow in peripheral vessels.

The condition of unconscious hypotension may be estimated by analysis of the ECG alone without additional blood pressure, blood flow or perfusion measurements. For instance, ECGs for patients suffering from unconscious hypotension with an organized ECG typically have common characteristics such as: a repeatable R-wave; a lack of P and/or Q-waves; the amplitudes of the ECG may be reduced; and the ECG may have wider and more rounded characteristics as compared to normal sinus rhythm. Thus, detection of one or more of these ECG morphologic characteristics (or lack thereof in the case of the P and Q waves), without the need for a blood pressure measurement, may be sufficient to indicate a patient is suffering from unconscious hypotension with an organized ECG (e.g., PEA).

In some examples, for the cases of post-defibrillation shock, unconscious hypotension is determined based solely on ECG heart rate. Following a defibrillation shock, a time period (e.g. 10, 20, 30 or 60 seconds) of ECG is analyzed. If the heart rate falls below 40 BPM in the interval post-shock defibrillation, then the patient is determined to be in unconscious hypotension. In some examples, the heart rate may be measured as the average heart rate, the minimum, or the trend in the interval.

As detailed previously, unconscious hypotension with an organized ECG may also be referred to as PEA or pseudo-PEA in that the patient is unconscious (or unresponsive) and has low blood pressure, but the patient 101 may have an organized ECG. If the unconscious hypotension with an organized ECG is not detected or otherwise determined in step 316, then the medical device returns to step 308 to re-check for asystole. Alternatively, the medical device 114 may also display a prompt or warning/alert indicating alternative treatment options should be considered (e.g., reconsider CPR, checking for other trauma such as blood loss, checking for an airway blockage, or suggesting the rescuer may need to consider administration of drugs or medications).

In the present processes, the processor 123 is configured to identify a particular cardiac condition based on waveform characteristics. For example, as shown in FIGS. 5B and 5C, the QRS complex for sinus rhythm (FIG. 5B) may be markedly different from the QRS complex of a patient suffering from unconscious hypotension with an organized ECG (or PEA, EMD or p-PEA) as shown in FIG. 5C. Additionally, other measurable characteristics of the waveform are also different. Specifically, a patient suffering from unconscious hypotension with an organized ECG (or PEA, EMD or p-PEA) may have a reduced intrinsic heart rate (e.g., lower than 60-70 beats per minute). Conversely, a patient with ventricular fibrillation will exhibit rapid irregular contractions.

In another example, the ECG for a patient suffering from unconscious hypotension with an organized ECG (or PEA, EMD or p-PEA) may be missing P and/or Q-waves. Additionally, during PEA, the amplitude of the ECG may be reduced. For example, the R-wave, which has the highest amplitude of all the waves, is typically between 0.3 and 0.5 millivolts compared to 1 millivolt for a normal sinus rhythm (e.g., generally ½ to ⅓ of the normal height during sinus rhythm). Lastly, during PEA, the QRS complex may have wider and more rounded characteristics as compared to normal sinus rhythm. For instance, a normal QRS complex typically may last 80 and 120 milliseconds and has relatively sharper peaks and valleys, as compared with the QRS complex of a patient suffering from unconscious hypotension with an organized ECG (or PEA, EMD or p-PEA). The QRS complexes of patients suffering from unconscious hypotension with an organized ECG (or PEA, EMD or p-PEA) may last more than 120 milliseconds and can be as long as 220 milliseconds, with the R-wave and S-wave having much more rounded peaks and valleys.

Returning to step 316, if the patient 101 is suffering from unconscious hypotension with an organized ECG, then the processor 123 initiates the selective activation of synchronized chest compressions in step 322 (further detailed below). While this step is illustrated as a discrete step, in an alternative embodiment, the medical device 114 may always be utilizing this algorithm whenever the medical device and chest compressor are operating. That is, the algorithm would be implemented by default. Lastly, in optional step 324, ventilations from the ventilator 120 may be synchronized with the chest compressions from the automated chest compressor 108 to increase cardiac output. For example, in one embodiment inspiration and expiration may be synchronized to systole and diastole, respectively. In another example, the ventilations may occur after a predefined number of compressions.

Figure 3B:
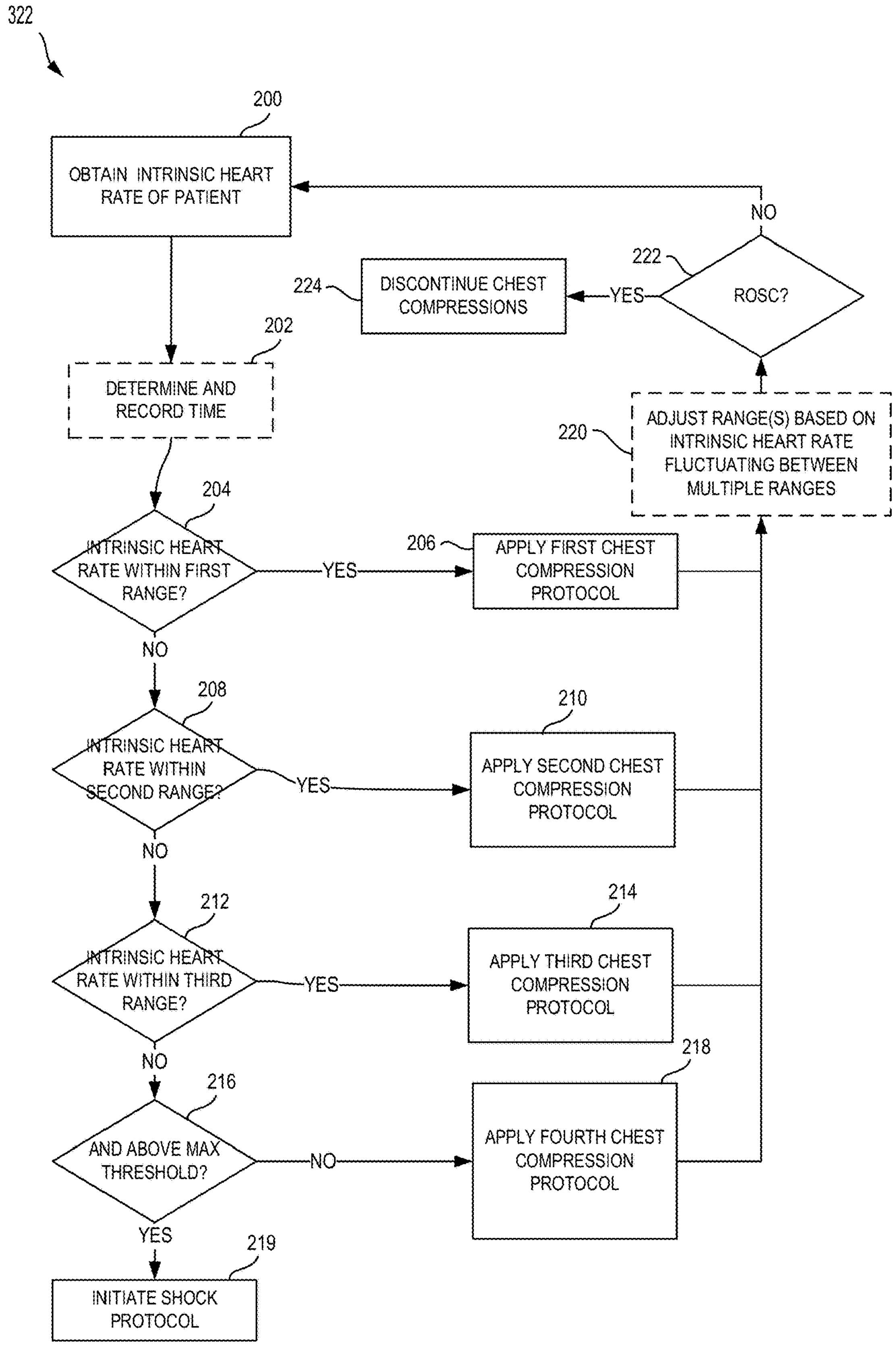
FIG. 3B is a flow chart illustrating steps for implementing an algorithm for selective activation of synchronized chest compressions of the present disclosure according to one embodiment.

FIG. 3B is a flow chart illustrating steps for implementing selective activation of synchronized chest compressions according to some embodiments. The systems and methods disclosed herein provide for delivering an optimum chest compression protocol based on the patient's current cardiac condition, for example, as indicated by a measure of the patient's intrinsic heart rate, whether or not the electrical activity associated with this heart rate gives rise to mechanical activity. For example, the patient's intrinsic heart rate may fall into one of a plurality of ranges. A particular chest compression protocol may be selected when the patient's heart rate falls within a particular range. As an illustration, the first range may be between 61 and 120 beats per minute, the second range may be between 41-60 beats per minute, the third range may be between 0 and 40 beats per minute, and the fourth range may be above 120 beats per minute. However, it can be appreciated that other ranges and/or sub-ranges of heart rate may be employed for selecting the particular chest compression protocol.

For example, the first range may be between approximately 65 and 120 beats per minute, between approximately 70 and 120 beats per minute, between approximately 55 and 120 beats per minute, between approximately 55 and 120 beats per minute, between approximately 60 and 115 beats per minute, between approximately 60 and 110 beats per minute, between approximately 60 and 125 beats per minute, or any other suitable range (or combination of ranges).

In the first step 200, the medical device 114 determines the intrinsic heart rate of the patient 101. While illustrated as a step performed by the medical device 114, in operation, the patient's intrinsic heart is continually being monitored by the medical device 114 via one or more sensors, such as ECG electrodes and/or a pulse oximeter, which automatically calculate the patient's intrinsic heart rate. In optional step 202, the medical device 114 determines and records the time and associates the time with the obtained intrinsic heart rate information where a chest compression protocol may be selected. This determination and recordation serve as a reference point (i.e., a time stamp) where the chest compression protocol is selected based on the obtained heart rate information. As an example, by reviewing the recorded heart rates and associated times in which a chest compression protocol has been selected (or remains the selected protocol), the medical device 114 is able to calculate how long the patient has exhibited a heart rate within one of the ranges, and hence, a record may be kept of what chest compression protocol(s) have been applied to the patient, and the associated times. Likewise, the medical device can determine how the patient's heart rate is generally trending (e.g., upward or downward) in response to an applied chest compression protocol.

In step 204, the medical device 114 determines that the patient's intrinsic heart rate is within the first range, associated with a first chest compression protocol. In one illustrative embodiment, the first range is approximately 61 to 120 beats per minute. However, this range could be greater or smaller. For example, the first range may be between approximately 65 and 120 beats per minute, between approximately 70 and 120 beats per minute, between approximately 55 and 120 beats per minute, between approximately 60 and 120 beats per minute, between approximately 60 and 115 beats per minute, between approximately 60 and 110 beats per minute, between approximately 60 and 125 beats per minute, between 60 and 119 beats per minute, or any other suitable range. Likewise, the range may be user programmable/configurable. If the patient's intrinsic heart rate is within this first range, then the medical device 114 applies a first chest compression protocol. In certain embodiments, this first protocol causes the chest compressor 108 to perform chest compressions synchronized to the patient's intrinsic heart rate in step 206 (see, for example, FIG. 4A). As detailed below in FIGS. 6-8, research has shown that synchronized chest compressions, with short delays relative to the peak of the R-wave (e.g., timing windows between the peak of the R-wave and the maximum depth of chest compression, as described herein), corresponded to improved blood flow for the test subjects. Other patterns of chest compressions may be employed in this protocol, such as others described herein or a different pattern.

If the patient's intrinsic heart rate does not fall within the first range, then the medical device 114 determines if the patient's intrinsic heart rate falls within the second range (e.g., between 41-60 beats per minute) in step 208. Similar to above, the second range could be various ranges. For example, the second range may be between approximately 40 and 65 beats per minute, between approximately 40 and 70 beats per minute, between approximately 40 and 50 beats per minute, between approximately 35 and 60 beats per minute, between approximately 45 and 60 beats per minute, and between approximately 40 and 59 beats per minute, to list a few examples.

If the patient's intrinsic heart rate falls within the second range, then the medical device 114 applies a second chest compression protocol that corresponds to the second range. In various embodiments, the second chest compression protocol involves the chest compressor 108 performing synchronized chest compressions in accordance with that described herein, though further including an additional chest compression interposed between the chest compressions synchronized to the patient's intrinsic heart rate in step 210 (illustratively shown in FIG. 4B). Other patterns of chest compressions may be employed in this protocol, such as others described herein. For example, alternatively, in embodiments where the heart rate of the patient is substantially low, multiple compressions may be interposed between the synchronized compressions (e.g., see FIG. 4D). That is, as discussed further herein, there may be two or more chest compressions performed for every one intrinsic heartbeat of the patient. In general, the additional interposed chest compression may be timed such that the compression occurs approximately halfway between the intrinsic heartbeats and their corresponding synchronized chest compression (e.g., based on previously observed heartbeat timings). One benefit of this protocol is that it causes the chest compressions to be delivered at a relatively constant frequency (rate), which is beneficial to maintain or increase the momentum of blood flow. Additionally, in some embodiments, the interposed chest compressions possibly have different characteristics from the synchronized ones (e.g. shallower, faster downstroke, slower downstroke, longer hold times, quicker releases, and shorter releases).

If the patient's intrinsic heart rate does not fall within the second range, then the medical device 114 determines if the patient's intrinsic heart rate falls within the third range of FIG. 3B (e.g., 0-40 beats per minute) in step 212. As with the first and second ranges of FIG. 3B, there could be various ranges such as between 0 and 50 beats per minute, between 0 and 45 beats per minute, between 0 and 35 beats per minute, between 0 and 30 beats per minute, and between 0-39 beats per minute. If the patient's intrinsic heart rate falls within the third range of FIG. 3B, then the medical device 114 may selectively apply a third chest compression protocol associated with the third range of FIG. 3B. The third compression protocol of FIG. 3B may involve the chest compressor 108 performing a pattern of regular, unsynchronized chest compressions (As provided in FIG. 4C). In general, unsynchronized chest compressions are chest compressions that are applied according to a predetermined rate, without synchronization or intent to time the chest compressions according to the patient's intrinsic heartbeats. That is, unsynchronized chest compressions do not require portions of the ECG that signal when the R-wave complex is detected. Rather, unsynchronized chest compressions apply compressions irrespective of whether an R-wave complex is present. Due to the dangerously low heart rate of the patient as indicated by the third range of FIG. 3B, the medical device 114 instructs the chest compressor 108 to provide chest compressions at a predefined rate (e.g., 80, 85, 90, 95, 100, 105, 110, 115, or 120 compressions per minute, according to basic protocols used for automated chest compressions). In certain instances, a heart rate below 40 beats per minute may be considered to be generally not life-sustaining without intervention. Thus, if the patient 101 has an intrinsic heart rate below 40 beats per minute, then it may be more beneficial to simply increase the number of chest compressions delivered to the patient than to attempt to synchronize the compressions.

Alternatively, in some cases, the third compression protocol of FIG. 3B may involve the chest compressor performing a pattern of synchronized chest compressions where, as discussed above and with respect to FIG. 4D, multiple additional compressions are interposed between synchronized compressions. This way, despite having a low heart rate with few R-wave complexes with which to synchronize compressions, a desirable number of chest compressions may be applied to the patient, in addition to synchronizing chest compressions to the R-wave complex. Otherwise, for low heart rates, protocols that only apply chest compressions at times when the R-wave complex is present may not be effective to generate desired blood flow. Accordingly, it may be preferable to not only synchronize compressions to the R-wave, but also to include additional compressions between detected R-wave complexes, as discussed above. It can be appreciated that other patterns of chest compressions may be employed in this protocol.

If the patient's intrinsic heart rate does not fall within the third range of FIG. 3B, then the patient's intrinsic heart will within a fourth range of FIG. 3B (e.g., between 120 and 150 beats per minute, between 120 and 160 beats per minute, e.g., between 120 and 170 beats per minute, or e.g., between 120 and 180 beats per minute). In this step 216, the processor 123 determines if the patient's intrinsic heart rate is above a maximum heartbeat threshold. In some instances, the upper boundary of the fourth range may border on a heart rate that is indicative of a shockable cardiac condition (e.g., ventricular fibrillation, ventricular tachycardia). For example, the upper boundary of the fourth range of FIG. 3B may be greater than or equal to 150 beats per minute, greater than or equal to 160 beats per minute, greater than or equal to 170 beats per minute, greater than or equal to 180 beats per minute, greater than or equal to 140 beats per minute, greater than or equal to 130 beats per minute, or greater than or equal to 120 beats per minute.

If the patient's intrinsic heart rate is not above the heartbeat threshold that is indicative of a shockable condition, then the medical device 114 causes the chest compressor 108 to selectively apply a fourth chest compression protocol associated with the fourth range of FIG. 3B. This fourth chest compression protocol of FIG. 3B may involve a pattern of synchronized chest compressions (timed according to the detection of an R-wave), yet with modified (or adjusted) chest compression parameters as compared to other protocols described herein. In general, above 120 beats per minute, the patient's heart is beating at least 2 times every second. To provide synchronized compressions above 120 beats per minute, the medical device 114 may need to adjust one or more chest compression parameters to fit within the chest compression cycle (e.g., the shape of the chest compression). For example, the compression depth, compression hold time, compression release velocity, compression downstroke time, compression upstroke time, and compression force may need to be modified to shorten the chest compression cycle so that chest compressions are appropriately applied, for instance, without being truncated before the next chest compression is supposed to occur. That is, a fast heart rate limits the time in which successive chest compressions may be applied, and so one or more of the above parameters may be adjusted to suit the timing of the heart rate. Additionally, or alternatively, the medical device 114 may be configured in a manner to provide synchronized compressions to a fraction of the heartbeats of the patient rather than every heartbeat. For example, synchronized compressions may be provided to every other intrinsic heartbeat of the patient 101, or a synchronized compression once every few heartbeats. As mentioned above, a fast heart rate limits the time in which successive chest compressions may be applied. Rather than modifying the chest compressions in order to be able to speed up the chest compression cycle to synchronize chest compressions with the patient's very high intrinsic heart rate, the medical device 114 simply provides chest compressions on every other or every few intrinsic heart rate so as to allow the chest compressor 108 to perform chest compressions unmodified. As the patient's heart rate in this range would likely be 120 beats per minute or more, synchronizing to a fraction of the heartbeats would still yield an acceptable number of compressions per minute, which would be synchronized to the patient's intrinsic heart rate. Additionally, an intrinsic heart rate above 120 beats could also be indicative of ROSC.

In various embodiments, the manner in which the one or more chest compression parameters are adjusted may depend on the heart rate of the patient. For example, when the heart rate is faster, there is less time for synchronized chest compressions to be applied. Accordingly, in such cases of fast heart rates (e.g., above 120 beats per minute), it may be preferable for the downstroke and upstroke of the chest compression cycle to occur faster than would otherwise be the case if the heart rate were slower. As an illustrative example, the fourth range of FIG. 3B (e.g., greater than 120 beats per minute) may be subdivided into additional sub-ranges (e.g., a first sub-range of 121-130 beats per minute, a second sub-range of 131-140 beats per minute, a third sub-range of 141-150 beats per minute, and a fourth sub-range of greater than 150 beats per minute), where the chest compression parameters are modified based on whether the heart rate falls with a particular sub-range. These sub-ranges could implement a step-wise change in response to an increased intrinsic heart rate. For example, an intrinsic heart rate of 121-130 beats per minute may result in the medical device 114 adjusting the compression depth of the chest compressor 108 from 2.4 inches down to 2 inches. This decrease in maximum compression depth is so that the downstroke and upstroke of the chest compression cycle are able to be completed by the time the next heartbeat appears since less time is required for a shallower compression depth to be reached than for a deeper compression depth. Similarly, an intrinsic heart rate of 131-140 beats per minute could result in the compression depth being further reduced to 1.5 inches, again, so as to allow for a full chest compression cycle to be completed before the next heartbeat. And an intrinsic heart rate of 141-150 beats per minute would result in the chest compression depth being reduced again to 1 inch. Likewise, other chest compression parameters could be adjusted in a similar way. For example, the hold times could be shortened, the downstroke velocity could be increased, or the upstroke or release velocity could be increased. Likewise, a combination of various chest compression parameters could be adjusted as needed.

Returning to step 216, if the patient's heart rate is greater than a particular threshold (e.g., 150, 160, 170, 180 or more beats per minute) and appears to be experiencing an arrhythmia, then the medical device 114 initiates a shock protocol in step 219. For example, the medical device 114 would analyze the patient's heart rhythm (similar to step 312 of FIG. 3A) to identify possible shockable rhythms and apply one or more therapeutic shocks in response to identification of a shockable rhythm.

As illustrated in FIG. 3B, each of the steps 206, 210, 214, and 218 lead to optional step 220, which may cause an adjustment to one or more of the ranges of steps 204, 208, 212, 216, for example, based on whether the patient's intrinsic heart rate has been fluctuating between multiple ranges. In certain embodiments, this adjustment of one or more ranges occurs when the intrinsic heart rate fluctuates between multiple ranges within a predefined (or predetermined) time. As detailed previously with respect to step 202, the medical device may keep a record of the patient's intrinsic heart rate over time. By analyzing the recorded heart rates and the associated timestamps, the medical device 114 is able to identify which ranges the patient 101 was in, how long the patient the associated chest compression protocol was applied, and whether the patient was improving over time or worsening (e.g., trending toward first range and/or toward ROSC, or trending toward third range).

While illustrated as a flow chart with discrete steps, in operation, the overall flowchart may operate as a continuous routine. In such a case, the medical device 114 will keep cycling through the steps applying one of the chest compression protocols until the patient 101 achieves ROSC (i.e., step 222) or the rescuer 105 terminates the treatment of the patient. Accordingly, the medical device 114 may cycle through the steps of this flowchart many times (e.g., hundreds or thousands of loops), where the appropriate chest compression protocol is applied to the patient depending on the cardiac activity. Ideally, whichever range the patient 101 started in, they would move toward the first range and/or ROSC in step 222. However, due to underlying medical causes, some conditions may worsen within a specified range.

Illustrated by way of example, a patient may have an erratic heart rhythm of 43 beats per minute. Accordingly, the medical device 114 may determine that the patient's intrinsic heart rate indicate that the second chest compression protocol should be applied (e.g., synchronized compressions with additional interposed chest compressions). However, due to the erratic nature of the intrinsic heart beats, the compressions may also be erratic and, therefore, inadequate. Consequently, the patient's heart rate may then fall below 40 beats per minute (into the third range), at which time the medical device 114 would then switch to unsynchronized compressions (e.g., third chest compression protocol). As these compressions are delivered, the patient's condition may improve, such that the heart rate increases to over 40 beats per minute (and back into the second range). As the heart rate shifts from one range to the other, the associated chest compression protocol will apply. In this exemplary case, as the heart rate shifts from the third range to the second range, the associated protocol will shift from unsynchronized chest compressions (exemplary third protocol) to synchronized chest compressions with interposed additional compressions between heartbeats (exemplary second protocol). Application of the synchronized chest compressions with interposed additional compressions might further improve the patient's condition, resulting in a stronger and/or faster heartbeat. Though, for a variety of reasons (e.g., inadequacy of chest compressions), the heartbeat may lapse back to a weaker beat and/or slower rate. When the heartbeat slows down, for example, such that the heart rate shifts back from the second range to the third range, then the chest compression protocol may shift accordingly. In effect, it may be possible for the heartbeat to shift multiple times between different ranges within a relatively short period of time (e.g., within 10-30 seconds, within 30-60 seconds, or a preset time), triggering the application of different protocols. However, it may be undesirable for protocols to shift so frequently, which may lead to irregularity in the manner chest compressions are applied.

In some embodiments, any of various measures may be taken to reduce or smooth fluctuation, excessive fluctuation or abrupt transitioning between ranges and protocols. For example, in some embodiments, to reduce the chances for excessive fluctuation between ranges (and, hence, reduce fluctuations between the protocol that is employed), the bounds of the ranges could be adjusted if the patient's heart rate has fallen within multiple ranges within the predefined time. For example, when the heart rate fluctuates between the second range and the third range multiple times (e.g., 3 times, 5 times, 10 times, etc.) within a predefined time period, the third range could be adjusted to 0-45, or 0-50 beats per minute, where the third protocol would be triggered when the heart rate falls within the updated range. The predefined time could be 30 seconds, 1 minute, 2 minutes, 5 minutes, etc. Likewise, the bounds could be adjusted several times in response to repeated fluctuations between ranges (e.g., the third range could be from 0-45, then 0-50, then 0-55), which would, in turn, cause the second range to be adjusted accordingly.

As a possible example instance, the intrinsic heart rate may initially be recorded at 35 beats per minutes, which would correspond to a heart rate within a range of 0-40 beats per minute, corresponding to unsynchronized chest compressions being applied to the patient. The intrinsic heart rate may then shift up to 45 beats per minute, falling within a range of 41-60 beats per minute, corresponding to synchronized chest compressions with an interposed compression between heartbeats. Due to physiological reasons, the intrinsic heart rate may lapse back to 37 beats per minute, resulting in a pattern of unsynchronized chest compression being applied. And then, the heart rate may rise to 42 beats per minute, triggering the pattern of synchronizing chest compressions with an interposed compression between heartbeats. The intrinsic heart rate may continue to oscillate back and forth multiple times between the initially set ranges of 0-40 and 41-60 beats per minute, triggering different chest compression protocols to be applied. In accordance with the above description, the system may count the number of fluctuations between ranges, and proceed to adjust the transition point between ranges so as to remain in a single chest compression protocol for a relatively longer period of time. For example, the third range may be adjusted to 0-35 beats per minute, so that an intrinsic heart rate of 37 beats per minute may still result in a pattern of synchronizing chest compressions with an interposed compression between heartbeats. When this is the case, then the second range may be adjusted to 36-60 beats per minute, or another suitable range so that the system does not have to switch so suddenly back and forth between multiple chest compression protocols.

While not illustrated in the figures, the medical device 114 may include manual options and/or a treatment "lock," which enables a user to manually set the particular chest compression protocol for the patient. Thus, even if the patient has an intrinsic heart rate that would normally result in a particular chest compression protocol, based on a preset range of heart rate, a user may override the algorithm for automatically selecting the chest compression protocol and manually select the appropriate protocol. For example, if the patient exhibits an intrinsic heart rate that falls within the second range (41-60 beats per minute, resulting in synchronized compressions with additional interposed compressions), the user may determine that the patient should receive unsynchronized compressions. Accordingly, if desirable, the user could override the determination made by the medical device 114 and set the specific chest compression protocol. For example, if the patient is suffering from PEA then the rescuer may opt to override the synchronization until intrinsic heart beats are detected.

Turning to step 222, the medical device may be able to determine whether ROSC (return of spontaneous circulation) has been achieved by the patient 101. In general, ROSC may be determined by one or more of the following: detection of an organized heart rhythm via output from ECG sensors, detection of return of consciousness of the patient (e.g., via manual input), determined ETCO2 values at life-sustaining levels, measured blood pressures at life-sustaining levels, unassisted breathing of the patient (e.g., via manual input or other method of breath detection such as impedance, flow sensing, etc.), pulse oximeter readings being synchronized with ECG readings, or another suitable method. If ROSC has been achieved, then the medical device 114 pauses or discontinues chest compressions in step 224. In one embodiment, if the patient's intrinsic heart rate is greater than 50 bpm and peripheral oximetry was greater than 80%, there is a high likelihood of ROSC.

In some cases, the PEA condition may be found in a patient who has been defibrillated following extended periods of fibrillation or asystole. The extended periods of fibrillation or asystole result in the myocardium being depleted of its energy stores. Accordingly, synchronized chest compressions may be initiated upon achieving ROSC in step 223. These compressions may be modified by, for example, being shallower in compression depth, utilizing less force on the downstroke, or synchronizing to every other (or every "nth") intrinsic heartbeat. The benefit of these synchronized chest compressions immediately following ROSC are to provide support some additional hemodynamic support to the patient upon their return to consciousness and ROSC. In another example, there also might be the need for some shallow and brief synchronized compressions for a patient soon after initiation of ECMO (extracorporeal membrane oxygenation).

In one embodiment, during the administration of chest compressions, the medical device 114 is configured to pause the chest compressor 108 from administering the chest compressions for a short period of time to allow for a check for the return of spontaneous circulation (ROSC). This pause may be as short as for a single compression, or the pause may last over a period in which multiple compressions would have been administered. Or, the pause may be set for a period of time where no compressions are administered. Such a pause may enable the medical device 114 to obtain physiological measurements of the patient (e.g., measure the activity of the heart, measure oxygen saturation, obtain capnography readings), without also capturing artifacts that are created by the chest compressions from the chest compressor 108.

In one example, the pause may occur after a set number of chest compressions. For example, after every fourth (4th) compression, a pause is introduced so that the medical device may be able to take physiological measurements without artifact that would otherwise appear due to the chest compression(s). Additionally, the set number of chest compressions may be adjusted based on the condition of the patient. For example, if the default is every fourth compression, but the patient's condition is worsening, then the pause may be set to occur after more than 4 compressions, or every set number of compression: e.g., 5, 10, 15, 20, 25, 30, 35, 40, 45, 50, 55, 60, 65, 70, 75, 80, 85, 90, 95, 100 (or greater) compressions. Moreover, if the intrinsic heart rate and/or ETCO2 are not improving, then the pause may not occur at all. Likewise, if the patient's condition is improving, then the pause may be set to in a shorter frequency (e.g., every 3, or every other chest compression). The medical device 114 may use these pauses to gradually discontinue chest compressions for the patient who is trending toward ROSC and/or has achieved ROSC. That is, rather than abruptly ending chest compressions as soon as ROSC is detected, the patient would be "weaned" off the automated chest compression. If ROSC has not been achieved, and a chest compression protocol is required, then the medical device 114 and chest compressor 108 return to step 200 to obtain the patient's intrinsic heart rate.

Figure 3C:
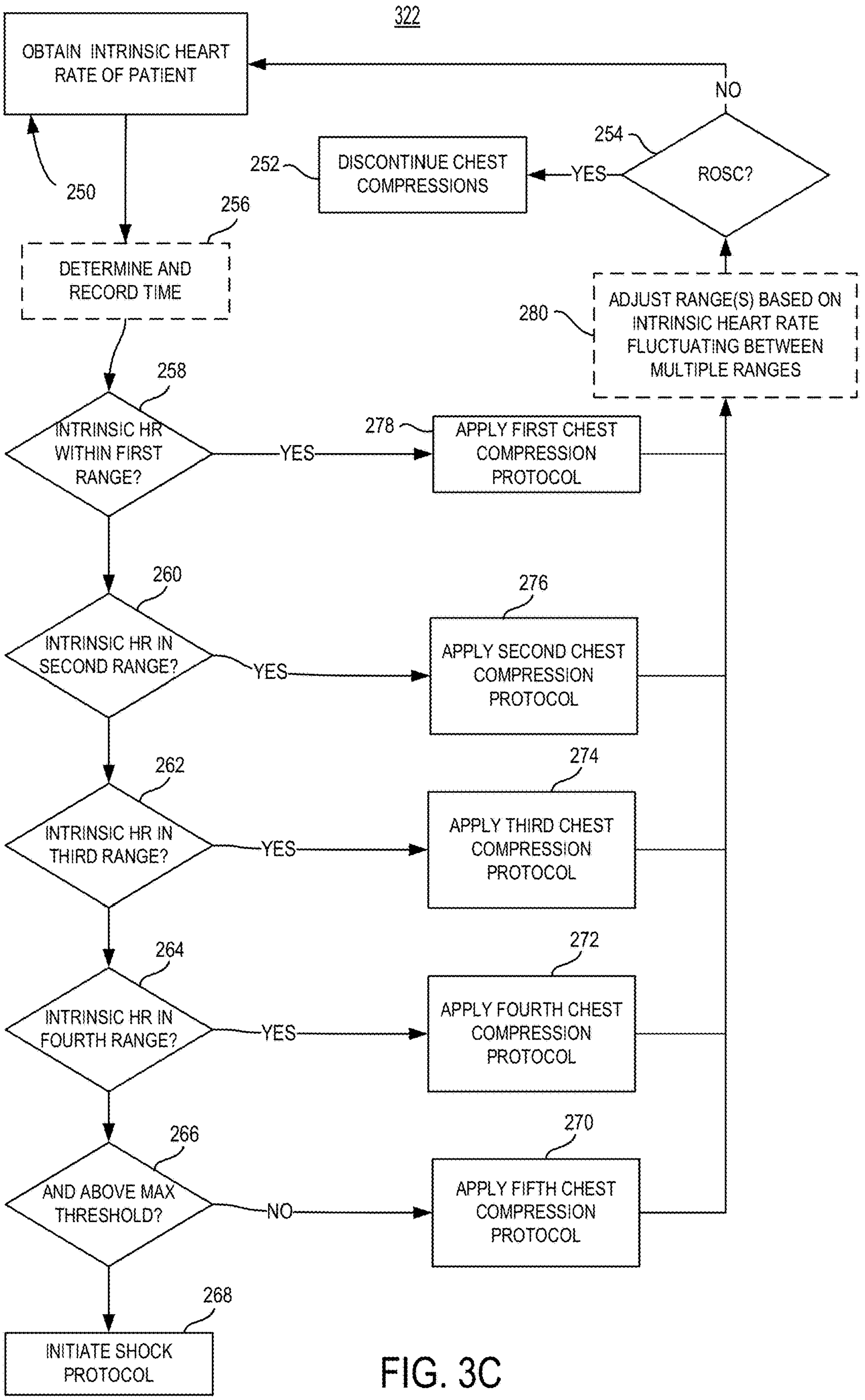
FIG. 3C is a flow chart illustrating steps for implementing an algorithm for selective activation of synchronized chest compressions of the present disclosure according to one embodiment.
Figure 4A:
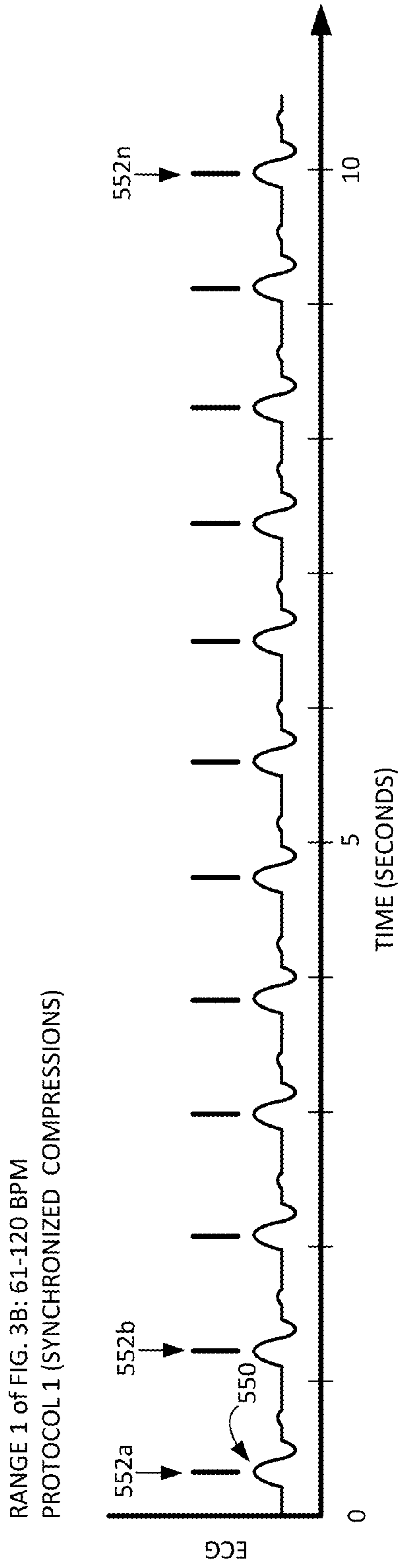
FIG. 4A illustrates how chest compressions can be synchronized to the patient's intrinsic heartbeats according to an algorithm for selective activation of synchronized chest compressions in accordance with one embodiment.
Figure 4B:
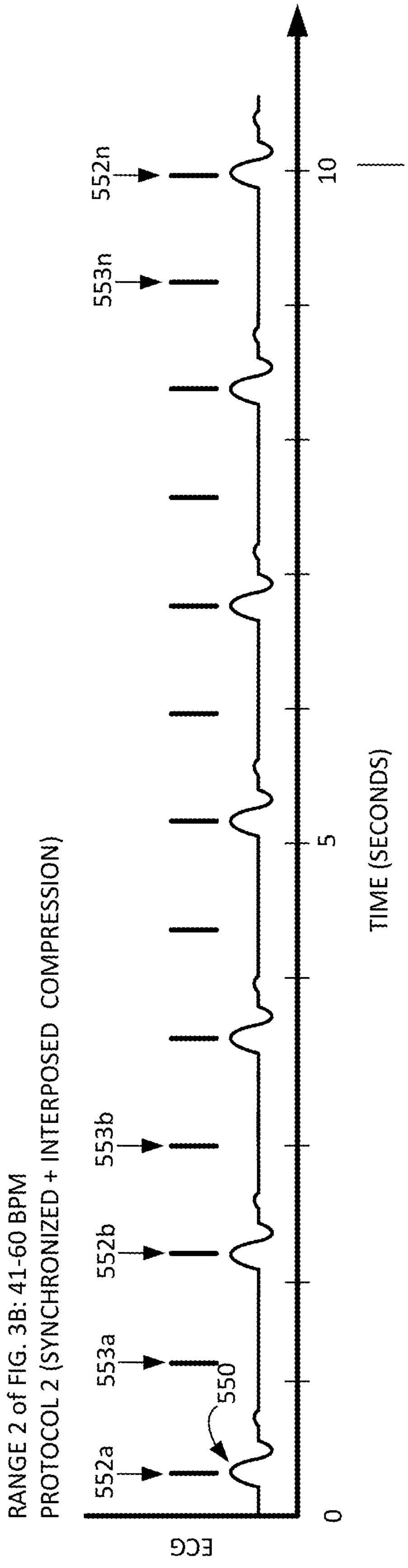
FIG. 4B illustrates how chest compressions can be synchronized to the patient's intrinsic heartbeats and an additional interposed chest compression is interposed between the patient's intrinsic heartbeats according to an algorithm for selective activation of synchronized chest compressions in accordance with one embodiment.

FIG. 3C is a flow chart illustrating steps for implementing selective activation of synchronized chest compressions according to some embodiments. In some ways, the embodiments depicted in FIG. 3C are similar to aspects of the embodiments depicted in FIG. 3B. However, as detailed further below, in the embodiments depicted in FIG. 3C, different protocols are introduced with regard to an intrinsic heart rate in subranges of the range of 0-40 beats per minute. For example, in particular, as depicted in FIG. 3C, for an intrinsic heart rate in the range of 0-20 beats per minute, unsynchronized chest compressions may be applied (as depicted in FIG. 4E, for example). Furthermore, for example, for an intrinsic heart rate in the range of 21-40 beats per minute, synchronized chest compressions may be applied along with two additional chest compressions interposed between each synchronized chest compression (as depicted in FIG. 4F, for example).

In particular, in FIG. 3C, steps 250, 256, 258, 278, 260, 276, 266, 270, 268, 280 and 254 are analogous to, in FIG. 3B, steps 200, 202, 204, 206, 208, 210, 216, 218, 219, 220 and 222, respectively.

In FIG. 3C, at step 262, if the patient's intrinsic heart rate does not fall within the second range, then the medical device 114 determines if the patient's intrinsic heart rate falls within the third range of FIG. 3C (e.g., 0-20 beats per minute, 0-19 beats per minute, etc.). It is noted that, in different embodiments, the third range could be different, such as 0-10, 0-15, 0-19, 0-25 or 0-30 beats per minute, etc. If the patient's intrinsic heart rate falls within the third range of FIG. 3C, then the medical device 114 may selectively apply a third chest compression protocol 274 of FIG. 3C associated with the third range of FIG. 3C. The third compression protocol of FIG. 3C may include the chest compressor 108 performing a pattern of regular, unsynchronized chest compressions (as depicted in FIG. 4E, for example).

At step 264, If the patient's intrinsic heart rate does not fall within the third range of FIG. 3C, then the medical device 114 determines if the patient's intrinsic heart rate falls within the fourth range of FIG. 3C (e.g., 21-40 beats per minute). It is noted that, in different embodiments, the fourth range of FIG. 3C could be different, such as 11-40, 16-40, 20-40, 20-39, 26-40, 31-40, 21-30, 21-35, 21-45 or 21-50 beats per minute, etc. (and other ranges may differ accordingly). If the patient's intrinsic heart rate falls within the fourth range of FIG. 3C, then the medical device 114 may selectively apply a fourth chest compression protocol 272 associated with the fourth range of FIG. 3C. The fourth compression protocol of FIG. 3C may include the chest compressor 108 performing synchronized chest compressions synchronized to the patient's intrinsic heart rate, but may further include performing two additional chest compressions interposed between the chest compressions synchronized to the patient's intrinsic heart rate (as depicted in FIG. 4F, for example). In other embodiments, a different number of interposed chest compressions may be used, such as one or three.

Figure 3D:
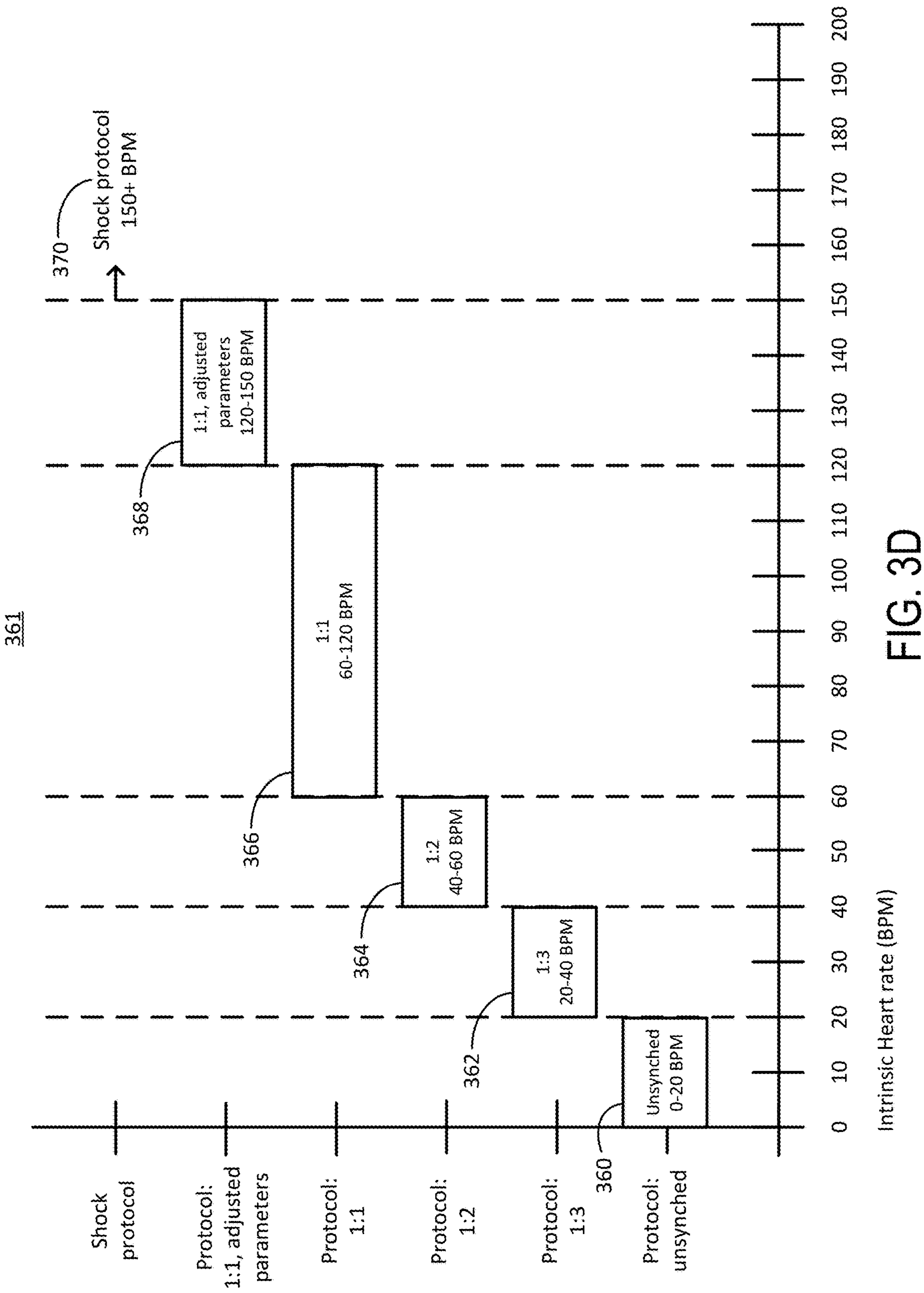
FIG. 3D is a graphical diagram illustrating an algorithm or method for selective activation of protocols in accordance with aspects of the embodiment depicted in FIG. 3C.

FIG. 3D is a graphical diagram 361 illustrating an algorithm or method for selective activation of protocols in accordance with some aspects of the embodiment depicted in FIG. 3C. The intrinsic heart rate ranges included in FIG. 3D are exemplary, and other ranges and thresholds, and variations thereof, are contemplated in various embodiments. Furthermore, the protocols are exemplary and other protocols, and variations thereof, are contemplated in various embodiments.

As depicted by box 360, if the patient's intrinsic heart rate falls in a range of between approximately 0 and approximately 20 BPM, then a protocol is administered that includes administering chest compressions at a predetermined rate, such as, for example, approximately 80 to approximately 100 compressions per minute. FIG. 4E provides an example of such a chest compression protocol, where chest compressions are administered without synchronizing to the patient's heart rate. In this particular situation, unsynchronized chest compressions are appropriate because of how infrequent the heart is beating, verging on asystole.

As depicted by box 362, if the patient's intrinsic heart rate falls in a range of between approximately 20 and approximately 40 BPM, then a protocol is administered that includes administering chest compressions at a 1:3 ratio, meaning that the protocol includes compressions synchronized with the at least one identified ECG waveform feature with two additional compressions interposed between the compressions synchronized with the at least one identified ECG waveform feature, such that a total of three compressions are administered for every one intrinsic heart beat. FIG. 4F provides an example of this chest compression protocol, in which there is a sufficiently recurrent heart beat so as to synchronize chest compressions thereto, yet the heart rate is still of such a low frequency that additional compressions administered in between heart beats would be beneficial to further assist circulation.

As depicted by box 364, if the patient's intrinsic heart rate falls in a range of between approximately 40 and approximately 60 BPM, then a protocol is administered that includes administering chest compressions at a 1:2 ratio, meaning that the protocol includes compressions synchronized with the at least one identified ECG waveform feature with one additional compression interposed between the compressions synchronized with the at least one identified ECG waveform feature, such that a total of two compressions are administered for every one intrinsic heart beat. FIG. 4B provides an example of this chest compression protocol, in which the heart beat is even more frequent and regularly occurring (than the previous case of 364) so as to synchronize chest compressions, and an additional compression administered in between heart beats would be warranted to assist circulation.

As depicted by box 366, if the patient's intrinsic heart rate falls in a range of between approximately 60 and approximately 120 BPM, then a protocol is administered that includes administering chest compressions at a 1:1 ratio, meaning that the protocol includes compressions synchronized with the at least one identified ECG waveform feature with no interposed compressions, such that one compression is administered for every one heart beat. FIG. 4A provides an example of this chest compression protocol, where the heart beat is regular enough so that synchronized chest compressions without interposed compressions in between heart beats would be selected.

As depicted by box 368, if the patient's intrinsic heart rate falls in a range of between approximately 120 and approximately 150 BPM, then a protocol is administered that includes administering chest compressions with at least one adjusted parameter, at a 1:1 ratio. For example, chest compressions could be provided at a lower frequency as compared to the heart rate where not every heart beat triggers a synchronized chest compression. Alternatively, or in combination, the adjusted parameter(s) may involve a relatively lower force or depth of compression, so as to allow for the chest compression device to administer subsequent compressions effectively.

If the patient's intrinsic heart rate falls above approximately 150 BPM, then a shock protocol may be initiated, for example, in the case of ventricular tachycardia or other shockable arrythmia.

Figure 3E:
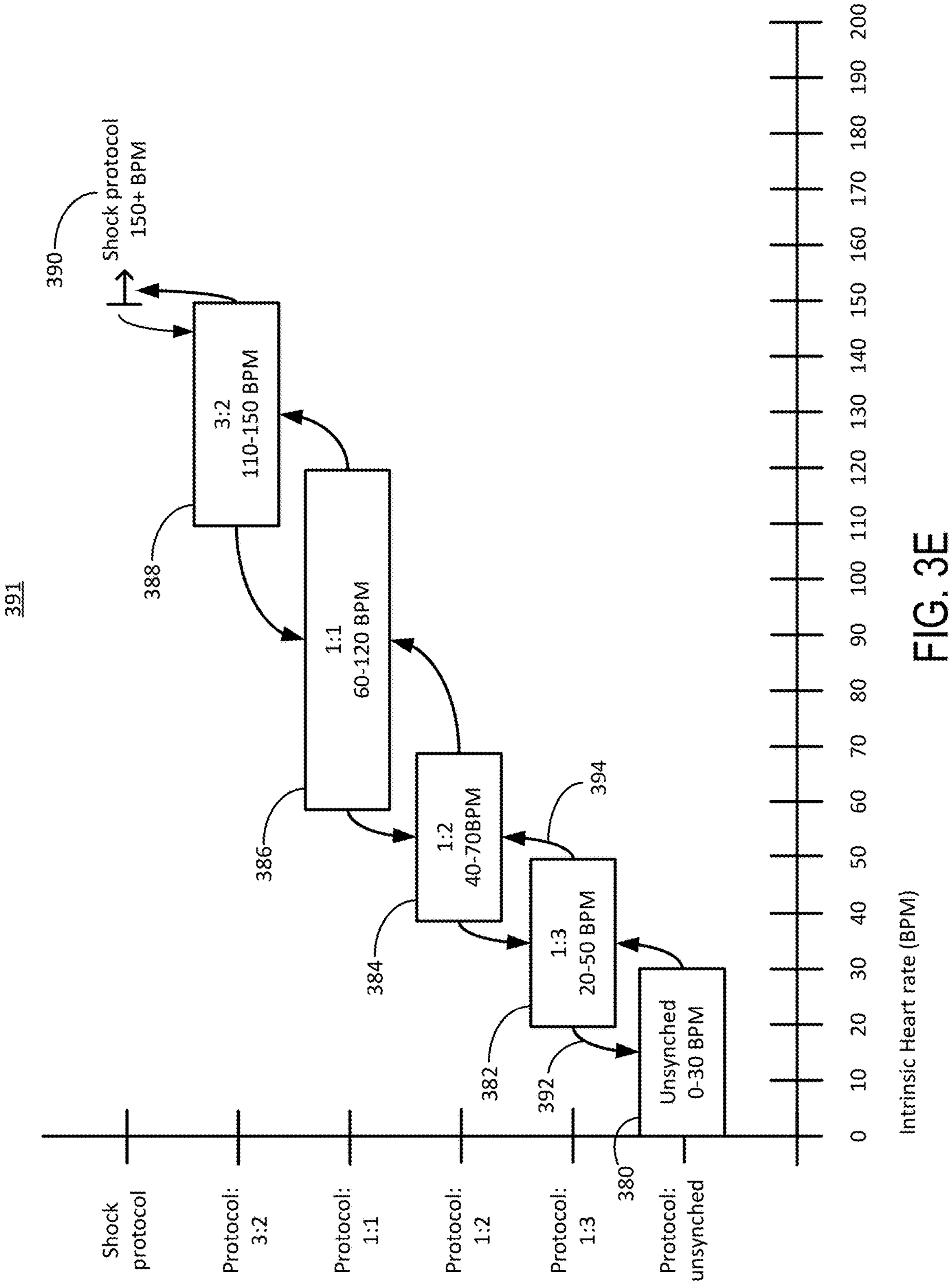
FIG. 3E is a graphical diagram illustrating an algorithm or method for selective activation of protocols, in accordance with one embodiment, which can reduce transitions between protocols.

FIG. 3E is a graphical diagram 391 illustrating an algorithm or method for selective activation of protocols, in accordance with one or more embodiments, which can be effective to reduce excessive transitioning between protocols. In some embodiments, measures, algorithms or methods may be utilized to smooth or reduce fluctuation or transitions, or excessive or overly frequent fluctuation or transitions, between ranges or protocols. One example is provided as depicted in FIG. 3E. It is noted that, in some embodiments, multiple techniques relating to smoothing or reducing fluctuation or transitions between ranges or protocols may be combined, or modified and combined, such as, for example, by also including adjustment of bounds of ranges, as described previously herein, or in other ways.

In the embodiment depicted in FIG. 3E, at least some protocols are associated with overlapping intrinsic heart rate ranges. The ranges and protocols are exemplary, and other ranges and protocols, and variations thereof, are contemplated. In this embodiment, during a period, for example, for at least some protocols, once a particular protocol is initiated, that protocol is followed until and unless the patient's intrinsic heart rate range either drops below the low end of the range for that protocol or rises above the high end of the range for that protocol. If the patient's intrinsic heart rate falls below the low end of the range for that protocol, then a particular different protocol may be transitioned to and followed, or if the patient's intrinsic heart rate rises above the high end of the range for that protocol, then another particular different protocol may be followed, where the particular different protocol transitioned to has a range that includes the patient's current heart beat rate. However, since ranges associated with particular protocols may overlap, and since transitioning is dependent upon a range associated with a protocol currently being administered, just because a patient's heart beat range falls into a range associated with another protocol not currently being administered does not necessarily mean that a transition will occur. As such, in embodiments such as the embodiment depicted in FIG. 3E, the conditions or thresholds (such as intrinsic heart rate falling below a low end threshold or above a high end threshold) that may cause or lead to transitioning from one protocol to another may be dependent, or partly dependent, on the protocol currently being administered. In this way, in some embodiments, for example, frequency of transitioning may be reduced relative to transitioning that is entirely dependent on heart rate thresholds that are independent of a protocol currently being administered. It should be understood that the particular transition endpoints of ranges described herein are exemplary in nature, and not intended to be limiting of the present disclosure, and that other transition endpoints for such ranges than those expressly noted may be employed.

As illustratively shown in FIG. 3E, assume that a patient's intrinsic heart rate is between approximately 20 and approximately 50 BPM and that a 1:3 ratio (intrinsic heartbeat to chest compression ratio) protocol is being followed, as depicted by box 382. The 1:3 ratio protocol (box 382) will continue to be followed until and unless the patient's intrinsic heart rate either (1) falls below approximately 20 BPM, in which case an unsynched, predetermined rate protocol (as depicted by box 380) is then followed (the transition being depicted by arrow 392), or (2) rises above approximately 50 BPM, in which case a 1:2 ratio (intrinsic heartbeat to chest compression ratio) protocol (as depicted by box 384) is then followed (the transition being depicted by arrow 394). If the unsynched protocol (box 380) is transitioned to, it may then be followed until and unless the patient's intrinsic heart beat rate rises above the threshold of approximately 30 BPM, in which case the 1:3 ratio (intrinsic heartbeat to chest compression ratio) protocol (box 382) may then be transitioned to and followed.

Now assume that a 1:2 ratio protocol (box 384) is being followed (for example, initially or after having been transitioned to, an example of which is described above). The 1:2 ratio protocol (box 384) will continue to be followed until and unless the patient's intrinsic heart rate either (1) falls below approximately 40 BPM, in which case the 1:3 ratio protocol (box 382) is then followed, or (2) rises above approximately 70 BPM, in which case a 1:1 ratio protocol (box 386) is then followed.

Now assume that a 1:1 ratio protocol (box 386) is being followed. The 1:1 ratio protocol (box 386) will continue to be followed until and unless the patient's intrinsic heart rate either (1) falls below approximately 60 BPM, in which case the 1:2 ratio protocol (box 384) is then followed, or (2) rises above approximately 120 BPM, in which case a 3:2 ratio protocol (box 388) is then followed. The 3:2 ratio protocol means that for every three intrinsic heart beats, only two compressions synchronized with the at least one identified ECG waveform feature are provided, such that a total of two compressions are administered for every three intrinsic heart beats. Or similarly to that described above, in such a situation, chest compressions could be provided according to one or more adjusted parameters, for example, at a lower frequency as compared to the heart rate where not every heart beat triggers a synchronized chest compression, as discussed above; alternatively, or in combination, the adjusted parameter(s) may involve a relatively lower force or depth of compression, so as to allow for the chest compression device to administer subsequent compressions effectively.

Now assume that a 3:2 ratio protocol (box 388) or protocol with one or more other adjusted parameter(s) is being followed. The 3:2 ratio protocol (box 388) will continue to be followed until and unless the patient's intrinsic heart rate either (1) falls below approximately 110 BPM, in which case the 1:1 ratio protocol (box 386) is then followed, or (2) rises above approximately 150 BPM, in which case a shock protocol 390 may be followed, where the patient may be experiencing a shockable cardiac arrhythmia such as ventricular tachycardia. In some embodiments, if, while a shock protocol is currently being administered, the patient's intrinsic heart rate then drops below approximately 150 BPM, a 3:2 ratio protocol (box 388) is then transitioned to and followed.

In various embodiments, various techniques or approaches may be utilized or incorporated into one or more algorithms in order to designate, pre-select or select a protocol, or provide rules for doing so, whether by preconfiguration or user setting. Such techniques may be utilized, for example, in the event that a patient's initial or initially assessed intrinsic heart beat rate may fall into an overlapping portion of the intrinsic heart beat ranges associated with each of two different protocols, or in other cases in which a default initial setting is needed or desired. In some embodiments, a default initial protocol is designated or utilized, such as the 1:1 ratio protocol, for example, or another protocol, such as by preconfiguration or by being pre-set or set by a user. In some embodiments, in anticipation of the possibility that a patient's initial or initially assessed intrinsic heart beat rate may fall into an overlapping portion of the intrinsic heart beat ranges associated with each of two different protocols, one of the two protocols may be designated to be utilized, such as by preconfiguration or by user setting. Such a designation may be provided for various pairs of protocols, for example, as needed. Other possibilities are contemplated in various embodiments.

FIGS. 4A-4G illustrate examples of chest compression protocols corresponding to intrinsic heart rate ranges, according to embodiments of the present system. FIG. 4A illustrates one exemplary embodiment of the first chest compression protocol, in which the chest compressions may be synchronized to the patient's intrinsic heartbeats. As detailed below in FIG. 5A, the medical device 114 detects an R-wave of a QRS complex 550 and generates a trigger signal (e.g., 552*a* to 552*n*) such that the maximum depth of compression is reached within a suitable window of time from the peak of the R-wave. Each trigger signal is then transmitted to the chest compressor 108 to perform a synchronized chest compression for the patient 101.

FIG. 4B illustrates one exemplary embodiment of the second chest compression protocol, in which the chest compressions can be synchronized to the patient's intrinsic heartbeats and an additional chest compression is added (e.g., interposed) between the synchronized chest compressions. In this embodiment, each bar 552*a*, 552*b*, to 552*n* represents a trigger signal generated by the medical device 114 upon detection of the R-wave in the QRS complex 550 where the maximum depth of compression is reached within a suitable window of time from the peak of the R-wave. Likewise, each bar 553*a*, 553*b*, to 553*n* represents a trigger signal for an interposed chest compression that occurs between the detected QRS complexes. In one implementation, the additional interposed compression is triggered after a predefined length of time after the synchronized chest compression. For example, the medical device 114 may analyze multiple QRS complexes to determine an approximate frequency and/or interval between the QRS complexes, and then trigger the additional chest compression to occur approximately half way from the synchronized compression and the expected subsequent synchronized compression, based from the expected subsequent QRS complex.

Figure 4C:
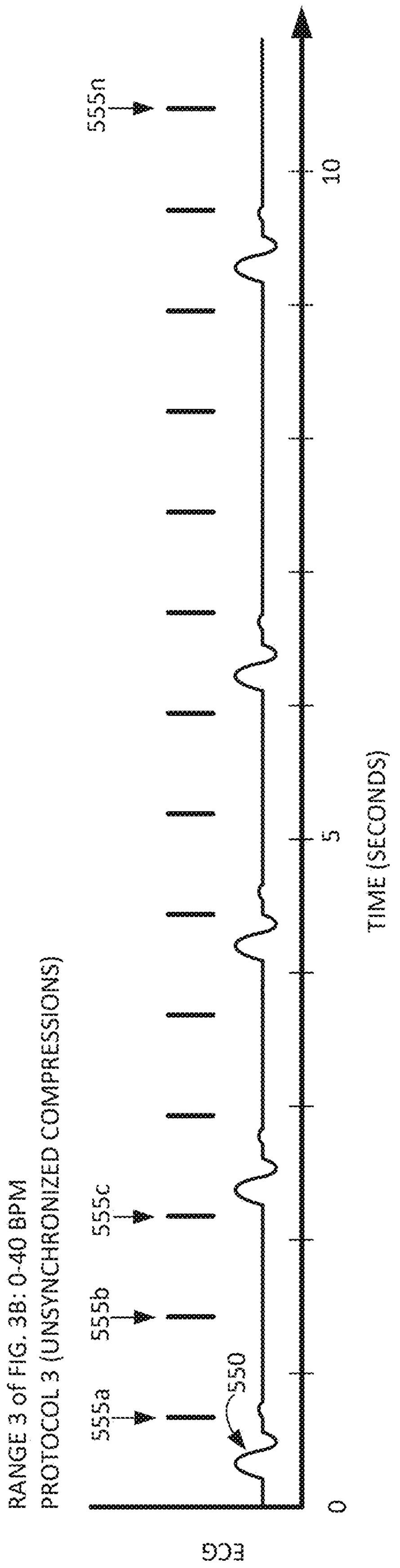
FIG. 4C illustrates how chest compressions can be unsynchronized according to an algorithm for selective activation of synchronized chest compressions in accordance with one embodiment.

FIG. 4C illustrates one exemplary embodiment of the third chest compression protocol as depicted in FIG. 3B, in which the chest compressions can be unsynchronized. As detailed previously, unsynchronized (or non-synchronized) generally indicates that the compressions are performed based on a predefined rate (e.g., 80 compressions per minute, 90 compressions per minute, 100 compressions per minute). Each bar 555*a*, 555*b*, to 555*n* represents a trigger signal sent from the medical device 114 to the chest compressor 108. As shown in the figure, the chest compression trigger signals are evenly spaced and generated independently of the QRS complexes. As illustrated, some chest compressions may naturally occur at a time that coincides with a chest compression that would have been synchronized with the patient's intrinsic heart rate. That is, unsynchronized chest compressions do not actively avoid QRS complexes, but are generated independently from whether a QRS complex appears. As discussed herein, such a chest compression protocol may be appropriate when the intrinsic heart rate of the patient is significantly low, such as below approximately 40 beats per minute, below approximately 35 beats per minute, below approximately 30 beats per minute, below approximately 25 beats per minute, below approximately 20 beats per minute, below approximately 15 beats per minute, below approximately 10 beats per minute, or when asystole occurs.

Figure 4D:
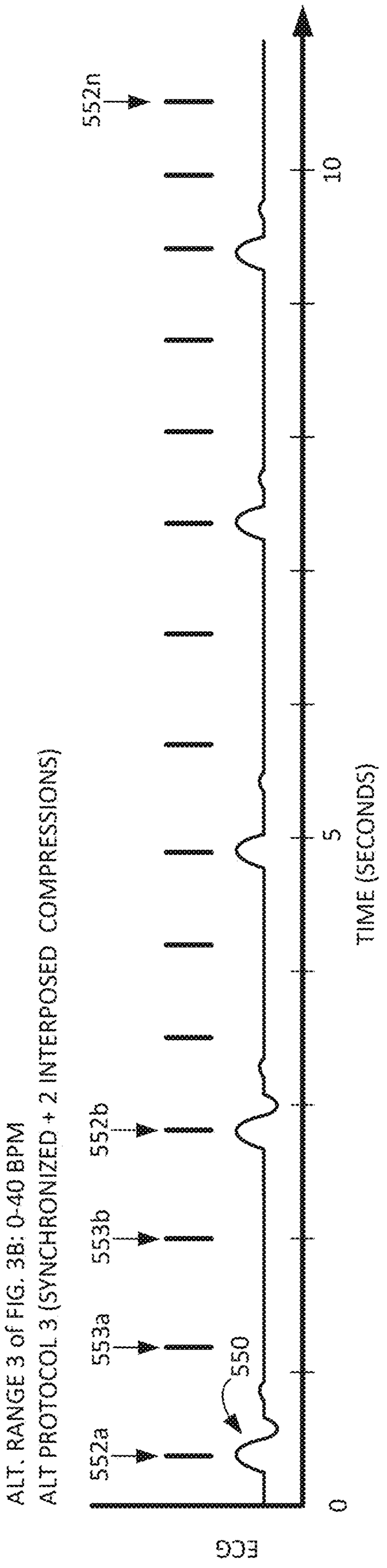
FIG. 4D illustrates how chest compressions can be synchronized to the patient's intrinsic heart beats and multiple additional chest compressions are interposed between the patient's intrinsic heartbeats in accordance with an alternative embodiment.
Figure 4E:
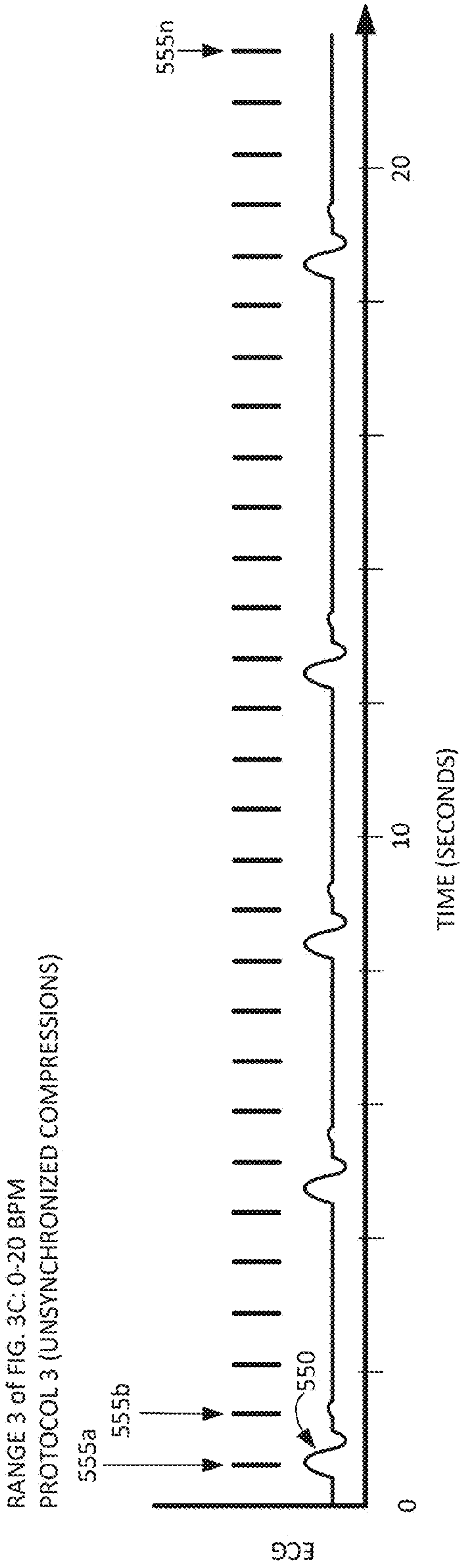
FIG. 4E illustrates how chest compressions can be unsynchronized according to an algorithm for selective activation of synchronized chest compressions in accordance with one embodiment.
Figure 4F:
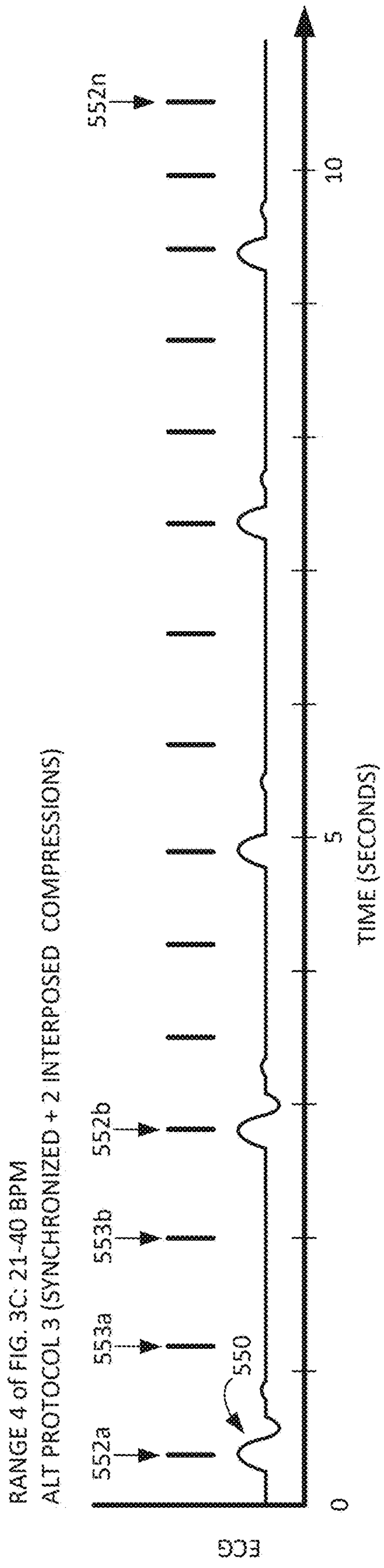
FIG. 4F illustrates how chest compressions can be synchronized to the patient's intrinsic heart beats and multiple additional chest compressions are interposed between the patient's intrinsic heartbeats in accordance with one embodiment.

FIG. 4D illustrates an alternative third chest compression protocol as depicted in FIG. 3B. In this alternative embodiment, the chest compressions can be synchronized to the patient's intrinsic heartbeats, and multiple additional chest compressions may be interposed between the synchronized chest compressions. Similar to FIG. 4B, each bar 552*a*, 552*b*, to 552*n* represents a trigger signal sent from the medical device 114 to the chest compressor 108 upon detection of the R-wave. Additionally, each bar 553*a*, 553*b*, to 553*n* represents a trigger sent between the detected R-waves and correspond to the interposed chest compression. While the illustrated embodiment depicts 2 extra chest compressions between the synchronized chest compressions, three or more interposed compressions could be added in some embodiments depending on the patient intrinsic heart rate. Similar to that discussed above with respect to unsynchronized chest compressions, such a protocol may be appropriate when the intrinsic heart rate of the patient is significantly low, such as below approximately 40 beats per minute, below approximately 35 beats per minute, below approximately 30 beats per minute, below approximately 25 beats per minute, below approximately 20 beats per minute, below approximately 15 beats per minute, below approximately 10 beats per minute, or below approximately 5 beats per minute.

FIG. 4E illustrates how chest compressions can be unsynchronized according to an algorithm for selective activation of synchronized chest compressions in accordance with one embodiment. In the embodiment depicted, chest compressions are unsynchronized.

FIG. 4F illustrates how chest compressions can be synchronized to the patient's intrinsic heart beats and multiple additional chest compressions are interposed between the patient's intrinsic heartbeats in accordance with one embodiment. As depicted, two interposed chest compressions are administered between the patient's intrinsic heartbeats.

Figure 4G:
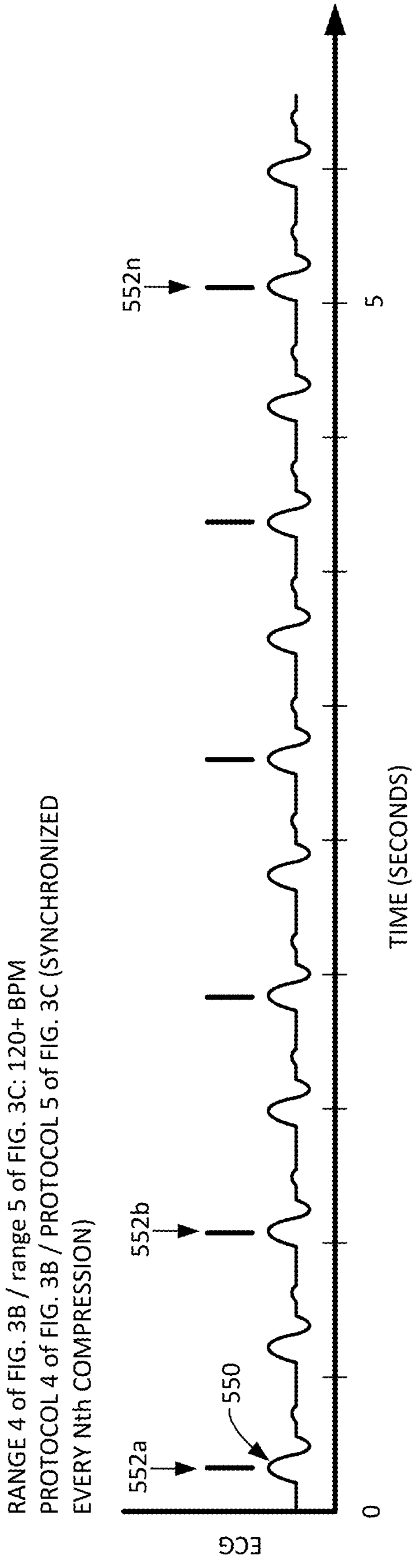
FIG. 4G illustrates an alternative chest compression protocol that may be implemented according to one embodiment.

FIG. 4G illustrates a fourth compression protocol of FIG. 3B, or a fifth compression protocol of FIG. 3C. In this embodiment, the chest compressions can be synchronized to every "nth" intrinsic heartbeat (e.g., every $2^{nd}$, $3^{rd}$, $4^{th}$, etc.) of the patient. Similar to FIG. 4B, each bar 552*a*, 552*b*, to 552*n* represents a trigger signal sent from the medical device 114 to the chest compressor 108 upon detection of the R-wave. Such a protocol may be appropriate when the intrinsic heart rate of the patient is significantly high. Such as above 120 beats per minute, above 125 beats per minute, above 130 beats per minute, above 135 beats per minute, above 140 beats per minute, above 145 beats per minute, above 150 beats per minute, above 155 beats per minute, above 160 beats per minute, above 165 beats per minute, above 170 beats per minute, above 175 beats per minute, or above 180 beats per minute. Rather than adjusting the chest compressions to speed up the chest compression, the medical device 114 only triggers on a specified number of chest compression. In this way, chest compressions are delivered at normal depth, but fewer compressions are delivered. However, as the patient's heart rate generally between 120 and 180 beats per minute, a sufficient number of chest compressions are still delivered.

Figure 5A:
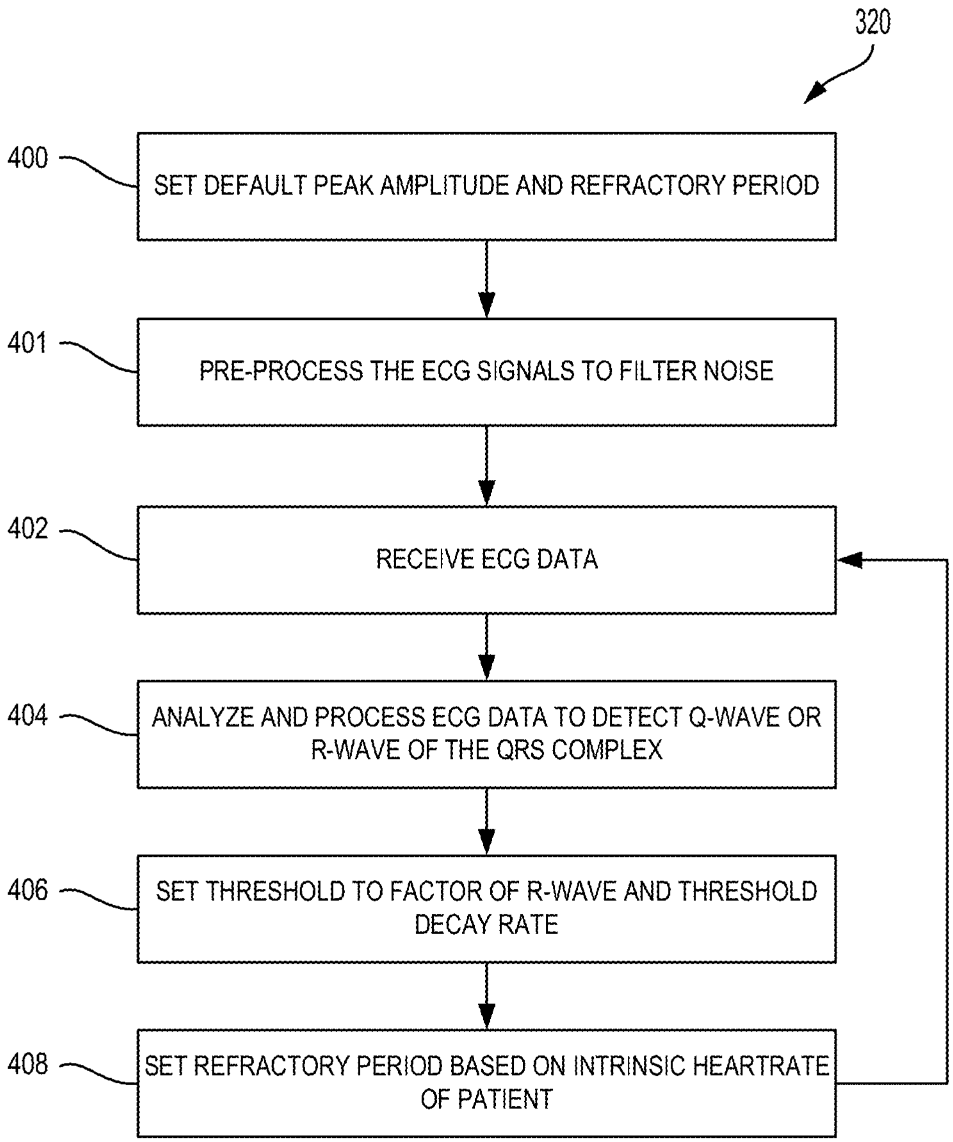
FIG. 5A is a flowchart illustrating steps for detecting QRS fiducial points in a QRS complex according to one embodiment.
Figure 5B:
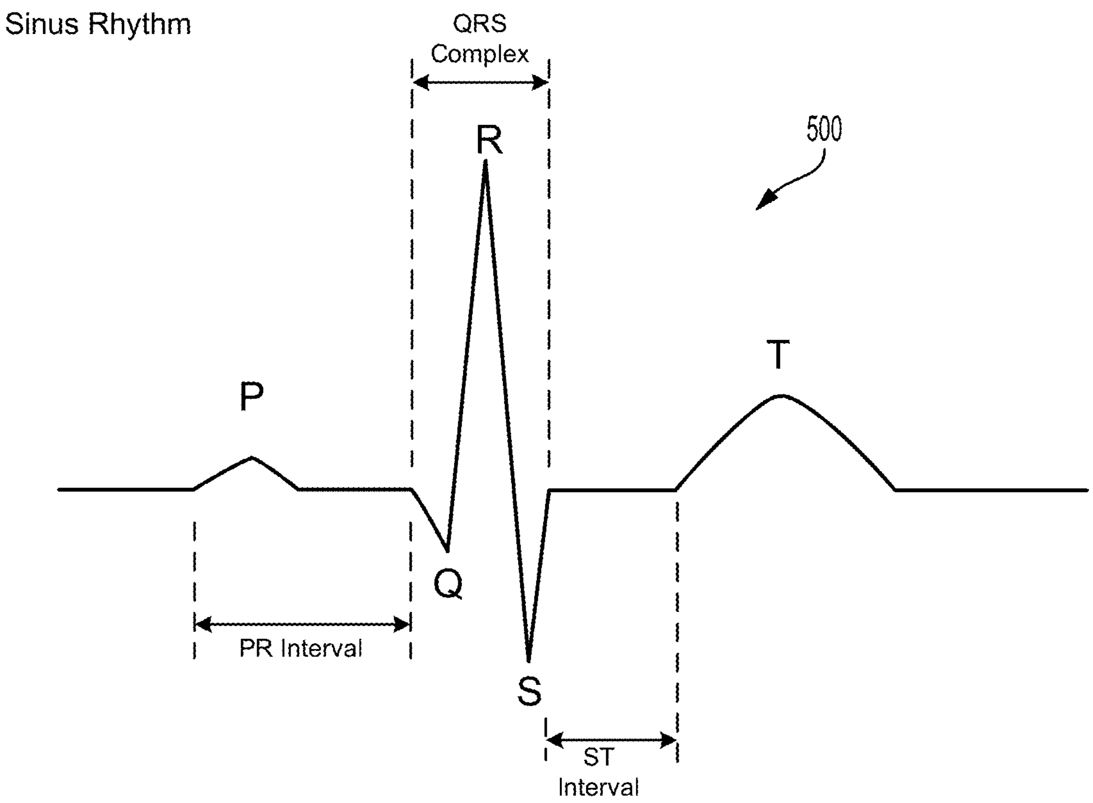
FIG. 5B illustrates an example of a QRS complex of an electrocardiogram (ECG) waveform for a patient with a normal sinus rhythm.
Figure 5C:
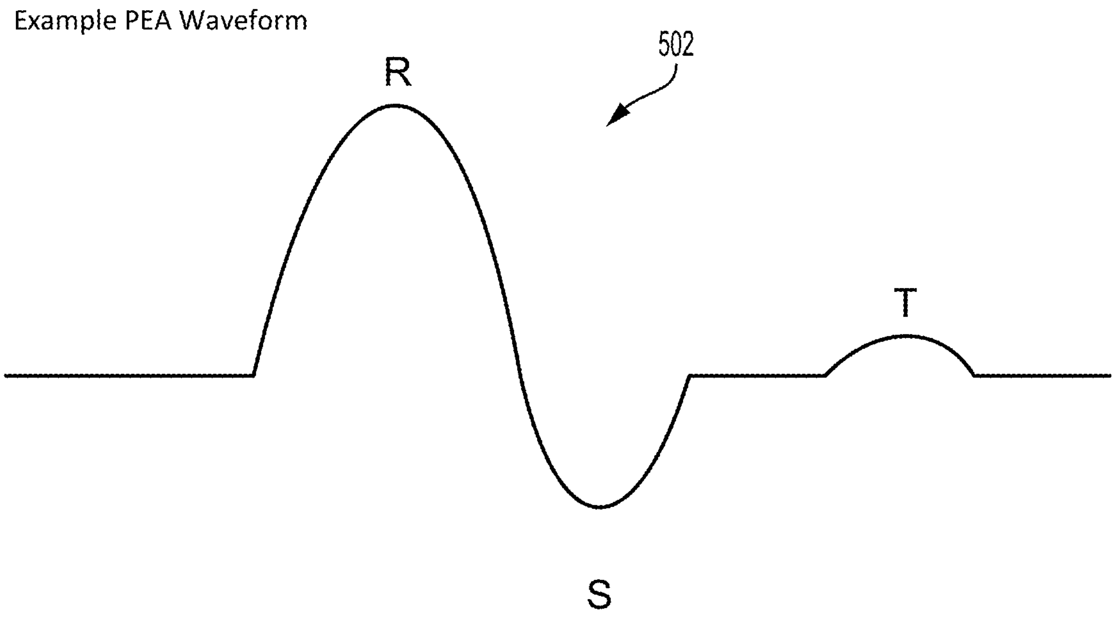
FIG. 5C illustrates an example of a QRS complex of an ECG waveform for a patient with unconscious hypotension with an organized ECG (similar to pulseless electrical activity (PEA) or pseudo pulseless electrical activity.

FIG. 5A is a flowchart illustrating steps for determining fiducial points (e.g., 519 in FIGS. 5E-5G) for initiating the synchronized chest compressions.

In this embodiment, the fiducial point is determined immediately upon detecting the presence of the R-wave. However, other embodiments may implement methods to identify other components (e.g., the P or Q-waves if present). The following steps may be performed so as to enable real-time detection of the R-waves of QRS complexes within ECG data for synchronization of chest compressions from the automated chest compressor 108 to the patient's intrinsic heartbeat. Specifically, the chest compressions may be synchronized to the peak of the R-wave of the patient's heartbeat. In order to synchronize a compression to the peak of the R-wave, the medical device 114 must be able to identify the R-wave prior to the peak.

In more detail, a QRS complex for normal sinus rhythm is typically 80-100 milliseconds long. Whereas the QRS complex for a patient suffering from unconscious hypotension with an organized ECG (or p-PEA or PEA) can be 120 milliseconds long or longer. Moreover, during conditions such as unconscious hypotension with an organized ECG or PEA, the length of time from the base of the R-wave to the peak can often be 90 milliseconds or more. Accordingly, the systems and methods described herein may be able to detect a waveform feature. For example, a Q-wave, peak of an R-wave, an R-wave on the rising (or leading edge) slope. As such, the fiducial point, and possibly the initiation of the synchronized compressions, may occur before the peak of the R-wave. Upon detection of the R-wave, the trigger signal is sent from the medical device 114 to the chest compressor 108. However, in some scenarios, the trigger signal may be delayed (timed) so as to synchronize the chest compression with a specific portion of the R-wave (e.g., just before the peak, with the peak, or just after the peak).

One exemplary algorithm for detecting QRS complexes is detailed by Pan, Jiapu and Willis J. Tompkins, "A Real-Time QRS Detection Algorithm." IEEE TRANSACTIONS ON BIOMEDICAL ENGINEERING, VOL. BME-32, NO. 3 (March 1985): 230-36; such an algorithm may be implemented in embodiments of the present disclosure.

In one specific example, in a first step 400, a default peak amplitude and refractory period are set. These default values are automatically adjusted later based on received and analyzed waveforms to more accurately set the peak amplitude threshold and refractory period. However, the values are initially set such that very few peaks, if any, within the ECG data are filtered out. As the processor 123 of the medical device 114 has not analyzed any ECG data or identified any QRS complexes, the processor 123 is not yet able to reliably identify QRS complexes and filter out unwanted noise. As mentioned previously, a waveform for someone suffering from PEA might have a peak amplitude that is only 30% (e.g., 0.3 millivolts) compared to a normal sinus waveform of a healthy patient. However, that peak value could be higher or lower. Thus, the default value needs to be low enough to detect weak signals. For example, the default value may be set as low as 0.15 millivolts, 0.10 millivolts, or even 0.05 millivolts. This ensures that weak R-waves are not inadvertently filtered out. The refractory period is based on the patient's heart rate. Until multiple QRS waveforms are received and analyzed, the processor 123 may be unable to calculate the patient's heart rate. A typical refractory period for a person with a heart rate of 60 beats per minute is 200 milliseconds. To ensure that signals are not ignored, the default refractory period may be as low as 10-20 milliseconds. In general, the refractory period is designed to help the processor filter out (i.e., ignore) peaks that might appear to be R-wave or QRS complexes, but cannot possibly be, due to the signals being detected to close to a previous heartbeat. Thus, a very short initial refractory period ensures very few signals are filtered out. This refractory period will be updated as more ECG data is analyzed and QRS complexes are identified.

In the next step 401, the processor pre-processes the ECG data to filter out high-frequency noise (e.g., muscle movements and power line noise between 50-60 Hertz). The processor 123 may perform the filtering or the medical device 114 may implement a digital signal processor, which is a processor optimized for signal processing. One embodiment of the present system implements a bandpass filter that has a passband between 5 and 15 Hertz. In step 402, the processor 123 of the medical device 114 receives ECG data measured by the ECG sensors 103A, 103B. The ECG sensors 103A, 103B detect electrical changes in voltage over time, which result from the repeated depolarization and repolarization of the myocardium during each heartbeat.

In step 404, the processor 123 analyzes and processes the ECG data to identify an R-wave of the initial QRS complex. Typical steps for detecting an R-wave in a QRS complex may include one or more of the following steps. Performing a differentiation to obtain information about the slope of the ECG waveform over time. The signal may then be squared or the absolute value is taken to allow for the detection of both positive and negative slopes. If the signal is squared, then the peak with the highest amplitude (which is generally the R-wave) to become even larger and more accentuated relative to other peaks. Lastly, integration may be performed to produce a resulting signal that includes information about both the slope and width of the QRS complex. In general, the end result of this processing is one peak that is significantly larger than the other peak, which is then identified as the R-wave by the medical device 114. The data may then be input to a threshold detector, which causes a trigger to be generated if the threshold is exceeded (i.e., an R-wave of the QRS complex is considered to have been detected).

In the next step 406, the processor 123 sets a threshold value to a factor of the peak amplitude of the filtered ECG at the point of detection or at the maximum occurring peak of the R-wave (e.g., 60-70%) and also sets a threshold decay rate. This decay rate may be a linear rate of decline from the threshold value or another predetermined or variable decay function. This threshold decay rate minimizes false positives by filtering out noise and peaks below the threshold that mimic the characteristics of the QRS complex, but have values that are too small or too close in time after the detection to the R-wave to be the R-waves of subsequent heartbeats.

In step 408, the processor 123 sets the refractory period based on the intrinsic heart rate of the patient 101. The refractory period is simply a period in which all signals are ignored. The signals are ignored because there is a period of time, for example between 200-240 milliseconds (for a heart rate of 60 beats per minute), in which subsequent heartbeats cannot physically occur. Thus, any detected peaks (e.g., noise, an artifact from chest compression, or T-waves) that might be mistaken as an R-wave during the refractory period are ignored. The refractory period helps filter out these potential false positives, which arrive too soon after a chest compression to possibly be another R-wave. Often these false positives are T-waves, which occur after the R-wave. The refractory period is automatically adjusted by the processor 123 based on the intrinsic heart rate of the patient. A faster heart rate results in a smaller refractory period, and a slower heart rate results in a longer refractory period.

The end result of such processing techniques is an output indicating a detected Q- or R-wave in the QRS complex. This signal processing may take place over a relatively short delay, for example between 5-15 milliseconds (as detailed in FIGS. 5D), with a typical delay being approximately 8-10 milliseconds. Hence, there may be a short lag, from the acquisition of the ECG data from the ECG sensors 103A, 103B until the detection of the R-wave and QRS complex by the processor 123. However, the time from the processor(s) to the detection of the R-wave of a QRS complex until the signal is received by the chest compressor 108 is negligible. As discussed herein, it may be possible for the chest to be compressed almost immediately upon detection of the presence of the R-wave, without an appreciable time lag, particularly if the processing time for detection of the R-wave, determination of the fiducial point, and control of the chest compressions is minimal. Accordingly, in some instances, when the R-wave is detected on the rising edge, the synchronized chest compression may be applied before the peak of the R-wave, or shortly (e.g., within milliseconds) thereafter.

FIGS. 5B and 5C illustrate QRS complexes for sinus rhythm and a PEA rhythm, respectively. These figures illustrate the differences between a normal sinus rhythm (FIG. 5B) and a rhythm associated with someone suffering from PEA (FIG. 5C). Additionally, a patient suffering from unconscious hypotension with an organized ECG may exhibit a heart rhythm similar to PEA (FIG. 5C).

Referring to the illustrative schematic of a QRS complex for normal sinus rhythm 500 depicted in FIG. 5B, the first wave is the P-wave, which represents atrial depolarization. The PR-interval is the period of time from the start of the P-wave to the start of the Q wave. The QRS-complex represents depolarization of the ventricles and contraction of the ventricular muscles. The ST-segment is the period of time that starts at the end of the S-wave and finishes at the start of the T-wave. And the T-wave represents ventricular repolarization. Typically, the QRS complex for sinus rhythm is approximately 80-100 milliseconds (however, it is also possible for the rhythm to be as long as 120 milliseconds). Additionally, as illustrated, the peaks and valleys of the waves in the QRS complex are characterized by relatively sharp peaks and valleys. While not illustrated, the amplitude of the peak of the R-wave is approximately 1 millivolt.

FIG. 5C illustrates an example schematic of a QRS complex for a patient suffering from unconscious hypotension with organized ECG 502. As compared to a normal sinus rhythm, the length of the time of the QRS complex is generally greater (e.g., 120-220 milliseconds). Additionally, the P-wave and Q-wave are oftentimes not present and the R and S-waves appear to be more rounded in a PEA waveform. This rounding is sometimes the result of electro-mechanical uncoupling between the electrical signals and corresponding mechanical contractions, which occurs during PEA. While not specifically illustrated, the peak of the R-wave during PEA is often between 0.3 and 0.5 millivolts (compared to 1 millivolt for sinus rhythm) in amplitude, which indicates a comparatively weak signal to a normal cardiac rhythm.

Figure 5D:
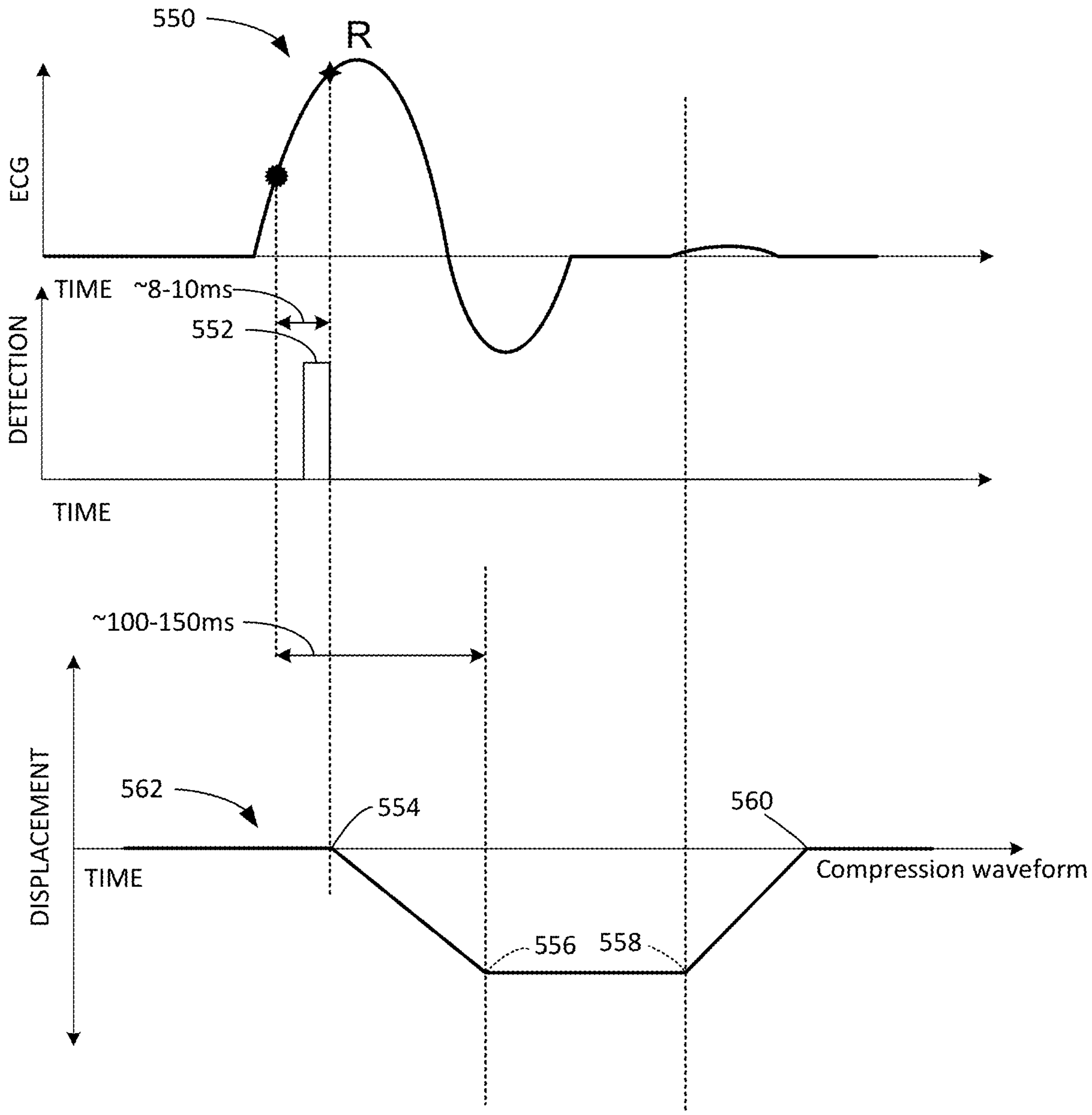
FIG. 5D illustrates a diagram illustrating the timing and relationship between a detected QRS complex, the initiation of a chest compression, and the resulting measured arterial waveform.

FIG. 5D is a diagram illustrating the timing relationship between a QRS complex 550, the trigger signal 552 generated in response to the QRS complex 550, and the chest compression, which is shown via a chest compression displacement waveform 562.

As detailed in step 402 (of FIG. 5A) the medical device 114 receives ECG data which includes QRS complexes. Inevitably, there will be some delay between the acquisition of the ECG data by the sensors, the processing of the signal by the processor 123 of the medical device 114, and the generation of the trigger signal 552. In the illustrated example, the delay from the medical device 114 receiving the ECG data and detection of the R-wave to the generation of the trigger signal 552 is approximately 8-10 milliseconds. Though, it can be appreciated that the delay between detection of the R-wave to triggering the chest compression may vary; for example, such a delay may be small, such that the trigger of a chest compression is almost immediate from when the R-wave is detected, or the delay may be longer in time.

The trigger signal 552 causes the chest compressor 108 to initiate the chest compression, which is shown by the chest compression displacement waveform 562. In this embodiment, the downstroke (point 554 where the chest compression is initiated to point 556 where the maximum compression depth is reached) begins just before the peak of the R-wave. Similarly, the hold (point 556 from where the maximum compression depth is reached to point 558 where the upstroke is initiated from the end of the hold period) and release/upstroke (point 558 where the upstroke is initiated to point 506 where the chest is released). In short, the chest compression downstroke is synchronized with the ejection phase of the heartbeat and the release is likewise synchronized with the relaxation phase of the heartbeat. This synchronization to phases of the heart provides a more efficient chest compression compared to unsynchronized chest compressions because each part of the intrinsic heartbeat is augmented by the chest compression, resulting in increased forward blood flow.

Figure 5E:
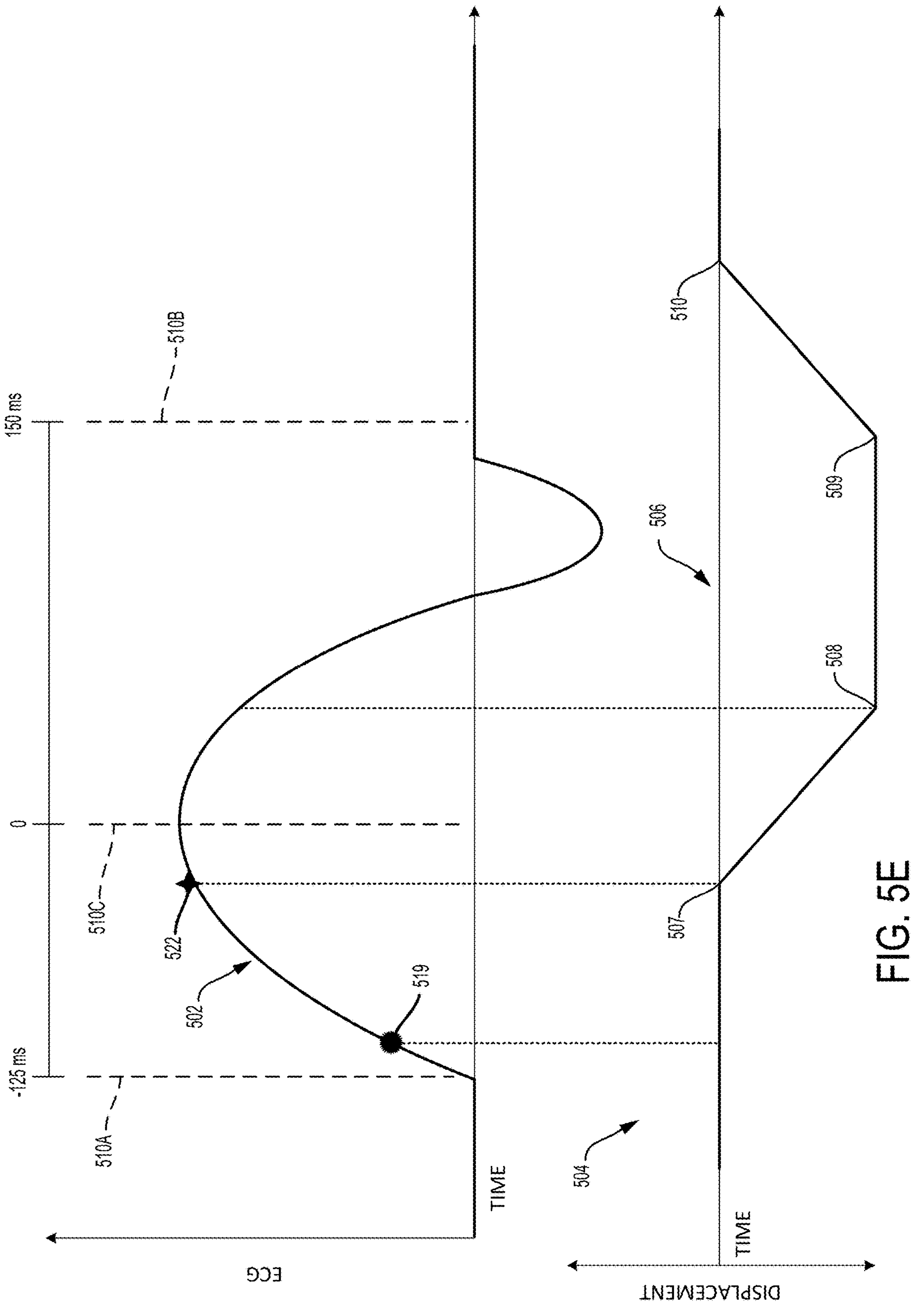
FIG. 5E illustrates an example for synchronizing chest compressions to a QRS fiducial point that is determined prior to the peak of the R-wave according to one embodiment.

FIG. 5E is an illustrative embodiment showing a schematic representation of the QRS complex for a patient suffering from unconscious hypotension with an organized ECG (or PEA) 502, a determined QRS fiducial point 519 on the leading edge of the R-wave, the trigger signal 522 which is transmitted to the automated chest compressor 108, and the chest compression displacement waveform 504 showing a chest compression cycle 506 (e.g., downstroke, hold, release/upstroke).

In more detail, this figure illustrates an example of the timing, intentional delay from detection to trigger, and synchronization of a chest compression 520 after a determined QRS fiducial point 519.

As illustrated, the trigger signal 522 is intentionally delayed by the medical device 114 and does not occur until just before the peak of the R-wave 510C. The purpose of this delay from the detection of the R-wave is to synchronize the chest compression cycle 506 (especially the down stroke; point 507 to point 208) with the peak of the R-wave 510C. Specifically, the trigger is timed such that the maximum depth of the compression will be reached within 150 milliseconds or less after the peak of the R-wave. However, it can be appreciated that a delay between the QRS complex detection indicated by QRS fiducial point 519 and the trigger signal 522 may not be necessary, as the chest compression may be triggered immediately upon detection of the QRS complex, given by the QRS fiducial point 519. As illustrated, the peak of the R-wave 510C is referred to as a reference point "time zero." The start of the R-wave and the time window is at −125 milliseconds and is reference numeral 510A. The end of the time window, in which the chest compression, should occur, is at approximately 150 milliseconds after the peak of the R-wave and is identified by reference numeral 510B. The peak of the R-wave 510C is the reference point for time zero because the effectiveness of the chest compression may decrease the farther away from the peak of the R-wave the chest compression occurs (in either direction). In certain embodiments, the peak of the R-wave may be determined as the highest point (voltage) recorded during the detected QRS complex. While an exemplary QRS complex and time window are illustrated, the width of the QRS and time window may vary, e.g., from 120 milliseconds to 220 milliseconds (possibly as wide as 300 or 400 milliseconds in some scenarios). Accordingly, the time window would also be widened to correspond to the wider QRS complex.

As detailed below with respect to FIGS. 6-8, a chest compression that occurs within a short delay (e.g., within 5 milliseconds) after the peak of the R-wave resulted in improved blood flows for test subject compared to test subjects that receive a chest compression farther away from time zero (e.g., more than 150 milliseconds after the peak of the R-wave).

For some QRS detection schemes, the R-wave may be identified on the leading edge and prior to the occurrence of the peak of the R-wave, and may even be detected on the Q-wave, which that immediately proceeds the R-wave. Upon detection of the QRS complex, the QRS fiducial point 519 may be determined (identified as Trigger in FIGS. 6 and 7). Then, upon determination of the QRS fiducial point, the processor 123 of the medical device 114 generates an output to the automated chest compressor 108 to apply a synchronized chest compression to the patient 101, so that the maximum compression depth is reached within a desired window of time from the peak of the R-wave, as discussed herein in accordance with aspects of the present disclosure.

In the illustrated example, the processor 123 of the medical device 114 causes the automated chest compressor 108 to initiate the chest compression prior to the peak of the R-wave. One benefit of initiating the chest compression prior to the peak of the R-wave is that downstroke coincides with the heart's natural ejection phase to provide the most efficient chest compression to the patient. If the compression is initiated too soon or too late, then the compression may be less effective. As the peak of the R-wave is shown as reference point time zero (time 0), the chest compression may be initiated at time −25 milliseconds (i.e., 25 milliseconds prior to the peak of the R-wave). In some embodiments, the QRS fiducial point and delay are user-programmable. In alternative embodiments, upon determination of the QRS fiducial point, the delay from the QRS fiducial point to initiation of chest compression may be: 120 milliseconds prior to the peak of the R-wave, 115 milliseconds prior to the peak of the R-wave, 110 milliseconds prior to the peak of the R-wave, 105 milliseconds prior to the peak of the R-wave, 100 milliseconds prior to the peak of the R-wave, 95 milliseconds prior to the peak of the R-wave, 90 milliseconds prior to the peak of the R-wave, 85 milliseconds prior to the peak of the R-wave, 80 milliseconds prior to the peak of the R-wave, 75 milliseconds prior to the peak of the R-wave, 60 milliseconds prior to the peak of the R-wave, 55 milliseconds prior to the peak of the R-wave, 50 milliseconds prior to the peak of the R-wave, 45 milliseconds prior to the peak of the R-wave, 40 milliseconds prior to the peak of the R-wave, 35 milliseconds prior to the peak of the R-wave, 30 milliseconds prior to the peak of the R-wave, 25 milliseconds prior to the peak of the R-wave, 20 milliseconds prior to the peak of the R-wave, 15 milliseconds prior to the peak of the R-wave, 10 milliseconds prior to the peak of the R-wave, 5 milliseconds prior to the peak of the R-wave, or synchronized to the peak of the R-wave.

As illustrated in the displacement waveform 504, the chest compression cycle 506 (e.g., downstroke point 507 where the chest compression is initiated to point 508 where the maximum compression depth is reached, hold point 508 to point 509 of the maximum compression depth, and upstroke/release point 509 from the maximum compression depth to point 510 where the chest is released) may be implemented so as to occur before the end of the time window (510B). As detailed below with respect to FIGS. 6-8, research has shown that synchronized chest compressions, which were timed to coincide with the R-wave resulted in test subjects with improved blood flows.

Figure 5F:
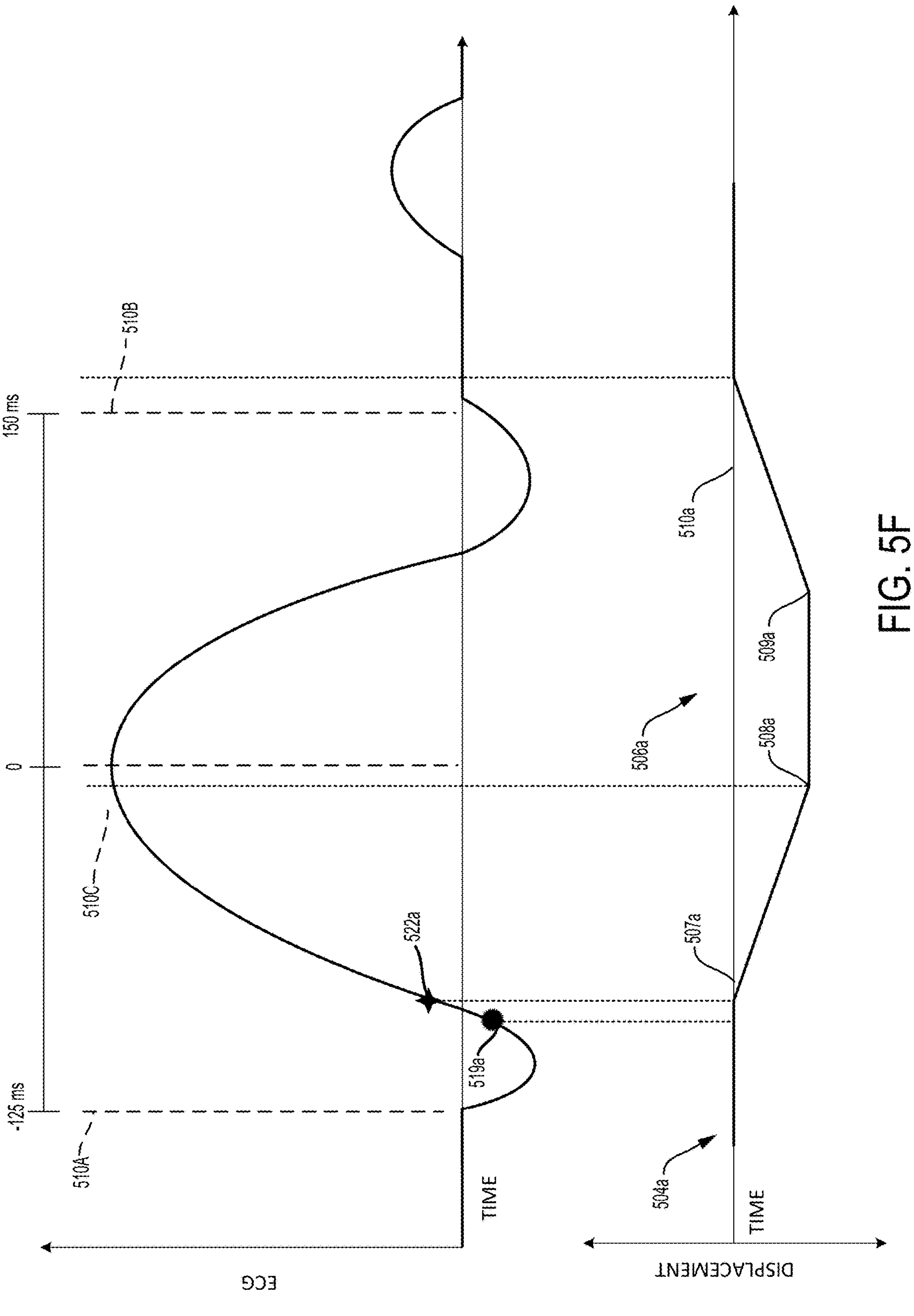
FIG. 5F illustrates an alternative example for synchronizing chest compressions to a QRS fiducial point that is determined during the Q-wave according to another embodiment.

FIG. 5F illustrates an example for synchronizing chest compressions to a QRS fiducial point 519*a* that is determined during a Q-wave according to another embodiment.

Similar to FIG. 5E, the peak of the R-wave 510C is referred to as the reference point "time zero." The start of the time window is at the start of the Q-wave and −125 milliseconds (reference numeral 510A). And the end of the time window is at approximately 150 milliseconds and is identified by reference numeral 510B. Likewise, a displacement waveform 504*a* illustrates chest compression cycle 506*a*.

As described previously, some instances of unconscious hypotension with an organized ECG or p-PEA include patients with weak heartbeats. In these situations, the patients have organized electrical activity and some amount of mechanical myocardial function. Hence, in some scenarios, the patient 101 will have ECG waveforms that include P, Q, R, S, and T-wave. Implementing, for example, the QRS detection process similar to the one described with respect to FIG. 5A, it may be possible to detect a Q-wave (i.e., the wave that proceeded the R-wave in the QRS). Upon detection of the Q-wave, the at least one processor 123 is able to determine the QRS fiducial point 519*a*, which may be on the Q-wave or the R-wave. Rather than delay the trigger signal 522*a*, the processor 123 of the medical device 114 may transmit the trigger signal to the chest compressor 108 to initiate the chest compression (as illustrated in the displacement waveform 506*a*). Accordingly, the chest target depth of the compression 508*a* was reached prior to the peak of the R-wave.

Additionally, because the chest compression was initiated well ahead of the peak of the R-wave, the medical device 114 may be able to adjust the shape (e.g., the chest compression parameters) of the chest compression cycle 506*a*. For example, the slope of the downstroke (point 507*a* where the chest compression is initiated to point 508*a* where the maximum compression depth is reached) in this embodiment is not as steep compared to the embodiment of FIG. 5E. Accordingly, this shows that the downstroke may have been performed with less force and/or over a longer period of time. Likewise, the hold time (point 508*a* where the maximum compression depth has been reached to point 509*a* where release of the chest is initiated) was lengthened and the slope of the release (point 509*a* to point 510*a* where the chest has been released) is not as steep compared to FIG. 5E, which indicates that the release was also over a longer period and/or had a lower release velocity. These changes to the compression parameters may be made to synchronize the ejection and relaxation phases of a slower heartbeat, which may translate to more efficient chest compressions for the patient 101.

Like the previous embodiment, the delay from the QRS fiducial point 519*a* to initiation of chest compression 507*a* may be user-programmable. The delay may also be: 120 milliseconds prior to the peak of the R-wave, 115 milliseconds prior to the peak of the R-wave, 110 milliseconds prior to the peak of the R-wave, 105 milliseconds prior to the peak of the R-wave, 100 milliseconds prior to the peak of the R-wave, 95 milliseconds prior to the peak of the R-wave, 90 milliseconds prior to the peak of the R-wave, 85 milliseconds prior to the peak of the R-wave, 80 milliseconds prior to the peak of the R-wave, 75 milliseconds prior to the peak of the R-wave, 60 milliseconds prior to the peak of the R-wave, 55 milliseconds prior to the peak of the R-wave, 50 milliseconds prior to the peak of the R-wave, 45 milliseconds prior to the peak of the R-wave, 40 milliseconds prior to the peak of the R-wave, 35 milliseconds prior to the peak of the R-wave, 30 milliseconds prior to the peak of the R-wave, 25 milliseconds prior to the peak of the R-wave, 20 milliseconds prior to the peak of the R-wave, 15 milliseconds prior to the peak of the R-wave, 10 milliseconds prior to the peak of the R-wave, 5 milliseconds prior to the peak of the R-wave, or synchronized to the peak of the R-wave.

Figure 5G:
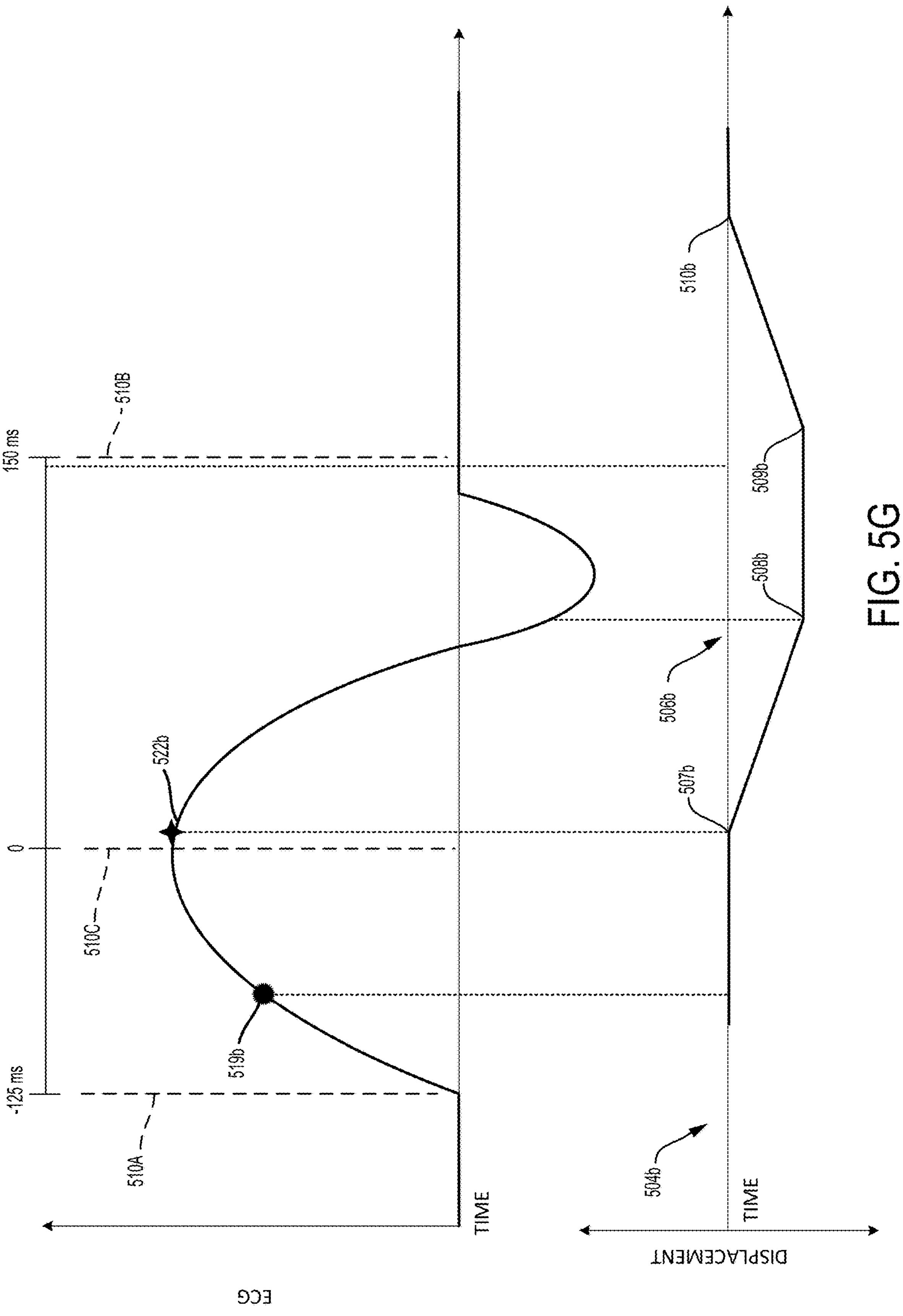
FIG. 5G illustrates an alternative example of synchronizing chest compressions after the peak of the R-wave according to another embodiment.

FIG. 5G is similar to FIG. 5E, but this figure illustrates an example for synchronizing chest compressions to a QRS fiducial point 519*b* that has a short delay after the peak of the R-wave 510C. As illustrated, the peak of the R-wave 510C may be referred to as a reference point "time zero" (or time 0) and may be determined as the highest point (voltage) recorded during the detected QRS complex. Additionally, a displacement waveform 504*b* includes a chest compression cycle 506*b*.

As detailed below with respect to FIGS. 6-8, a chest compression that occurs within a short delay (e.g., less than 5 milliseconds) after the peak of the R-wave (i.e., synchronized with R-wave) such that that the maximum compression depth had occurred less than 100 milliseconds after the peak of the R-wave resulted in improved blood flows for test subjects as compared to test subjects where the maximum chest compression depth had occurred more than 100 milliseconds after the peak of the R-wave.

In one embodiment, upon determination of the fiducial 519*b*, the processor 123 of the medical device 114 causes the automated chest compressor 108 to initiate the synchronized chest compression within 5-10 milliseconds after the peak of the R-wave (i.e., time 0) 510C. The delay between the fiducial point (i.e., detection) 519*b* and the trigger 522*b* may be automatically determined by the medical device 114 or user-programmable such that after determination of the QRS fiducial point, the completion of the chest compression is within the end of the time window 510B.

In alternative embodiments, (after determination of the QRS fiducial point) the delay when the maximum compression depth is reached (as designated by point 508*b* of the compression waveform) may be: 150 milliseconds or less after the peak of the R-wave (as designed by reference point 510C), 145 milliseconds or less after the peak of the R-wave, 140 milliseconds or less after the peak of the R-wave, 135 milliseconds or less after the peak of the R-wave, 130 milliseconds or less after the peak of the R-wave, 125 milliseconds or less after the peak of the R-wave, 120 milliseconds or less after the peak of the R-wave, 115 milliseconds or less after the peak of the R-wave, 110 milliseconds or less after the peak of the R-wave, 105 milliseconds or less after the peak of the R-wave, 100 milliseconds or less after the peak of the R-wave, 95 milliseconds or less after the peak of the R-wave, 90 milliseconds or less after the peak of the R-wave, 85 milliseconds or less after the peak of the R-wave, 80 milliseconds or less after the peak of the R-wave, 75 milliseconds or less after the peak of the R-wave, 70 milliseconds or less after the peak of the R-wave, 65 milliseconds or less after the peak of the R-wave, 60 milliseconds or less after the peak of the R-wave, 55 milliseconds or less after the peak of the R-wave, 50 milliseconds or less after the peak of the R-wave, 45 milliseconds or less after the peak of the R-wave, 40 milliseconds or less after the peak of the R-wave, 35 milliseconds or less after the peak of the R-wave, 30 milliseconds or less after the peak of the R-wave, 25 milliseconds or less after the peak of the R-wave, 20 milliseconds or less after the peak of the R-wave, 15 milliseconds or less after the peak of the R-wave, 10 milliseconds or less after the peak of the R-wave, or 5 milliseconds or less after the peak of the R-wave.

Figure 5H:
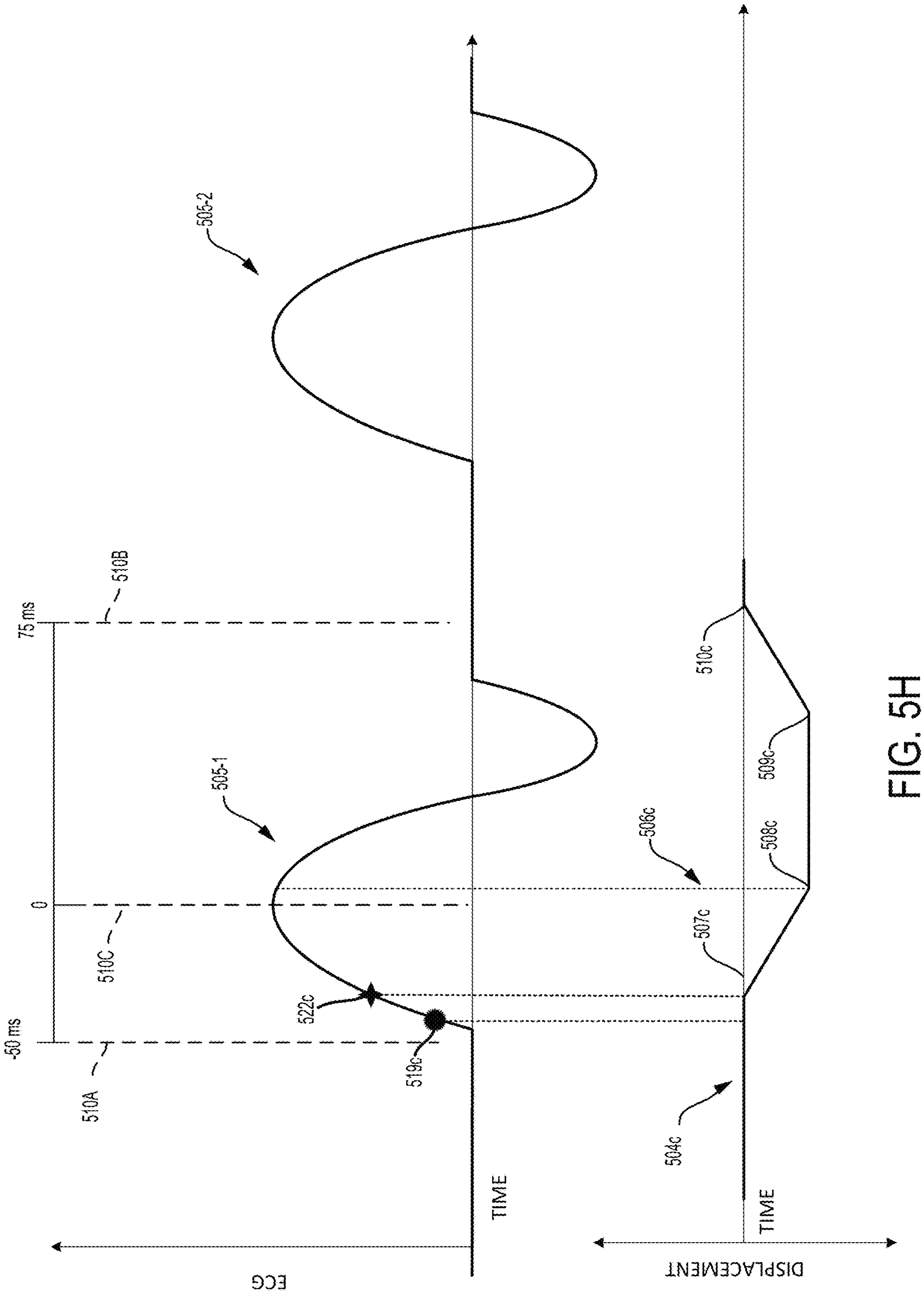
FIG. 5H illustrates an alternative example of synchronizing chest compressions with modified parameters according to one embodiment.

FIG. 5H illustrates an alternative example of synchronizing chest compressions, with modified parameters according to one embodiment.

As described previously, the peak of the R-wave 510C may be referred to as a reference point "time zero" (or time 0) and may be determined as the highest point (voltage) recorded during the detected QRS complex.

In the illustrated embodiment, the patient's intrinsic heart rate is greater than 120 beats per minute. Accordingly, the time window (from reference numeral 510A to 510B) is smaller than the previous embodiments in order to accommodate the faster chest compressions. In the illustrated example, the downstroke, hold time, and release velocity are modified to enable a quicker chest compression. That is, the downstroke does not go as deep, the hold time is not as long, and upstroke time is reduced compared to previous embodiments. Likewise, the time window is much smaller in this embodiment compared to other embodiments. Collectively, these adjustments enable the chest compression cycle to be shortened such that the chest compressor is ready to for the next ECG waveform (505-2) and chest compression. Typically, the delay between the fiducial point (i.e., detection) 519*b* and the trigger 522*b* may be automatically determined by the medical device 114 or user-programmable such that after determination of the QRS fiducial point, the chest compression reaches maximum depth prior to the end of the time window 510B. Additionally, due to the time constraints, they chest compression may simply be triggered immediately upon generation of the detection signal by the medical device 114.

In alternative embodiments, (after determination of the QRS fiducial point 519*c*) the delay from detection to when the maximum compression depth is reached (as designated by point 508*c* of the compression waveform) may be: 80 milliseconds or less after the peak of the R-wave, 75 milliseconds or less after the peak of the R-wave, 70 milliseconds or less after the peak of the R-wave, 65 milliseconds or less after the peak of the R-wave, 60 milliseconds or less after the peak of the R-wave, 55 milliseconds or less after the peak of the R-wave, 50 milliseconds or less after the peak of the R-wave, 45 milliseconds or less after the peak of the R-wave, 40 milliseconds or less after the peak of the R-wave, 35 milliseconds or less after the peak of the R-wave, 30 milliseconds or less after the peak of the R-wave, 25 milliseconds or less after the peak of the R-wave, 20 milliseconds or less after the peak of the R-wave, 15 milliseconds or less after the peak of the R-wave, 10 milliseconds or less after the peak of the R-wave, or 5 milliseconds or less after the peak of the R-wave.

Example 1: Evaluating the Hemodynamic Consequence of Synchronized Chest Compressions to Cardiac Electrical Activity in a Swine Model of Pseudo-Pulseless Electrical Activity A scientific study was performed on a swine to evaluate the effect of varying coupling intervals of synchronization of chest compression and pseudo-pulseless electrical activity (p-PEA) on blood flow and pressure in a swine asphyxial model of p-PEA. A hypothesis tested in the study was whether prolonged delays in the coupling interval of a chest compression with intrinsic electrical activity during p-PEA would worsen blood flows and pressures generated by the chest compression. Conversely, another hypothesis tested was whether short delays in the coupling interval of the chest compression with intrinsic electrical activity during P-PEA would improve blood flows and pressures generated by chest compression.

Put another way, the study tested whether short delays in the synchronization of the chest compression with the intrinsic electrical activity during p-PEA would improve the blood flows and pressures generated by the chest compression. The study mimicked a common form of respiratory cardiac arrest with an advanced cardiac life support response. The conditions included an induced asphyxial event which significantly reduced the fraction of inspired oxygen (FiO2) and subsequently reduced blood pressures to approximately 40/20 mmHg (millimeters of mercury). This was followed by synchronized chest compression and improved FiO2. Additionally, rescue defibrillations were provided if ventricular fibrillation or tachycardia occurred. The primary data being collected were aortic blood pressure, right atrial blood pressure, and carotid blood flow. Secondary data points were jugular vein blood flow, intracranial pressure (ICP), cerebral perfusion pressure (CPP), and end-tidal carbon dioxide (EtCO2).

A porcine model of p-PEA and resuscitation in domestic pigs, weighing 30±3 kg, was utilized for the study. The porcine model was selected because it is an established model and has been used successfully for more than 20 years to investigate the treatment of cardiac arrest and methods of resuscitation. Specifically, the following measurements were taken: cerebral oxygenation (StO2) was measured with a commercially available near-infrared spectroscopy (NIRS) tissue oximetry device; intracranial pressure was measured with a Millar pressure catheter in the soft tissue of the left parietal lobe of the brain; cerebral perfusion pressure (CerPP) was calculated as mean arterial pressure (from the aortic pressure signal) minus mean intracranial pressure, aortic and right atrial pressure was measured with Millar catheters and allowed for estimation of coronary perfusion pressure (CPP), which was calculated as the difference between diastolic pressure in the aorta and the diastolic pressure in the right atrium; EtCO2 was monitored to confirm intubation and as a measure of pulmonary gas exchange during the experiment; blood flows were monitored at the carotid artery and jugular vein. Other measurements included: Electrocardiography (ECG), pulse oximetry, and body temperature (temperature probe in the rectum).

The experimental procedure included anesthesia maintained with isoflurane during experimental preparation. Arterial blood gas was taken prior to the start of the experiment and analyzed. During the experiment, anesthesia was maintained as a continuous rate infusion with either Fentanyl, Propofol or Ketamine/midazolam. Mechanical ventilation was provided with a volume and rate limited ventilator. The depth of anesthesia was monitored by assessing heart rate, blood pressure, respiration, mandibular jaw tone, and absence of canthal reflex. Continuous monitoring of physiological parameters during anesthesia and throughout the experiment included cerebral oxygenation, aortic and right blood pressure, intracranial pressure, ECG, EtCO2, pulse oximetry, body temperature (temperature probe in the rectum), and carotid and jugular blood flow.

Prior to induction of P-PEA, baseline values were collected. A bolus of rocuronium (or another substitute paralytic) was given 30 seconds prior to the induction of P-PEA to prevent gasping. Additional boluses of the paralytic were given to prevent gasping as needed. P-PEA was induced via decreases in the minute ventilation and the gas mixture of O2/N2 such that a FiO2 of 6% was achieved. The onset of P-PEA was defined as an aortic systolic pressure ≤40 mmHg recorded by the aortic catheter in the presence of an organized cardiac rhythm. Chest compressions were performed by a custom stepper motor based system that is under full computer control. Mechanical ventilations were performed by a Harvard ventilator (e.g., the Harvard Large Animal Ventilator, Model 613).

It was expected that each experiment would include at least three asphyxial insults. The synchronized chest compressions had four different timings/delays (as shown in FIGS. 6-8 below) from the R-wave trigger as defined as waveform 1=5 milliseconds, waveform 2=50 milliseconds, waveform 3=125 milliseconds, and waveform 4=200 milliseconds.

The asphyxial and resuscitation protocol of test subject includes, first, baseline values were recorded, then respiration was reduced to a rate of 0 breaths per min and reduce FiO2 to 6% via mixing nitrogen into the airway. Then wait until target aortic systolic blood pressure of 40 mmHg was achieved. After achieving target aortic systolic BP, wait three minutes if it is asphyxial insult #1, two minutes if it is asphyxial insult #2, and one minute if it is asphyxial insult #3. Next, increase FiO2 to approximately 12% and test synchronized chest compressions (waveforms 1-4; detailed above) in 45-second epochs for a maximum of six minutes. If the animal was not resuscitated (defined as systolic BP>80 mmHg) after six minutes, a rescue protocol will be initiated to revive the patient.

Waveforms will be tested in four different groups:

Group 1 (N=3); 5 ms delay: test waveform 1, 2, 3, 4, 1, 2, 3, 4

Group 2 (N=3); 50 ms delay: test waveform 2, 3, 4, 1, 2, 3, 4, 1

Group 3 (N=3); 125 ms delay: test waveform 3, 4, 1, 2, 3, 4, 1, 2

Group 4 (N=3); 200 ms delay: test waveform 4, 1, 2, 3, 4, 1, 2, 3

A plurality of measurements including hemodynamic data, EtCO2 (end tidal carbon dioxide), and ECG was continuously measured and recorded on a PC-based data acquisition system (PowerLab and LabChart, ADInstruments Inc., Colorado Springs, CO). A blood flow sensor placed on the jugular vein and carotid artery blood vessels provided a measure of blood flow. Cerebral oxygenation (via NIRS) was measured from a stand-alone device. The FiO2 data was measured by a stand-alone device.

Figure 6:
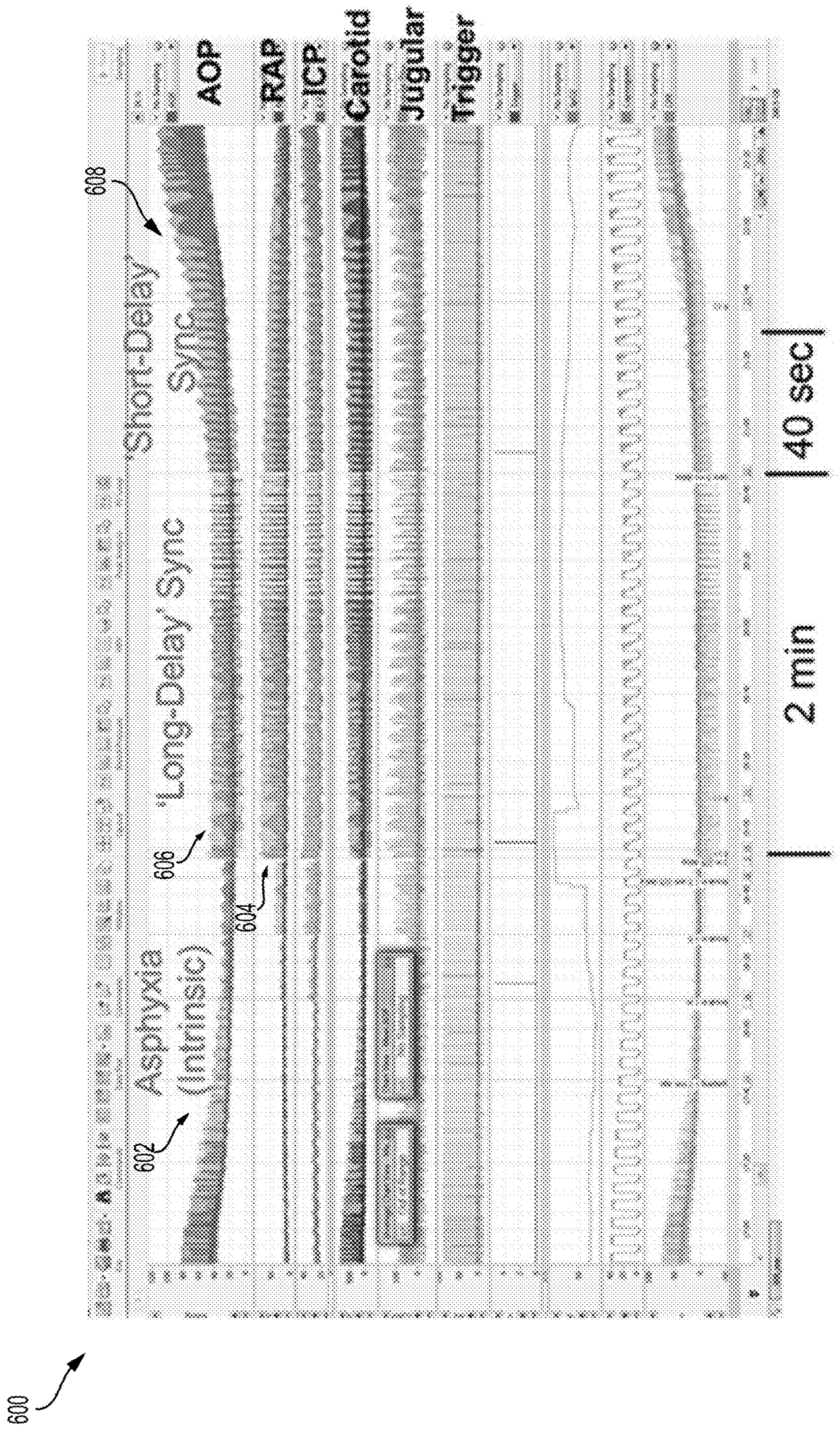
FIGS. 6-8 illustrate data from a scientific study showing the hemodynamic effects of chest compressions synchronized according to various delay periods.

FIG. 6 illustrates a graph that shows the improved hemodynamics achieved with a short synchronized delay in the setting of pseudo-PEA (P-PEA) in test animal subjects. Building on these animal studies, it is apparent that synchronization of chest compression to the R-wave of a QRS with a short delay from the detection of the R-wave (e.g., between 5 and 15 milliseconds, and preferably no longer than 100 milliseconds) improves the quality of chest compression (as measured by blood pressures and flows generated from the chest compression) over non-synchronized chest compressions and/or when chest compressions are performed more than 100 milliseconds after the peak of a detected R-wave.

Reference numeral 602 illustrates the aortic pressure (AOP) declining as part of the induced asphyxia in the patient. Reference numeral 604 illustrates increasing right atrial pressure (RAP) that occurs in P-PEA. This effect is harmful and is not life-sustaining. If the trend was allowed to continue, heart failure would result due to lack of perfusion.

Reference numeral 606 illustrates the effect of synchronized chest compressions with a long delay (225 milliseconds): AOP and RAP pressures are increased with the synchronized chest compressions, but over the course of the two minutes, the hemodynamics of the subject does not improve.

Reference numeral 608 shows the beneficial effect of using a short synchronized delay (within approximately 5 milliseconds of R-wave detection). Within just 40 seconds, the aortic pressure AOP starts to markedly increase, while the right atrial pressure simultaneously decreases indicating reduced venous congestion. Both carotid flow and jugular flow (labeled carotid and jugular, respectively) were also observed to increase in the presence of the short synchronized delay indicating improved blood flow to and from the brain.

The section labeled Trigger represents all of the identified QRS complexes detected by the medical device used in the study.

Figure 7:
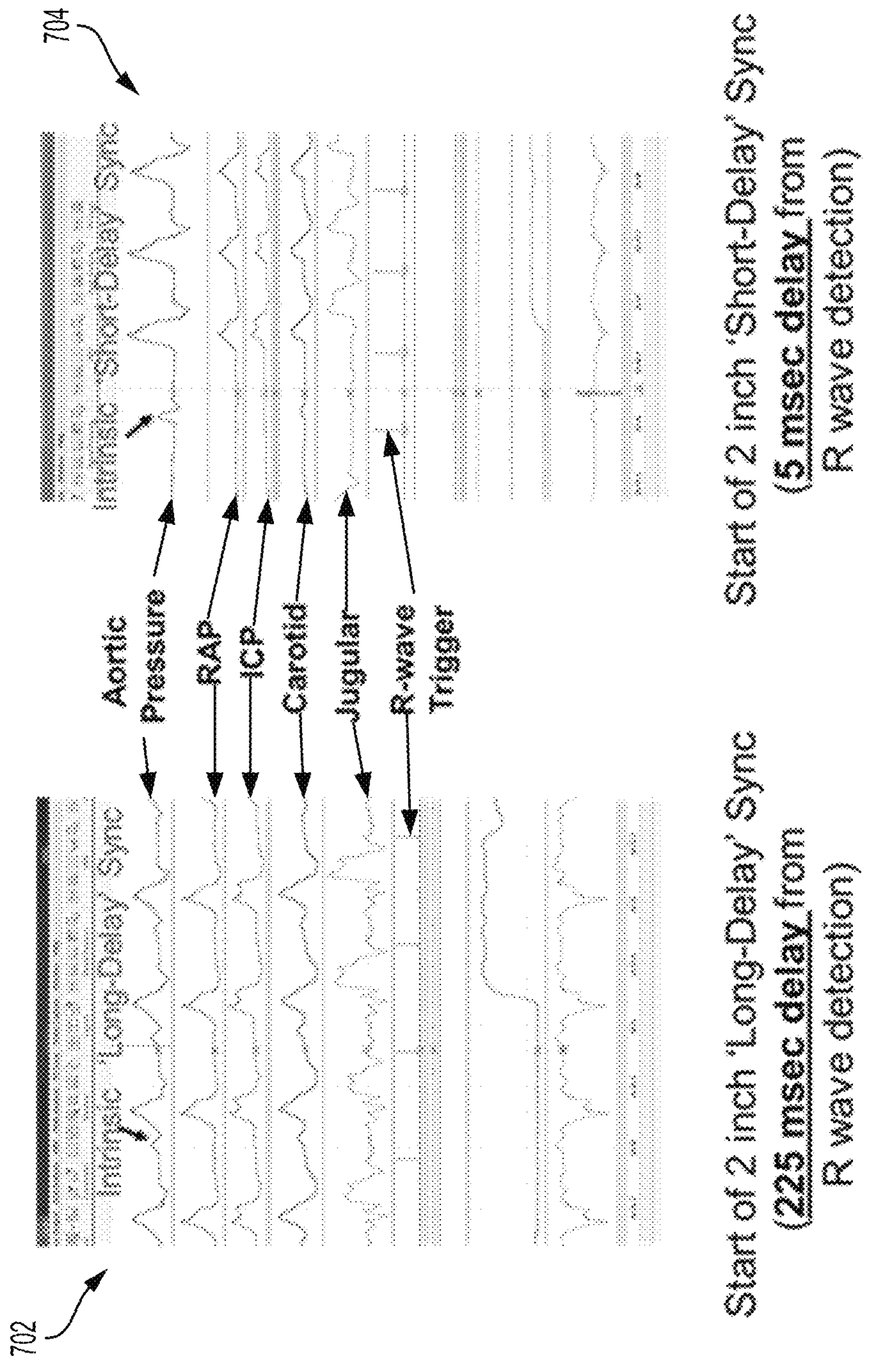

FIG. 7 is a magnified section portion of the signals illustrated in FIG. 7. This figure further illustrates the improved hemodynamics achieved with a short synchronized delay (e.g., 5 milliseconds; shown in section 704) compared to the longer synchronized delay (225 milliseconds; shown in section 702). If looking at section 702 and AOP pressure, it is appreciated that the long synchronized delay causes a pressure increase from the compression well after the intrinsic cardiac contraction. This compression occurs during diastole (i.e., when the heart trying to relax and refill with blood). This causes a large increase in right atrial pressure. Compared to section 704, however, the short synchronized delay (5 milliseconds) provides a chest compression synchronized with the R-wave of the subject's intrinsic cardiac contraction. The result is a larger overall aortic pressure and a reduced right atrial pressure. This helps illustrate the value of performing short synchronized delay compressions in the setting of P-PEA. That is, the synchronized chest compression according to the shortened delay timings helped enhance the subject's hemodynamics.

Figure 8:
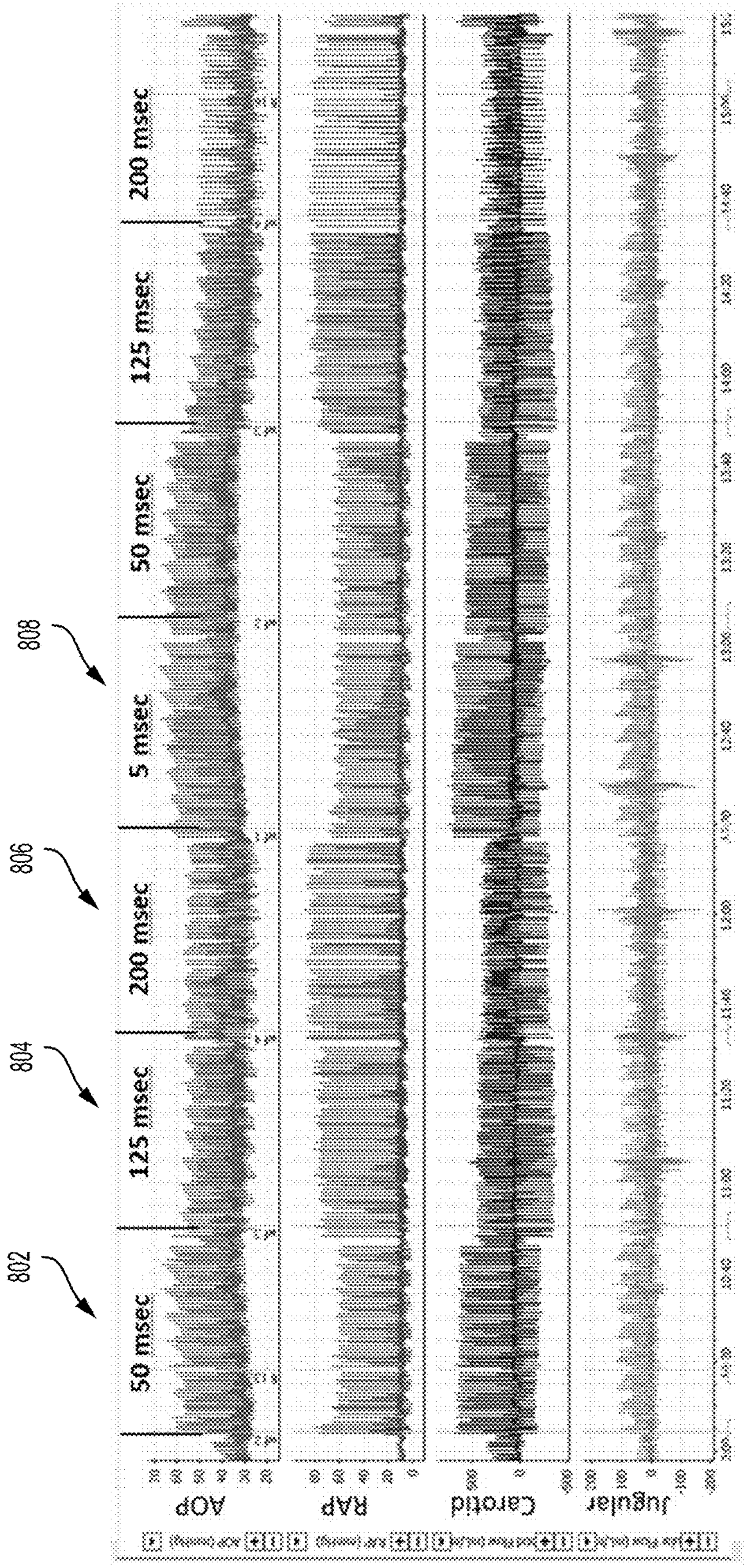

FIG. 8 is another example illustrating the improved hemodynamics achieved with a short synchronized delay of chest compression in a subject suffering P-PEA. Similar to previous examples, delays greater than 100 milliseconds (e.g., 125 milliseconds and 200 milliseconds 804, 806 respectively) yields more negative results for the test subject (e.g., decreasing AOP, increasing RAP, decreasing carotid flow). In contrast, delays less than 100 milliseconds (e.g., 5 and 50 milliseconds, 802, 808 respectively), yield more positive results (e.g., increasing AOP, decreasing RAP, and increasing carotid flow). This figure provides further indication of the benefit proving chest compressions less than 100 milliseconds after the peak of the R-wave (preferably as short as possible after the peak of the R-wave).

Example 2: Hemodynamic Comparison of Pseudo-Pulseless Electrical Activity, Pseudo-Pulseless Electrical Activity Treated with Standard Chest Compression, and Pseudo-Pulseless Electrical Activity Treated with Synchronized Chest Compression A scientific study was performed by a portion of the inventors on a swine to evaluate the effect of chest compressions and synchronized chest compressions on the hemodynamics of pseudo-pulseless electrical activity (p-PEA). This study was designed to test the hypotheses that standard chest compression resulted in better hemodynamics than untreated p-PEA and that synchronized compressions resulted in better hemodynamics than standard CPR.

A porcine model of p-PEA and resuscitation in domestic pigs, weighing 30±3 kg, was utilized for the study. The porcine model was selected because it is an established model and has been used successfully for more than 20 years to investigate the treatment of cardiac arrest and methods of resuscitation. The study mimicked a common form of respiratory cardiac arrest with an advanced cardiac life support response. The experimental procedure included anesthesia maintained with isoflurane during experimental preparation. Arterial blood gas was taken prior to the start of the experiment and analyzed. During the experiment, anesthesia was maintained as a continuous rate infusion with either Fentanyl, Propofol or Ketamine/midazolam. Mechanical ventilation was provided with a volume and rate limited ventilator. The depth of anesthesia was monitored by assessing heart rate, blood pressure, respiration, mandibular jaw tone, and absence of canthal reflex. Continuous monitoring of physiological parameters during anesthesia and throughout the experiment included cerebral oxygenation, aortic and right blood pressure, intracranial pressure, ECG, EtCO2, pulse oximetry, body temperature (temperature probe in the rectum), and carotid and jugular blood flow.

Prior to induction of P-PEA, baseline values were collected. A bolus of rocuronium (or another substitute paralytic) was given 30 seconds prior to the induction of P-PEA to prevent gasping. Additional boluses of the paralytic were given to prevent gasping as needed. P-PEA was induced via decreases in the minute ventilation and the gas mixture of O2/N2 such that a FiO2 of 6% was achieved. The onset of P-PEA was defined as an aortic systolic pressure ≤50 mmHg recorded by the aortic catheter in the presence of an organized cardiac rhythm. Chest compressions were performed by a custom stepper motor based system that is under full computer control. Mechanical ventilations were performed by a Harvard ventilator (e.g., the Harvard Large Animal Ventilator, Model 613).

Once the target aortic blood pressure was achieved the FiO2 was raised to 10% and the animal received 8 periods of 45-second treatments according to the following pattern repeated twice: Treatment 1, untreated, Treatment 2, untreated. In half the animals, Treatment 1 was synchronized chest compressions and Treatment 2 was unsynchronized chest compressions. In the other animals, the order was reversed. After completion of the 8 cycles, the FiO2 was increased to 100% and the animal was resuscitated. In the event of asystole or ventricular fibrillation, a standard resuscitation protocol was followed with standard chest compressions, defibrillation shocks when appropriate, and vasoactive drugs when needed. The primary data being collected were aortic blood pressure, right atrial blood pressure, and carotid blood flow. Secondary data points were jugular vein blood flow, intracranial pressure (ICP), cerebral perfusion pressure (CPP), and end-tidal carbon dioxide (EtCO2).

It was expected that each experiment would include at least three asphyxial insults followed by treatment and resuscitation. Synchronized chest compressions were triggered on the R-wave and delivered without delay. Unsynchronized chest compressions were delivered at a rate of 100 compressions per minute with a 50% duty cycle.

Figure 9A:
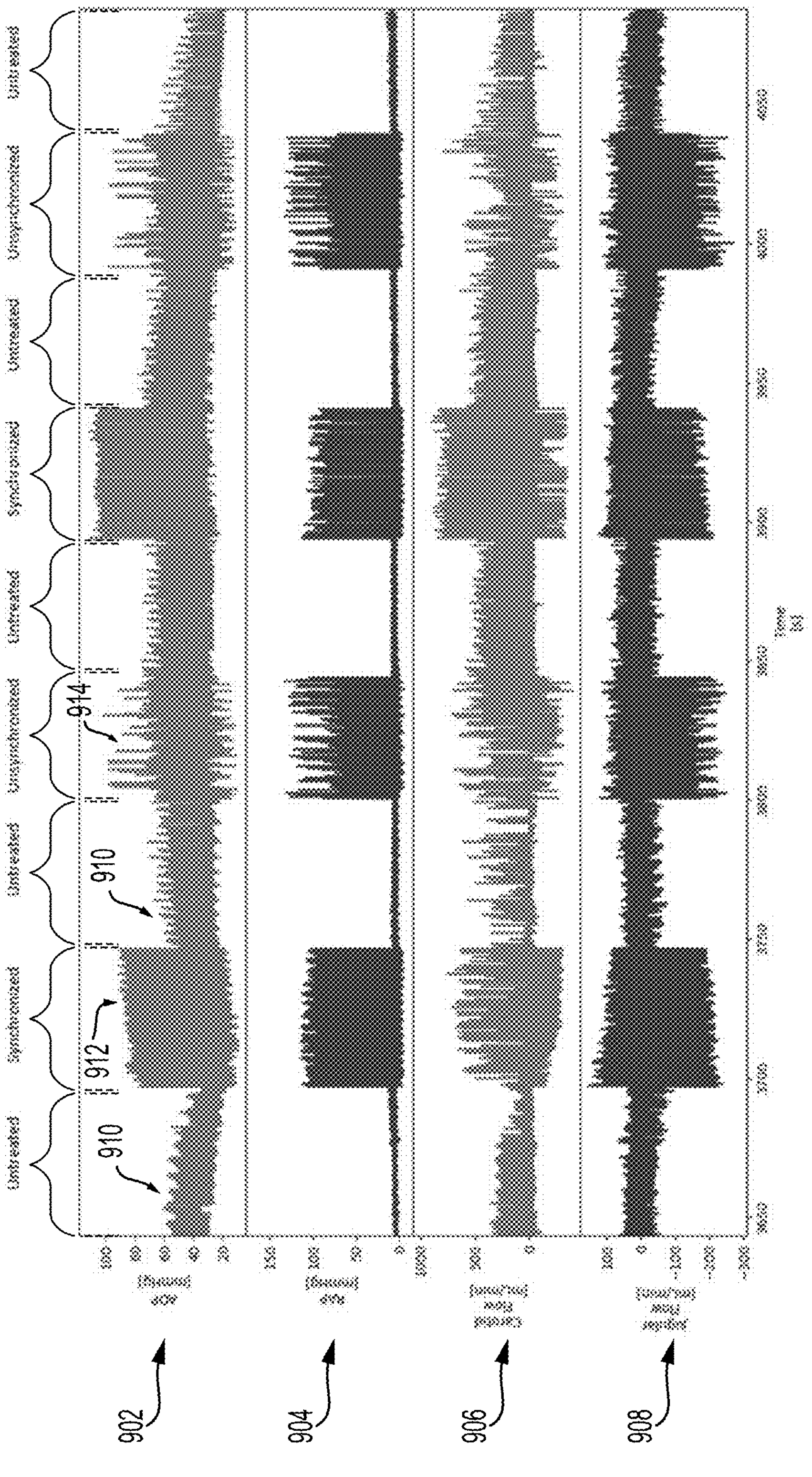
FIGS. 9A and 9B illustrate data from a scientific study showing the beneficial hemodynamic effects of synchronized chest compressions and synchronized chest compressions with additional interposed chest compression.
Figure 9B:
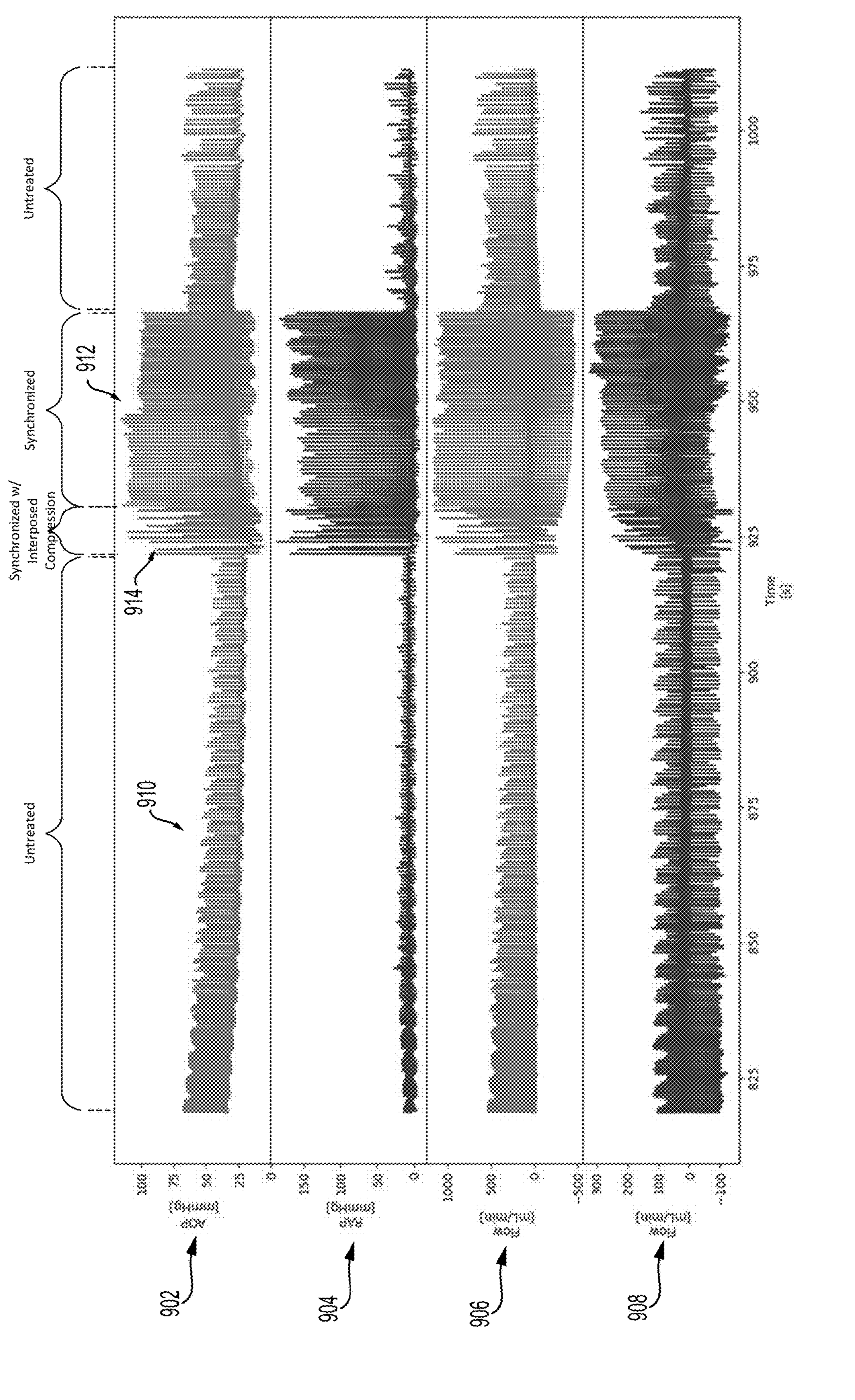

FIGS. 9A and 9B illustrate data from a scientific study, performed on a swine, showing the improved hemodynamic effects of synchronized chest compressions and/or synchronized chest compressions with additional interposed chest compressions compared to unsynchronized chest compressions.

In some cases, the PEA condition is found in cardiac arrest victims who have been defibrillated often following extended periods of fibrillation or asystole. The extended periods of fibrillation or asystole result in the myocardium being depleted of its energy stores, its contractility being degraded resulting in a PEA condition. This is particularly the case when ROSC occurs as a direct result of electrical defibrillation. In one example, synchronized compressions may be initiated as soon as an organized rhythm is detected subsequent to the delivery of the defibrillation shock. In this example, the test for unconscious hypotension in step 316 is not needed for the post-defibrillation shock, and step 316 would read: "Organized ECG?"

Referring to FIG. 9A, reference numeral 902 illustrates the aortic pressure (AOP), reference numeral 904 illustrates the right atrial pressure (RAP), reference numeral 906 illustrates the carotid flow, and reference numeral 908 illustrates the jugular flow of the test subject during the highlighted section of the study. As illustrated, several compression protocols (and non-treatment) are labeled: untreated, synchronized (e.g., first compression protocol), and unsynchronized (e.g., third compression protocol). The initial deterioration of the AOP 902 was caused by an induced asphyxia in the test subject. The first compression protocol 910 was non-treatment, which lead to a decreasing AOP 902. As no compressions are provided, the corresponding RAP 916 is near zero. If this trend was allowed to continue, then heart failure would result due to lack of blood flow.

Reference numeral 912 illustrates the effect of synchronized chest compressions (first compression protocol). As illustrated, the AOP almost immediately increases substantially. Moreover, there is a subtle, but general upward trend (starting at approximately 75 mmHG and increasing toward 90 mmHG) in the AOP indicating that the subject is improving. This upward trend illustrates the beneficial effect of using a synchronized compression protocol. Additionally, both carotid flow 906 and jugular flow 908 were also observed to have improved as well. Likewise, the corresponding RAP also increased as well with the synchronized chest compressions.

The next sequence in the testing procedure was to discontinue treatment as shown by reference numeral 910. As expected, the AOP 902 drops significantly and RAP 904 also drops back to essentially zero. The next step in the procedure 914 was to perform unsynchronized compressions (e.g., third compression protocol). While unsynchronized chest compressions are an improvement over non-treatment, the synchronized chest compressions generally provided improved hemodynamics for the subject compared to unsynchronized chest compressions and non-treatment.

As detailed previously in FIG. 4C, during unsynchronized chest compressions, some chest compressions will naturally occur around the same time as the patient's intrinsic heart rate. Consequently, the chest compressions and naturally occurring heartbeats may appear to be coordinated, but there is no intentional coordination during these unsynchronized compressions.

FIG. 9B is additional data taken from the same study as FIG. 9A. This figure illustrates the benefit of the synchronized chest compressions with the additional interposed chest compression. As before, reference numeral 902 illustrates the aortic pressure (AOP), reference numeral 904 illustrates the right atrial pressure, reference numeral 906 illustrates the carotid flow, and reference numeral 908 illustrates the jugular flow of the test subject.

The compression protocols are labeled: untreated, synchronized compressions with additional compressions (e.g., second chest compression protocol), and synchronized compressions (e.g., first chest compression protocol). As before, the initial deterioration of the AOP 902 was caused by induced asphyxia in the test subject. The first compression protocol 910 was non-treatment, which resulted in a decreasing AOP. Next, the synchronized chest compressions with an additional interposed chest compression (e.g., second chest compression protocol) was applied to the subject. As illustrated, there was an immediate improvement in the AOP 902 and RAP 904, which indicated improvement In fact, the test subject's heart rate improved such that the first chest compression protocol without the interposed compressions (e.g., synchronized chest compressions) was applied shortly thereafter because the intrinsic heart rate increased to the point that interposed compressions were not needed, likely due to the improved blood flow generated by the added interposed compressions of the second compression protocol.

Example 3: Evaluating the Hemodynamic Consequence of AHA Guideline Compliant Chest Compressions to Cardiac Electrical Activity in a Swine Model of Pseudo-Pulseless Electrical Activity Using the swine model described above with respect to Example 1, the effects of unsynchronized chest compressions compliant with AHA guidelines on hemodynamics relative to ventricular contractions during P-PEA were also studied.

Unsynchronized chest compressions compliant with AHA guidelines at 2.0 inches chest compression depth and 100 compressions per minute were applied to the P-PEA swine model. Mean arterial pressure, aortic systolic pressure, diastolic pressure, right atrial pressure, coronary perfusion pressure, and ECG were measured. The location of R-waves in the ECG and peak aortic pressures were detected via signal processing. A nearest-neighbor analysis was conducted to determine the time-gap between the R-wave and the peak aortic pressure, as provided in the figure below. The time gap in this example is defined as t_peakAOP−t_rwave. Peak aortic pressures that had more than one R-wave nearest neighbor were excluded from the analysis.

1,497 chest compressions were included in the analysis. Time gaps were divided into quartiles, and hemodynamic parameters were compared between the quartiles using a repeated measure ANOVA with Bonferroni correction. Statistical significance was defined as a p-value lower than 0.05.

The time gap quartiles were defined as: Q1: t>100 msec; Q2: 100 msec>t>0.0 msec; Q3: 0.0 msec>t>−90 msec; Q4: −90 msec>t. Analysis of the mean aortic pressure (MAP) and mean right atrial pressures (RAP) showed that a time gap of 0.0 to 100 msec (Q2) generated the highest MAP (41.1±0.6 mmHg) and a low RAP (36.8±0.3 mmHg). The coronary perfusion pressure was better if the time gap was between −90 msec and 100 msec (Q2 and Q3) than for larger time gaps. Results are shown in the Table below and in FIG. 9D.

| Metric (mmHg) | Quartile 1 (t > 100 msec) | Quartile 2 (100 msec > t > 0.0 msec) | Quartile 3 (0.0 msec > t > −90 msec) | Quartile 4 (−90 msec > t) |
|---|---|---|---|---|
| Mean Arterial Pressure | 33.8 ± 0.6 | 41.1 ± 0.6 * | 38.3 ± 0.6 | 33.1 ± 0.6 |
| Aortic Systolic Pressure | 71.0 ± 0.8 | 77.5 ± 0.8 * | 73.7 ± 0.7 | 69.2 ± 0.7 |
| Aortic Diastolic Pressure | 14.6 ± 0.5 | 20.8 ± 0.6 * | 20.1 ± 0.6 * | 15.0 ± 0.5 |
| Right Atrial Pressure | 35.3 ± 0.3 | 36.8 ± 0.3 | 40.3 ± 0.3 * | 39.6 ± 0.3 * |
| Coronary Perfusion Pressure | 11.7 ± 0.5 | 15.3 ± 0.5 * | 15.6 ± 0.5 * | 12.9 ± 0.5 |

Note:
a '*' indicates, "statistically different from other condition."

FIG. 9C is a visual representation (i.e., box plots) of the data from FIG. 9D and the above table. In general, a box plot is a method for comparing information that has been divided into separate groups. In the illustrated example, the data are the measured pressure values, and the groups (i.e., the quartiles) are the different time-windows; with time zero being the peak of the R-wave. As shown, FIG. 9D includes separate graphs for aortic pressure (AOP) 950, coronary perfusion pressure (CPP) 952, and carotid blood flow 954. Additionally, the whiskers of the box plots indicate the upper and lower bounds. In short, a larger box is better because a larger box indicates higher measured pressures, which translates into better hemodynamics for the test subject.

The results suggest that quartiles 2 and 3 had the best results. That is, a chest compression that generates peak aortic pressure (e.g., when the chest compression is at the target depth) within the time windows from approximately 100 ms before to approximately 100 ms after the R-wave are preferable to chest compressions outside of that those windows. Additionally, the data appears to indicate that there may even be a slight benefit to having the peak pressure generated after the R-Wave (i.e., Quartile 3). Accordingly, the data further provides evidence that shorter time gaps relative to the peak of the R-Wave, both before and after the peak of the R-wave, are associated with improved hemodynamics.

Figure 10A:
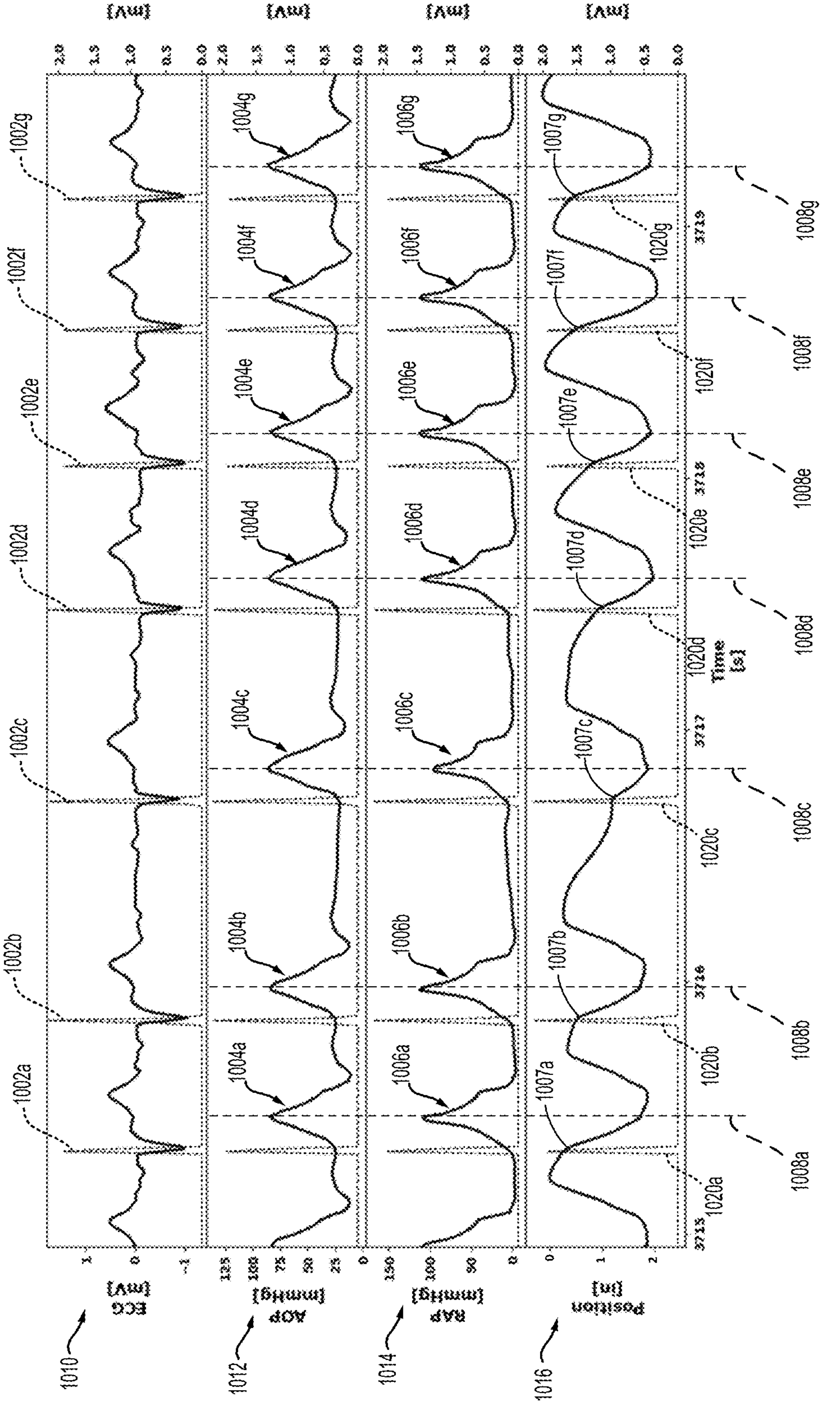
FIGS. 10A and 10B illustrate waveforms from the study detailed in FIGS. 9A-9*d*, and illustrate the relationships between a detected QRS complex, the initiation of a chest compression, and associated pressure measurements.

FIG. 10A is a series of time graphs illustrating synchronized chest compression data obtained from a study detailed above. Specifically, the time graphs depict the relationships between detected QRS complexes (in the ECG data labeled ECG 1010), chest compressions (labeled Position 1016), the measured right atrial pressure (labeled RAP 1014), and the measured aortic pressure (labeled AOP 1012) when compressions are synchronized to the intrinsic heartbeat of the subject.

In more detail, ECG data 1010 is obtained via ECG sensors attached to the test subject. In this example, the ECG data appears inverted. Thus, traditionally positive values are negative, and the traditionally negative values are positive. For example, the R-waves, which are often displayed as a positive value or peak appear as downward peaks in this data. Accordingly, while it may appear the detection signals 1002*a-g* are triggered on the Q or S wave (which are traditionally negative), they were triggered on the R-wave.

Each time an R-wave is detected, a detection signal 1002*a-g* is generated. In response to the detection signals 1002*a-g*, the chest compressor initiated a chest compression 1007*a-g* on the test subject. These chest compressions 1007*a-g* were captured via one or more accelerometers attached to the subject. As illustrated, the detection signals 1002*a-g* immediately precede the initiated chest compressions 1007*a-g*, which provide evidence that the chest compressions 1007*a-g* were initiated in response to the detection of the R-waves.

As detailed previously, RAP values are typically fairly low values (e.g., 2-6 mmHG) for natural heartbeats. Consequently, a much large RAP value is indicative of a chest compression being performed. As seen in the RAP data 1014, all of the RAP values are approximately 100 mmHG or more. These relatively high values are indicative of values caused by chest compressions.

Furthermore, dotted lines 1008*a-g* represent the points in time when the downstroke portion of the chest compressions 1007*a-g* reached a target chest compression depth (i.e., target depth). As illustrated, the RAP peaks, AOP peaks, and the point when the compressions were at target depth are all aligned. Specifically, as the chest compressions 1007*a-g* are synchronized to the intrinsic heart rate of the subject in this portion of the data, the target depth (dotted lines 1008*a-g*), peaks of right atrial pressures (RAP) 1006*a-g*, and the peaks of the aortic pressures (AOP) 1004*a-g* are all aligned for each chest compression, as would be expected. This coordination of the compression and peak pressures illustrates the synchronization of the chest compression 1007*a-g* with the detected heartbeats. As will be seen in FIG. 10B, unsynchronized chest compressions lack this alignment between the target depth and AOP peaks.

In the study from which this data was obtained, the target depth was set to 2 inches. In general, the target depth is how deep the chest compressor was programmed to compress the chest of the subject during each chest compression. However, for detection purposes (i.e., detecting when the target depth is reached), the target depth was determined to have been successfully achieved upon meeting or exceeding approximately 90% of the target depth (e.g., a "90% point"). Illustrated by way of example, the target depth was set to 2.0 inches. Accordingly, for detection purposes, the target depth was determined to have been reached successfully upon reaching 90% of 2.0 inches (or 1.8 inches). This 90% point provides a tolerance that account for minor variations in the compressions or measurements. Or, put another way, the actual depth of compression may be within approximately 10% of the target depth. For example, when the target depth of the compressor is 2.0 inches, within normal tolerance constraints, the actual depth of compression may be between approximately 1.8-2.2 inches. In alternative embodiments, the 90% point could alternatively be a 75% point, an 80% point, an 85% point, a 95% point, a 98% point, or a 99% point.

Additional evidence that the chest compressions 1007*a-g* are synchronized with the intrinsic heartbeats is shown non-uniform spacing of the chest compression in the position data 1016. This non-uniformity in the spacing of position data indicates that the chest compressions 1007*a-g* are not occurring a predefined rate.

Figure 10B:
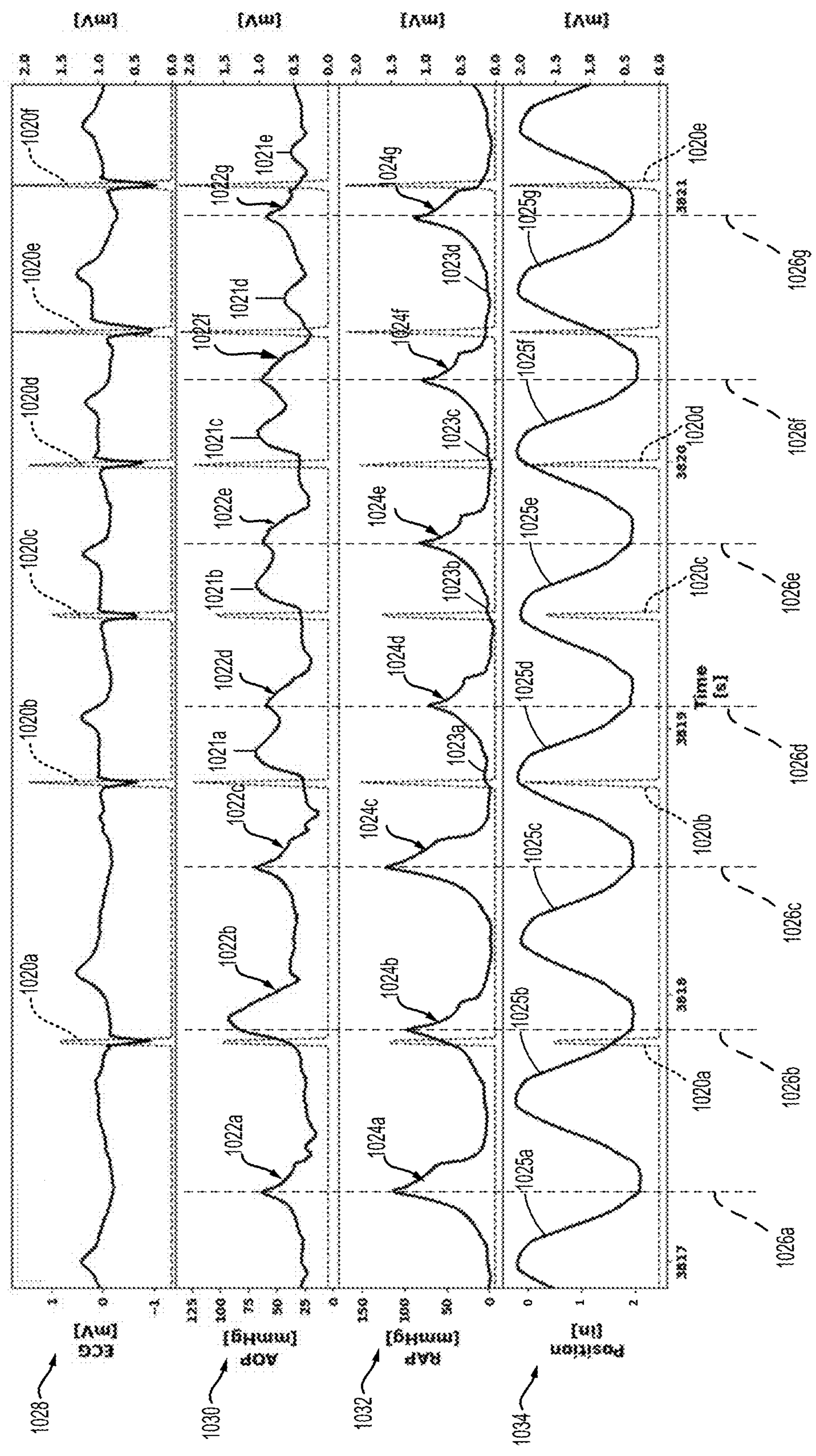

FIG. 10B is a series of time graphs illustrating unsynchronized data and illustrates the lack of coordination and alignment between a detected QRS complex (e.g., ECG data 1028) and chest compressions (position data 1034).

The most obvious indication of lack of synchronization is the fact that there are only six detected heartbeats (i.e., detection signals 1020*a-f*), but there are 7 chest compressions 1025*a-g*. Additionally, whereas there was non-uniform spacing (i.e., timing) for chest compressions in FIG. 10A (due to the chest compression occurring in response to detected QRS complexes), here the chest compressions 1025*a-g* are all evenly spaced apart. This even spacing indicates that the chest compressions are being performed at a predefined rate (e.g. 100 compressions per minute), and occur regardless of detection signals 1020*a-f*. Whereas in FIG. 10A, a detection signal (1002*a-g*) caused a chest compression, that is not the case in FIG. 10B. In this example, the chest compression and heartbeats operate independently of each other. As illustrated, the detection signals 1020*a-f* occur at various points through chest compression 1025*a-g* (unlike in FIG. 10A where the chest compressions immediately followed a detection signal).

Referring to when chest compression 1025*a* of FIG. 10B occurs, the pressure generated by this compression results in a RAP peak 1024*a* and an AOP peak 1022*a*. As this chest compression 1025*a* does not occur during the timing of a heartbeat, the AOP value is generally lower in value compared to AOP peaks in which the compression happened to occur at a time point when a QRS complex had appeared. A similar effect is observed for when the third chest compression 1025*c* occurs in that an AOP peak 1022*c* is generated, however, the magnitude of the AOP peak 1022*c* is less than that which would typically be observed when chest compressions are time aligned with the intrinsic heartbeat.

Referring to chest compression 1025*b* of FIG. 10B, as discussed above, due to the variable nature of when the test subject's heartbeats occurred, some chest compressions would naturally occur during a period in which the intrinsic heartbeat also occurs. This naturally occurring timing is illustrated by when the detection signal 1020*a* for an R-wave and chest compression 1025*b* are marked, and is shown as the time at which the target chest compression depth is reached 1026*b* is substantially aligned with the RAP peak 1024*b*, which is also substantially aligned with the AOP peak 1022*b*.

The lack of time alignment between the QRS complex and chest compressions becomes apparent in subsequent compressions. For instance, in FIG. 10B, chest compressions 1025*d*, 1025*e*, 1025*f* occurred at times that were not well aligned with intrinsic heart beats. Referring to the AOP data 1030, rather than generating a single, rather strong AOP peak (as demonstrated by peaks 1004*a-g* of FIG. 10A and peak 1022*b* of FIG. 10B in which the chest compressions were well timed), the timing of the fourth chest compression 1025*d* results in "double peaks." These double peaks (i.e., 1021*a* and 1022*d*; 1021*b* and 1022*e*; and 1021*c* and 1022*f*) generally result in less forward blood flow from the heart as compared to compressions that are properly timed with the heartbeat.

In more detail, upon detection of a heartbeat, the detection signal 1020*b* is generated. A RAP peak 1023*a* is generated, which is small in value as expected for a natural heartbeat, and corresponds with the AOP peak 2021*a*. While the heartbeat is occurring, chest compression 1025*d* was initiated. Accordingly, due to the compression 1025*d*, the resulting RAP peak 1024*d* is higher than the RAP peak 1023*a* resulting from the natural heartbeat, and a "secondary" AOP peak 1022*d* also results. This process repeats itself again with respect to detections signals 1020*c* and 1020*d*, and chest compressions 1025*e* and 1025*f*, respectively.

Lastly, as shown with respect to AOP peaks 1022*f*, 1021*d*, 1022*g*, and 1021*e*, the effects of being significantly out of synch for several chest compressions can cause "cascading" drops in pressure. In more detail, during the upstroke of chest compression 1025*f*, a heartbeat occurs (and a detection signal 1020*e* is generated). However, a possible theory is that this intrinsic heartbeat occurs when the heart is already in diastole (i.e., attempting to refill with blood from the pressure change resulting from chest compression 1025*f*). Accordingly, a weak AOP peak 1021*d* is measured because the heart was unable to completely refill with blood after the chest compression 1025*f* The heart once again goes into diastole from the intrinsic heartbeat (identified by detection signal 1020*e*). Again, the next chest compression 1025*g* occurs and interrupts the refilling and ejects the blood during the downstroke. As the heart was unable to completely refill (again), another relatively weak AOP peak 1022*g* is generated.

And yet again, a heartbeat (identified by detection signal 1020*f*) occurs in the middle of diastole (from the chest compression 1025*g*). The result is an even weaker AOP value at AOP peak 1021*e*. In short, due to a series of compressions and heartbeats being significantly out of synch (e.g., greater than 200 ms before or after the peak of the R-wave), the effectiveness of each subsequent chest compressions diminishes, and is observed to continue to diminish until the chest compressions are applied according to desirable timing relative to intrinsic heartbeats (e.g., 1020*a*, and 1025*b*) and/or until the compressions occur as such large enough intervals so as not to interfere with one another (e.g. 1025*a* and 1020*a*).

As detailed previously, the subject's heartbeat is variable. Consequently, the detrimental effects of the chest compressions being significantly out of synchronization (e.g., e.g., greater than 200 ms before or after the peak of the R-wave) typically only lasts for short periods of time. However, as shown in FIG. 9A (e.g., with unsynchronized data 916), the detrimental effects may occur, often repeatedly, in the future when the chest compressions and heartbeats become significantly unsynchronized again. Proper synchronization of the chest compression with intrinsic heart beats so that the target compression depth is reached at the appropriate time relative to the QRS complex (e.g., within 150 msec before or after the peak of the R-wave, within 100 msec before or after the peak of the R-wave), in accordance with the present disclosure results in overall improved hemodynamics.

Figure 11:
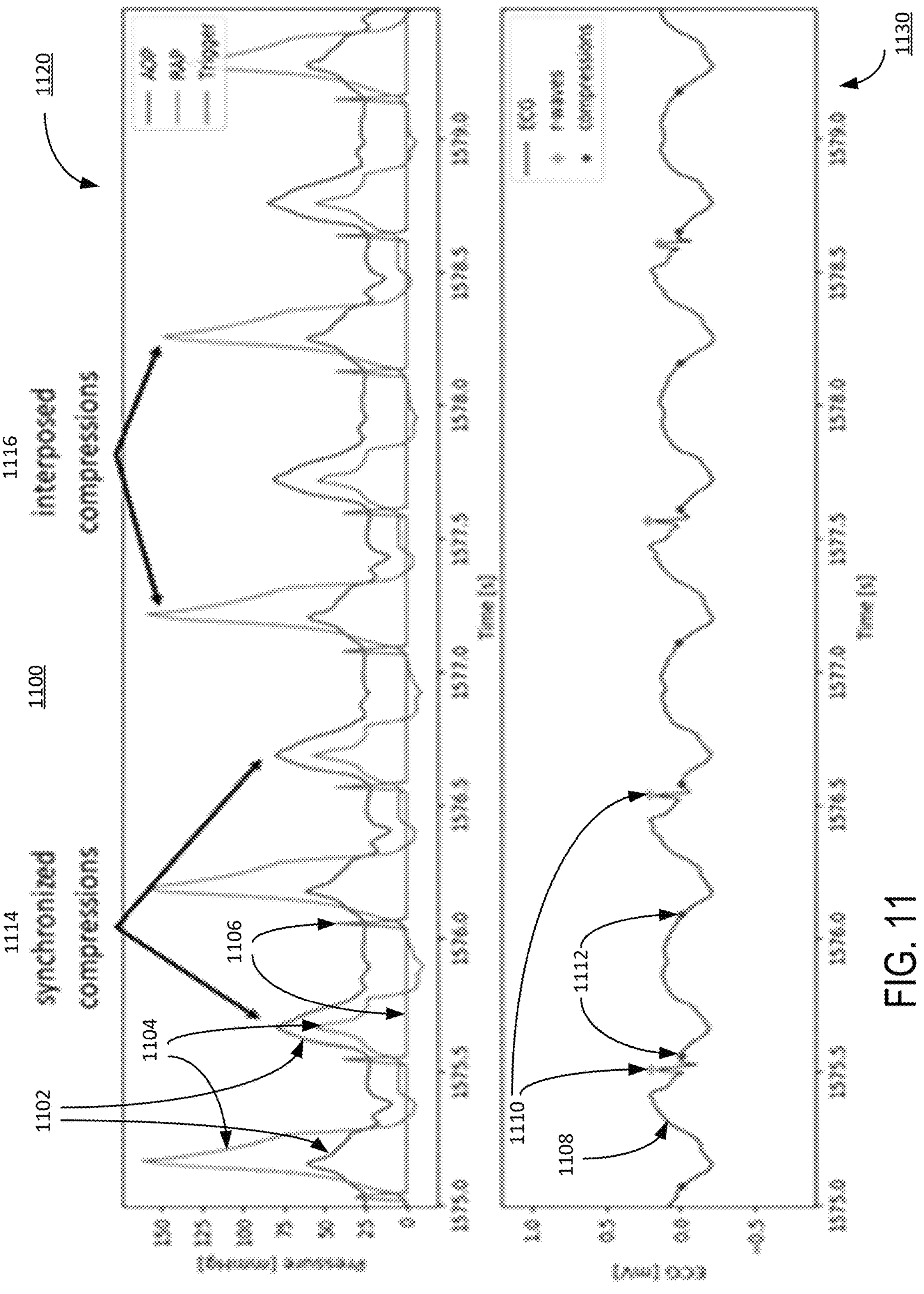
FIG. 11 illustrates data from a scientific study showing detection of R-waves, determination of intrinsic heart rate, and providing of triggers, as well as demonstrating that the relative difference in hemodynamics between synchronized chest compressions and interposed chest compressions, according to some embodiments.

FIG. 11 illustrates data from a scientific study showing detection of R-waves, determination of intrinsic heart rate, and providing of triggers to initiate chest compressions, as well as demonstrating that synchronized chest compressions can generate superior hemodynamics than interposed chest compressions, according to some embodiments. As detailed further below, FIG. 11 illustrates aortic and right atrial blood pressure as a function of time, as well as mechanical chest compression triggers, and illustrates synchronized and interposed chest compressions.

The scientific study resulting in the data shown in FIG. 11 involved three approximately 30 kg domestic swine that were sedated with an intra-muscular injection of ketamine and xylazine and anesthetized via isoflurane inhalation. After anesthesia, the animals underwent surgical preparation that included the placement of solid-state pressure transducers in the aorta and the right atrium as well as the placement of perivascular ultrasound blood flow transducers around the left common carotid artery and external jugular vein. After surgical preparation, anesthesia transitioned to continuous rate infusion of ketamine and midazolam. A systolic blood pressure of 50 mmHg was induced by reducing the inspired oxygen fraction to 6%. After this, the inspired oxygen fraction was increased to 10% and chest compressions were delivered, either as synchronized to the R-wave, or as a combination of synchronized and interposed compressions. Blood pressures and flows were analyzed on a per compression basis.

Results included the following. An example 1100 of the synchronized and interposed compressions is shown in FIG. 11. In top panel 1120, the aortic pressure is shown by curve 1102, the right atrial pressure is shown by curve 1104 and the signal that triggers the mechanical chest compressions is shown by curve 1106. In bottom panel 1130, the ECG tracing is shown by curve 1108. The large oscillations demonstrate the artifact that chest compressions create in the ECG signal. Plus signs 1110 represent detected R-waves, and dots 1112 represent the beginning of each chest compression. Shown are a combination of chest compressions synchronized to the R-wave 1114 and interposed chest compressions 1116 delivered at a ratio of one interposed compression per each heartbeat (the heart rate was between 40 and 60 beats per minute). The maximum aortic pressure created by a synchronized chest compression is higher than the maximum aortic pressure created by an interposed chest compression. Conversely, the maximum right atrial pressure generated by an interposed compression is higher than the maximum right atrial pressure created by a synched compression. Finally, comparing the aortic pressure to the right atrial pressure within a single compression, it is apparent that the aortic pressure is higher than the right atrial pressure during a synchronized compression and the opposite is true during an interposed compression. The synchronized compressions manifested higher aortic pressures and lower right atrial pressures which are generally associated with better tissue perfusion.

These results and data demonstrate, among other things, that in some embodiments, for example, one or more algorithms are capable of detecting the R-wave in the ECG, determining the intrinsic heart rate, providing triggers to synchronized chest compressions to the R-wave, and providing additional interposed chest compressions based on intrinsic heart rate. In addition, these results and data demonstrate that the synchronized chest compressions generated superior hemodynamics than the interposed chest compressions.

OTHER CONSIDERATIONS

The features described can be implemented in digital electronic circuitry, or in computer hardware, firmware, software, or in combinations of them. The apparatus can be implemented in a computer program product tangibly embodied in an information carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device.

A computer program is a set of instructions that can be used, directly or indirectly, in a computer to perform some activity or bring about some result. A computer program can be written in any form of programming language, including compiled or interpreted languages, and it can be deployed in any form, including as a stand-alone program or as a module, component, subroutine, or other unit suitable for use in a computing environment. Storage devices suitable for tangibly embodying computer program instructions and data include all forms of non-volatile memory, including by way of example semiconductor memory devices, such as EPROM, EEPROM, and flash memory devices, magnetic disks such as internal hard disks and removable disks, magneto-optical disks, and CD-ROM and DVD-ROM disks.

The computing devices described herein may include, or be operatively coupled to communicate with, one or more mass storage devices for storing data files; such devices include magnetic disks, such as internal hard disks and removable disks; magneto-optical disks; and optical disks.

The terms "machine-readable medium," "computer-readable medium," and "processor-readable medium" as used herein, refer to any medium that participates in providing data that causes a machine to operate in a specific fashion. Using a computer system, various processor-readable media (e.g., a computer program product) might be involved in providing instructions/code to processor(s) for execution and/or might be used to store and/or carry such instructions/code (e.g., as signals).

In many implementations, a processor-readable medium is a physical and/or tangible storage medium. Such a medium may take many forms, including but not limited to, non-volatile media and volatile media. Non-volatile media include, for example, optical and/or magnetic disks. Volatile media include, without limitation, dynamic memory.

Common forms of physical and/or tangible processor-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, EPROM, a FLASH-EPROM, any other memory chip or cartridge, a carrier wave as described hereinafter, or any other medium from which a computer can read instructions and/or code.

Various forms of processor-readable media may be involved in carrying one or more sequences of one or more instructions to one or more processors for execution. Merely by way of example, the instructions may initially be carried on a flash device, a device including persistent memory, and/or a magnetic disk and/or optical disc of a remote computer. A remote computer might load the instructions into its dynamic memory and send the instructions as signals over a transmission medium to be received and/or executed by a computer system.

The computing devices described herein may be part of a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet. The computer system can include clients and servers. A client and server are generally remote from each other and typically interact through a network, such as the described one. The relationship of client and server arises by virtue of computer programs running on the respective computers and having a client-server relationship to each other.

Substantial variations may be made in accordance with specific requirements. For example, customized hardware might also be used, and/or particular elements might be implemented in hardware, software (including portable software, such as applets, etc.), or both. Further, connection to other computing devices such as network input/output devices may be employed.

Information and signals may be represented using any of a variety of different technologies and techniques. For example, data, instructions, commands, information, signals, and symbols that may be referenced throughout the above description may be represented by voltages, currents, electromagnetic waves, magnetic fields or particles, optical fields or particles, or any combination thereof.

The methods, systems, and devices discussed above are examples. Various alternative configurations may omit, substitute, or add various procedures or components as appropriate. Configurations may be described as a process which is depicted as a flow diagram or block diagram. Although each may describe the operations as a sequential process, many of the operations can be performed in parallel or concurrently. In addition, the order of the operations may be rearranged. A process may have additional stages not included in the figure. Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the scope of the disclosure.

Also, configurations may be described as a process which is depicted as a flow diagram or block diagram. Although each may describe the operations as a sequential process, many of the operations can be performed in parallel or concurrently. In addition, the order of the operations may be rearranged. A process may have additional stages or functions not included in the figure. Furthermore, examples of the methods may be implemented by hardware, software, firmware, middleware, microcode, hardware description languages, or any combination thereof. When implemented in software, firmware, middleware, or microcode, the program code or code segments to perform the tasks may be stored in a non-transitory processor-readable medium such as a storage medium. Processors may perform the described tasks.

Components, functional or otherwise, shown in the figures and/or discussed herein as being connected or communicating with each other are communicatively coupled. That is, they may be directly or indirectly connected to enable communication between them.

As used herein, including in the claims, "and" as used in a list of items prefaced by "at least one of" indicates a disjunctive list such that, for example, a list of "at least one of A, B, and C" means A or B or C or AB or AC or BC or ABC (i.e., A and B and C), or combinations with more than one feature (e.g., AA, AAB, ABBC, etc.). As used herein, including in the claims, unless otherwise stated, a statement that a function or operation is "based on" an item or condition means that the function or operation is based on the stated item or condition and may be based on one or more items and/or conditions in addition to the stated item or condition.

Having described several example configurations, various modifications, alternative constructions, and equivalents may be used without departing from the disclosure. For example, the above elements may be components of a larger system, wherein other rules may take precedence over or otherwise modify the application of the present system. Also, a number of operations may be undertaken before, during, or after the above elements are considered. Also, technology evolves and, thus, many of the elements are examples and do not bound the scope of the disclosure or claims. Accordingly, the above description does not bound the scope of the claims. Further, more than one present system may be disclosed.

Other embodiments are within the scope of the present system. For example, due to the nature of software, functions described above can be implemented using software, hardware, firmware, hardwiring, or combinations of any of these. Features implementing functions may also be physically located at various locations, including being distributed such that portions of functions are implemented at different physical locations.

What is claimed is:

1. A system for providing resuscitative chest compressions to a chest of a patient, the system comprising:
   a chest compressor configured to be applied to the chest of the patient and to administer chest compressions to the patient;
   one or more sensors communicatively coupled to a medical device and configured to sense electrocardiogram (ECG) signals of the patient and to transmit the ECG signals to the medical device; and
   at least one processor coupled to memory of the medical device, the at least one processor and memory configured to:
      receive the ECG signals,
      determine an intrinsic heart rate of the patient based on the ECG signals,
      identify at least one ECG waveform feature within the ECG signals,
      select a chest compression protocol from at least three predetermined chest compression protocols for administration to the patient based on the intrinsic heart rate of the patient, the at least three predetermined chest compression protocols comprising a first chest compression protocol selected based on whether the intrinsic heart rate of the patient falls within a first range, a second chest compression protocol selected based on whether the intrinsic heart rate of the patient falls within a second range, and a third chest compression protocol selected based on whether the intrinsic heart rate of the patient falls within a third range, the first range, second range, and third range being distinct from one another, and
      control the chest compressor based on the selected chest compression protocol.

2. The system of claim 1, wherein the first chest compression protocol and the second chest compression protocol each comprise compressions synchronized with the at least one identified ECG waveform feature, and the third chest compression protocol comprises chest compressions that are unsynchronized with the at least one identified ECG waveform feature.

3. The system of claim 1, wherein the selected chest compression protocol comprises the first chest compression protocol, and wherein the first range comprises an intrinsic heart rate of between approximately 60 and approximately 120 beats per minute.

4. The system of claims 3, wherein the at least one ECG waveform feature includes at least one of: a QRS complex, a leading edge of an R-wave, a peak of an R-wave, and a Q-wave.

5. The system of claim 3, wherein the at least one processor is configured to pause the chest compressor from administering one or more chest compressions during a check for return of spontaneous circulation (ROSC) or in response to a determination that the patient has achieved ROSC.

6. The system of claim 1, wherein the selected chest compression protocol comprises the second chest compression protocol, wherein the second chest compression protocol comprises compressions synchronized with the at least one identified ECG waveform feature with at least one additional compression interposed between the compressions synchronized with the at least one identified ECG waveform feature, and wherein the at least one additional compression comprises multiple compressions interposed between the compressions synchronized with the at least one identified ECG waveform feature.

7. The system of claim 6, wherein the second range comprises an intrinsic heart rate of between approximately 40 beats per minute and approximately 60 beats per minute.

8. The system of claim 6, wherein the at least one ECG waveform feature includes at least one of: a QRS complex, a leading edge of an R-wave, a peak of an R-wave, and a Q-wave.

9. The system of claim 6, wherein the at least one processor is configured to pause the chest compressor from administering one or more chest compressions during a check for return of spontaneous circulation (ROSC) or in response to a determination that the patient has achieved ROSC.

10. The system of claim 1, wherein the selected chest compression protocol comprises the third chest compression protocol, wherein the third chest compression protocol comprises compressions administered according to a predetermined rate, wherein the predetermined rate comprises chest compressions delivered at a rate between approximately 80 and approximately 100 compressions per minute, wherein the third range comprises an intrinsic heart rate between approximately 0 and approximately 40 beats per minute.

11. The system of claim 10, wherein the at least one ECG waveform feature includes at least one of: a QRS complex, a leading edge of an R-wave, a peak of an R-wave, and a Q-wave.

12. The system of claim 10, wherein the at least one processor is configured to pause the chest compressor from administering one or more chest compressions during a check for return of spontaneous circulation (ROSC) or in response to a determination that the patient has achieved ROSC.

13. The system of claim 1, wherein:
   the at least three predetermined chest compression protocols comprises a fourth chest compression protocol for administration to the patient when the intrinsic heart rate of the patient falls within a fourth range;
   the fourth chest compression protocol comprises compressions synchronized with the at least one identified ECG waveform feature and adjustment of at least one chest compression parameter;
   the at least one chest compression parameter comprises at least one of: a compression depth, a compression hold time, a compression release velocity, a compression downstroke time, a compression upstroke time, and a compression force; and
   wherein the adjustment of the at least one chest compression parameter comprises at least one of: a reduction in compression depth from an initial compression depth, a reduction in compression hold time from an initial compression hold time, an increase in compression release velocity from an initial compression release velocity, a reduction in compression downstroke time from an initial compression downstroke time, and a reduction in compression upstroke time from an initial compression upstroke time.

14. The system of claim 1, wherein the at least three predetermined chest compression protocols comprises a fourth chest compression protocol for administration to the patient when the intrinsic heart rate of the patient falls within a fourth range, and wherein the fourth range comprises a heart rate of between approximately 120 beats per minute and approximately 150 beats per minute.

15. The system of claim 1, wherein:
   the at least one processor is configured to initiate a shock protocol when the intrinsic heart rate of the patient falls within a fifth range;

the shock protocol analyzes the signals corresponding to the electrocardiogram (ECG) of the heart of the patient to identify shockable rhythms, and apply one or more therapeutic shocks in response to identifying the shockable rhythms; and the fifth range comprises a heart rate of greater than approximately 150 beats per minute.

16. The system of claim 1, wherein:

the at least one processor comprises a first processor configured to process the ECG signals corresponding to the ECG of the heart and control the chest compressor to provide the chest compressions; and wherein the at least one processor comprises a second processor configured to control the chest compressor to provide the chest compressions;

the at least one processor and memory are disposed in a medical device comprising at least one of: a defibrillator-monitor, an automated external defibrillator, an automated chest compressor, a wearable defibrillator, and an active compression-decompression device; and the chest compressor comprises a compression belt and a belt tensioner configured to tighten the compression belt around a thorax of the patient in order to compress the thorax of the patient at a resuscitative rate.

17. The system of claim 1, wherein the chest compressor is a piston-based system that comprises:

a piston, a piston driver, support structures for supporting the piston and piston driver, and a compression pad affixed to the piston.

18. The system of claim 1, wherein:

selecting the chest compression protocol from the at least three predetermined chest compression protocols comprises selecting the chest compression protocol from at least four predetermined chest compression protocols;

the at least four predetermined chest compression protocols comprise a first chest compression protocol, a second chest compression protocol and a third chest compression protocol that each comprises compressions synchronized with the at least one identified ECG waveform feature, and wherein the at least four predetermined chest compression protocols comprise a fourth chest compression protocol that comprises unsynchronized chest compressions the first chest compression protocol is selected based on whether the intrinsic heart rate of the patient falls within a first range, the second chest compression protocol is selected based on whether the intrinsic heart rate of the patient falls within a second range, the third chest compression protocol is selected based on whether the intrinsic heart rate of the patient falls within a third range, and the fourth chest compression protocol is selected based on whether the intrinsic heart rate of the patient falls within a fourth range;

the first range comprises an intrinsic heart rate of between approximately 60 and approximately 120 beats per minute;

the second range comprises a heart rate of between approximately 40 beats per minute and approximately 60 beats per minute;

the second chest compression protocol comprises compressions synchronized with the at least one identified ECG waveform feature with at least one additional compression interposed between the compressions synchronized with the at least one identified ECG waveform feature;

the third range comprises an intrinsic heart rate between approximately 20 and approximately 40 beats per minute;

the third chest compression protocol comprises compressions synchronized with the at least one identified ECG waveform feature with at least two additional compressions interposed between the compressions synchronized with the at least one identified ECG waveform feature;

the fourth range comprises an intrinsic heart rate between approximately 0 and approximately 20 beats per minute;

the fourth protocol comprises compressions administered according to a predetermined rate; and the predetermined rate comprises chest compressions delivered at a rate between approximately 80 and approximately 100 compressions per minute.

19. The system of claim 18, wherein:

the at least four predetermined chest compression protocols comprises a fifth chest compression protocol for administration to the patient when the intrinsic heart rate of the patient falls within a fifth range;

the fifth range comprises a heart rate of between approximately 120 beats per minute and approximately 150 beats per minute;

the fifth chest compression protocol comprises compressions synchronized with the at least one identified ECG waveform feature and adjustment of at least one chest compression parameter; and the at least one processor is configured to initiate a shock protocol when the intrinsic heart rate of the patient falls above approximately 150 beats per minute.

20. The system of claim 1, wherein:

selecting the chest compression protocol from the at least three predetermined chest compression protocols comprises selecting the chest compression protocol from at least four predetermined chest compression protocols;

wherein the at least four predetermined chest compression protocols comprise a first chest compression protocol, a second chest compression protocol and a third chest compression protocol that each comprises compressions synchronized with the at least one identified ECG waveform feature, and wherein the at least four predetermined chest compression protocols comprise a fourth chest compression protocol that comprises unsynchronized chest compressions; and the first chest compression protocol is associated with a first intrinsic heart beat range, the second chest compression protocol is associated with a second intrinsic heart beat range, the third chest compression protocol is associated with a third intrinsic heart beat range, and the fourth chest compression protocol is associated with a fourth intrinsic heart beat range.

21. The system of claim 20, wherein at least some of the first intrinsic heart beat range, the second intrinsic heart beat range, the third intrinsic heart beat range and the fourth intrinsic heart beat range overlap, and wherein transitioning from one of the at least four predetermined chest compression protocols that is currently being administered to another of the at least four predetermined chest compression protocols occurs when the patient's intrinsic heart beat range changes so as to fall outside of the range associated with the one of the at least four predetermined chest compression protocols that is currently being administered.

22. The system of claim 21, wherein the protocol that is transitioned to has an associated range that includes the patient's current intrinsic heart beat rate, wherein the intrinsic heart beat range associated with the first chest compression protocol is between approximately 60 and approximately 120 beats per minute, and wherein the intrinsic heart beat range associated with the second chest compression protocol is between approximately 40 and approximately 70 beats per minute.

23. The system of claim 22, wherein the second chest compression protocol comprises compressions synchronized with the at least one identified ECG waveform feature with at least one additional compression interposed between the compressions synchronized with the at least one identified ECG waveform feature.

24. The system of claim 22, wherein the intrinsic heart beat range associated with the third chest compression protocol is between approximately 20 and approximately 50 beats per minute, and wherein the third chest compression protocol comprises compressions synchronized with the at least one identified ECG waveform feature with at least two additional compressions interposed between the compressions synchronized with the at least one identified ECG waveform feature, and wherein the intrinsic heart beat range associated with the fourth chest compression protocol is between approximately 0 and approximately 30 beats per minute, wherein the fourth protocol comprises compressions administered according to a predetermined rate, wherein the predetermined rate comprises chest compressions delivered at a rate of between approximately 80 and approximately 100 compressions per minute, wherein the at least four predetermined chest compression protocols comprises a fifth chest compression protocol, wherein an intrinsic heart beat range associated with the fifth chest compression protocol is between approximately 110 and approximately 150 beats per minute, wherein the fifth chest compression protocol comprises compressions synchronized with the at least one identified ECG waveform feature administered at a rate of two for every three intrinsic heart beats, and wherein the at least one processor is configured to initiate a shock protocol when the intrinsic heart rate of the patient falls above approximately 150 beats per minute.

25. The system of claim 1, wherein the at least one processor is configured to adjust at least one of: the first range, the second range, and the third range, in response to a determination that the intrinsic heart rate of the patient has fallen within the first range, the second range, or the third range multiple times within a predetermined interval of time.

26. A system for providing resuscitative chest compressions to a chest of a patient, the system comprising:

a chest compressor configured to be applied to the chest of the patient and to administer chest compressions to the patient;

one or more sensors communicatively coupled to a medical device and configured to sense electrocardiogram (ECG) signals of the patient and to transmit the ECG signals to the medical device; and at least one processor coupled to memory of the medical device, the at least one processor and memory configured to:

receive the ECG signals, determine an intrinsic heart rate of the patient based on the ECG signals, identify at least one ECG waveform feature within the ECG signals, select a chest compression protocol from at least three predetermined chest compression protocols for administration to the patient based on the intrinsic heart rate of the patient, the at least three predetermined chest compression protocols comprising:

a first chest compression protocol, a second chest compression protocol, the first and second chest compression protocols each comprising compressions synchronized with the at least one identified ECG waveform feature, and a third chest compression protocol comprising unsynchronized chest compressions, and control the chest compressor based on the selected chest compression protocol.

27. The system of claim 26, wherein the first chest compression protocol is selected based on whether the intrinsic heart rate of the patient falls within a first range, and the second chest compression protocol is selected based on whether the intrinsic heart rate of the patient falls within a second range, and the third chest compression protocol is selected based on whether the intrinsic heart rate of the patient falls within a third range.

28. The system of claim 27, wherein the selected chest compression protocol comprises the first chest compression protocol, and wherein the first range comprises an intrinsic heart rate of between approximately 60 and approximately 120 beats per minute.

29. The system of claims 28, wherein the at least one ECG waveform feature includes at least one of: a QRS complex, a leading edge of an R-wave, a peak of an R-wave, and a Q-wave.

30. The system of claim 28, wherein the at least one processor is configured to pause the chest compressor from administering one or more chest compressions during a check for return of spontaneous circulation (ROSC) or in response to a determination that the patient has achieved ROSC.

31. The system of claim 27, wherein the selected chest compression protocol comprises the second chest compression protocol, wherein the second chest compression protocol comprises compressions synchronized with the at least one identified ECG waveform feature with at least one additional compression interposed between the compressions synchronized with the at least one identified ECG waveform feature, and wherein the at least one additional compression comprises multiple compressions interposed between the compressions synchronized with the at least one identified ECG waveform feature.

32. The system of claim 31, wherein the second range comprises an intrinsic heart rate of between approximately 40 beats per minute and approximately 60 beats per minute.

33. The system of claim 31, wherein the at least one ECG waveform feature includes at least one of: a QRS complex, a leading edge of an R-wave, a peak of an R-wave, and a Q-wave.

34. The system of claim 31, wherein the at least one processor is configured to pause the chest compressor from administering one or more chest compressions during a check for return of spontaneous circulation (ROSC) or in response to a determination that the patient has achieved ROSC.

35. The system of claim 27, wherein the selected chest compression protocol comprises the third chest compression protocol, wherein the third chest compression protocol comprises compressions administered according to a predetermined rate, wherein the predetermined rate comprises chest compressions delivered at a rate between approximately 80 and approximately 100 compressions per minute, wherein the third range comprises an intrinsic heart rate between approximately 0 and approximately 40 beats per minute.

36. The system of claim 35, wherein the at least one ECG waveform feature includes at least one of: a QRS complex, a leading edge of an R-wave, a peak of an R-wave, and a Q-wave.

37. The system of claim 35, wherein the at least one processor is configured to pause the chest compressor from administering one or more chest compressions during a check for return of spontaneous circulation (ROSC) or in response to a determination that the patient has achieved ROSC.

38. The system of claim 27, wherein:

the at least three predetermined chest compression protocols comprises a fourth chest compression protocol for administration to the patient when the intrinsic heart rate of the patient falls within a fourth range;

the fourth chest compression protocol comprises compressions synchronized with the at least one identified ECG waveform feature and adjustment of at least one chest compression parameter;

the at least one chest compression parameter comprises at least one of: a compression depth, a compression hold time, a compression release velocity, a compression downstroke time, a compression upstroke time, and a compression force; and wherein the adjustment of the at least one chest compression parameter comprises at least one of: a reduction in compression depth from an initial compression depth, a reduction in compression hold time from an initial compression hold time, an increase in compression release velocity from an initial compression release velocity, a reduction in compression downstroke time from an initial compression downstroke time, and a reduction in compression upstroke time from an initial compression upstroke time.

39. The system of claim 27, wherein the at least one processor is configured to adjust at least one of: the first range, the second range, and the third range, in response to a determination that the intrinsic heart rate of the patient has fallen within the first range, the second range, or the third range multiple times within a predetermined interval of time.

* * * * *